US012686679B2

(12) United States Patent
Wen et al.

(10) Patent No.:  US 12,686,679 B2
(45) Date of Patent:       Jul. 21, 2026

(54) CRYSTALS OF ALKYNYL-CONTAINING COMPOUND, SALT AND SOLVATE THEREOF, PREPARATION METHOD, AND APPLICATIONS

(71) Applicants:GUANGZHOU HEALTHQUEST PHARMA CO., LTD., Guangzhou (CN); ASCENTAGE PHARMA (SUZHOU) CO., LTD., Suzhou (CN); ASCENTAGE PHARMA GROUP CORP LIMITED, Hong Kong (CN)

(72) Inventors: Jianfeng Wen, Suzhou (CN); Yanqiong Lin, Suzhou (CN); Jianpeng Feng, Suzhou (CN); Tianzhu Wu, Suzhou (CN); Zhenzhong Shao, Suzhou (CN); Weidong Li, Suzhou (CN)

(73) Assignees: GUANGZHOU HEALTHQUEST PHARMA CO., LTD. (CN); ASCENTAGE PHARMA (SUZHOU) CO., LTD. (CN)

( * ) Notice: Subject to any disclaimer, the term of this patent is extended or adjusted under 35 U.S.C. 154(b) by 603 days.

(21) Appl. No.: 17/797,016

(22) PCT Filed: Jul. 1, 2021

(86) PCT No.: PCT/CN2021/103925
§ 371 (c)(1),
(2) Date: Aug. 2, 2022

(87) PCT Pub. No.: WO2022/002177
PCT Pub. Date: Jan. 6, 2022

(65) Prior Publication Data
US 2023/0106142 A1     Apr. 6, 2023

(30) Foreign Application Priority Data
Jul. 2, 2020   (WO) ................ PCT/CN2020/099949

(51) Int. Cl.
C07D 471/04        (2006.01)
(52) U.S. Cl.
CPC ........ C07D 471/04 (2013.01); C07B 2200/13 (2013.01)

(58) Field of Classification Search
CPC .... C07D 471/04; C07B 2200/13; A61P 35/00
See application file for complete search history.

(56) References Cited

U.S. PATENT DOCUMENTS 8,846,671 B2 * 9/2014 Ding .................... C07D 471/04
                                                          514/233.2
2013/0196985 A1   8/2013 Ding et al.

FOREIGN PATENT DOCUMENTS

CN      101885722 A   11/2010
CN      103539784 A   1/2014
CN      111499632 A   8/2020
CN      111732586 A   10/2020

OTHER PUBLICATIONS

"Hydrobromic Acid"—Wikipedia; https://en.wikipedia.org/wiki/Hydrobromic_acid, obtained from the internet Jun. 9, 2025, Internet Archive Wayback Machine Date Dec. 19, 2019. (Year: 2019).*
"Organic Acid"—Wikipedia; https://en.wikipedia.org/wiki/Organic_acid, obtained from the internet Jun. 9, 2025, Internet Archive Wayback Machine Date Jan. 1, 2020. (Year: 2020).*
International Search Report and Written Opinion dated Sep. 8, 2021 for PCT/CN2021/103925 (15 pages).
Ren et al., "Identification of GZD824 as an Orally Bioavailable Inhibitor That Targets Phosphorylated and Nonphosphorylated Breakpoint Cluster Region—Abelson (Bcr-Abl) Kinase and Overcomes Clinically Acquired Mutation-Induced Resistance against Imatinib", Journal of Medicinal Chemistry, 2013, 56, 879-894.

* cited by examiner

*Primary Examiner* — Jeffrey S Lundgren
*Assistant Examiner* — W. Justin Youngblood
(74) *Attorney, Agent, or Firm* — Honigman LLP; Lucy Yang; Li Gao

(57)            ABSTRACT

The invention discloses the crystal form, preparation method and application of an alkynyl compound, its salt and solvent compound. The invention specifically discloses 3-((1H-pyrazolo[3,4-b]pyridin-5-yl)ethynyl)-4-methyl-N-(4-((4-methylpiperazine-1-yl)methyl)-3-(trifluoromethyl)phenyl) benzamide crystal form I and 3-((1H-pyrazolo [3,4-b]pyridin-5-yl)ethynyl)-4-methyl-N-(4-((4-methylpiperazine-1-yl)methyl)-3-(trifluoromethyl)phenyl) benzamide fumarate crystal form II. The crystal form of the invention has good stability and has important value for drug optimization and development.

8 Claims, 30 Drawing Sheets

Isotherm diagram

Temperature(°C)

Isotherm diagram

Relative humidity(%)

Temperature(°C)

2θ (°)

Temperature(°C)

Temperature(°C)

Temperature(°C)

Temperature(°C)

Temperature(℃)

Temperature(℃)

Isotherm diagram

Relative humidity(%)

1

CRYSTALS OF ALKYNYL-CONTAINING COMPOUND, SALT AND SOLVATE THEREOF, PREPARATION METHOD, AND APPLICATIONS

CROSS REFERENCE TO RELATED APPLICATIONS

This application is a national phase entry pursuant to 35 U.S.C. § 371 of International Patent Application No. PCT/CN2021/103925, filed Jul. 1, 2021, which claims the priority pursuant to 35 U.S.C. § 365 (b) of International Patent Application No. PCT/CN2020/099949, filed Jul. 2, 2020, the entire of each of which is incorporated herein by reference.

FIELD OF THE INVENTION

The invention belongs to the field of chemical medicine, and particularly relates to a crystal form, preparation and application of an alkynyl-containing compound, its salt and solvate.

BACKGROUND OF THE INVENTION

This application relates to an alkynyl-containing compound with a chemical name of 3-((1H-pyrazolo [3,4-b]pyridin-5-yl)ethynyl)-4-methyl-N-(4-((4-methylpiperazine-1-yl)methyl)-3-(trifluoromethyl)phenyl) benzamide. The patent reports on this compound are very limited, and the crystal form of the above compound is not involved.

Known compounds generally have polymorphism, and general drugs may have two or more different crystalline substance states. The existence form and quantity of polymorphic compounds are unpredictable. Different crystal forms of the same drug have significant differences in solubility, melting point, density, stability, etc., which affect the temperature profile, uniformity, biological characteristics and Efficacy and safety. Therefore, in the process of new drug development, a comprehensive polymorphic screening of compounds is required, and it is of great clinical significance to select a crystal form suitable for the development of pharmaceutical preparations.

SUMMARY OF THE INVENTION

The invention provides a crystal form, preparation and application of an alkynyl-containing compound, its salt and solvate. The crystal form of the invention has good stability and is of great value to the optimization and development of medicines.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide crystal form 3, which has characteristic peaks at the following positions in the XRPD diagram represented by 20 angles: 9.498±0.2°,, 12.293±0.2°, 13.045±0.2°, 15.899±0.2°, 16.199±0.2°, 18.183±0.2°, 18.327±0.2°, 21.755±0.2°, 22.362±0.2°, 25.690±0.2°;
or characteristic peaks at 8.968±0.2°, 9.498±0.2°, 12.293±0.2°, 13.045±0.2°, 15.899±0.2°, 16.199±0.2°, 16.533±0.2°, 16.908±0.2°, 18.183±0.2°, 18.327±0.2°, 20.042±0.2°, 20.271±0.2°, 21.755±0.2°, 22.362±0.2°, 25.690±0.2°.

In some preferred embodiments of the present invention, crystal form I has characteristic peaks at the following positions in the XRPD diagram represented by 20 angles, as shown in the Table 1 below;

2

TABLE 1

| Diffraction angle (2θ°) | d value (Å) | Relative Strength (%) |
|---|---|---|
| 8.968 | 9.8525 | 11.6 |
| 9.498 | 9.3037 | 20.4 |
| 10.820 | 8.1699 | 2.1 |
| 12.293 | 7.1943 | 40.3 |
| 13.045 | 6.7812 | 25.3 |
| 13.842 | 6.3923 | 0.3 |
| 15.899 | 5.5696 | 65.5 |
| 16.199 | 5.467 | 31.8 |
| 16.533 | 5.3574 | 10.4 |
| 16.908 | 5.2396 | 14.4 |
| 18.183 | 4.8748 | 20 |
| 18.327 | 4.8368 | 25.7 |
| 18.551 | 4.7789 | 2.8 |
| 18.954 | 4.6783 | 2.8 |
| 19.644 | 4.5156 | 2.8 |
| 19.869 | 4.4649 | 9 |
| 20.042 | 4.4267 | 15.1 |
| 20.271 | 4.3772 | 10.7 |
| 20.987 | 4.2294 | 0.3 |
| 21.755 | 4.0819 | 100 |
| 22.362 | 3.9724 | 29.3 |
| 22.941 | 3.8733 | 1.2 |
| 23.599 | 3.7668 | 7.7 |
| 23.919 | 3.7172 | 5.3 |
| 24.500 | 3.6303 | 0.4 |
| 24.876 | 3.5764 | 0 |
| 25.227 | 3.5273 | 0.3 |
| 25.690 | 3.4648 | 30.1 |
| 26.026 | 3.4208 | 5.9 |
| 26.240 | 3.3934 | 2.8 |
| 26.447 | 3.3674 | 2.3 |
| 26.759 | 3.3288 | 5.1 |
| 27.505 | 3.2402 | 1.7 |
| 28.346 | 3.1459 | 6.8 |
| 29.629 | 3.0126 | 3.2 |
| 30.598 | 2.9193 | 6 |
| 31.159 | 2.868 | 2.4 |
| 31.425 | 2.8444 | 1 |
| 31.912 | 2.802 | 2.2 |
| 32.013 | 2.7934 | 2 |
| 33.883 | 2.6434 | 3.3 |
| 34.326 | 2.6103 | 3.4 |
| 34.883 | 2.5699 | 1.9 |

In some preferred embodiments of the present invention, crystal form I has characteristic peaks at the following positions in the XRPD diagram represented by 20 angles are basically as shown in FIG. 1. In the thermogravimetric analysis pattern (TGA) of the crystal form I, the weight loss gradient at 200° C. is 0.15%, and the "%" is the weight percentage, and the TGA pattern is preferably as shown in FIG. 2. In the differential scanning thermal spectrum (DSC) of the crystalline form I, there is a heat absorption peak at 235° C., and the DSC spectrum is preferably as shown in FIG. 3. The dynamic moisture adsorption spectrum (DVS) of the crystal form I is shown in FIG. 4. In the polarized light microscope picture of the crystal form I, the crystal form presents flaky crystals, and the polarized light microscope picture is preferably basically as shown in FIG. 5.

The present invention provides a crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, The crystal form of the salt formed by the 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide and acid. The acid may be a pharmaceutically acceptable acid or a common acid in the art, or an inorganic acid. Or organic acid. The inorganic acid is preferably hydrochloric acid, sulfuric acid or phosphoric acid, more preferably hydrochloric acid. The organic acid is preferably hydrobromic acid, methanesulfonic acid, p-tolu-enesulfonic acid, maleic acid, L-tartaric acid, fumaric acid, citric acid, malic acid or succinic acid, more preferably hydrobromic acid, fumaric acid or Citric acid is more preferably fumaric acid.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide fumarate crystal form II, which has characteristic peaks at the following positions in the XRPD diagram represented by 20 angles: 11.817±0.2°、13.984±0.2°、15.434±0.2°、17.853±0.2°、18.89±0.2°、19.825±0.2°、21.718±0.2°;

or characteristic peaks at 4.461±0.2°、11.817±0.2°、13.251±0.2°、13.984±0.2°、15.434±0.2°、16.78±0.2°、17.853±0.2°、18.89±0.2°、19.825±0.2°、21.718±0.2°、22.056±0.2°、24.652±0.2°、25.198±0.2°、26.762±0.2°;

or characteristic peaks at 4.461±0.2°、8.904±0.2°、11.817±0.2°、12.244±0.2°、13.251±0.2°、13.6±0.2°、13.984±0.2°、15.434±0.2°、15.9±0.2°、16.78±0.2°、17.154±0.2°、17.853±0.2°、18.89±0.2°、19.825±0.2°、20.926±0.2°、21.718±0.2°、22.056±0.2°、22.656±0.2°、24.35±0.2°、24.652±0.2°、25.198±0.2°、25.88±0.2°、26.301±0.2°、26.762±0.2°、27.836±0.2°、28.179±0.2°.

In some preferred embodiments of the present invention, the crystal form II has characteristic peaks at the following positions in the XRPD diagram represented by 20 angles, as shown in the Table 2 below;

TABLE 2

| Diffraction angle (2θ°) | Relative Strength (%) | d value (Å) |
|---|---|---|
| 4.461 | 41.4 | 19.79333 |
| 8.904 | 20.0 | 9.924 |
| 11.817 | 80.6 | 7.48317 |
| 12.244 | 24.3 | 7.22324 |
| 13.251 | 45.8 | 6.67645 |
| 13.6 | 34.1 | 6.50553 |
| 13.984 | 50.6 | 6.32792 |
| 15.434 | 71.2 | 5.73649 |
| 15.9 | 19.9 | 5.56949 |
| 16.78 | 44.1 | 5.27934 |
| 17.154 | 36.3 | 5.16509 |
| 17.853 | 100 | 4.96424 |
| 18.89 | 50.3 | 4.69408 |
| 19.825 | 50.5 | 4.47468 |
| 20.926 | 28.2 | 4.24173 |
| 21.718 | 54.2 | 4.08883 |
| 22.056 | 42.5 | 4.02688 |
| 22.656 | 23.5 | 3.92152 |
| 23.282 | 14.7 | 3.81762 |
| 23.732 | 17.5 | 3.74614 |
| 24.35 | 27.1 | 3.6525 |
| 24.652 | 48.1 | 3.60846 |
| 25.198 | 48.2 | 3.5315 |
| 25.88 | 25.7 | 3.43995 |
| 26.301 | 26.8 | 3.38583 |
| 26.762 | 45.4 | 3.32852 |
| 27.836 | 23.0 | 3.20251 |
| 28.179 | 22.6 | 3.16424 |
| 28.65 | 11.2 | 3.11328 |
| 29.855 | 12.1 | 2.99033 |
| 30.494 | 14.1 | 2.92915 |
| 30.607 | 15.3 | 2.91859 |
| 31.677 | 13.5 | 2.82236 |
| 32.656 | 11.7 | 2.73999 |
| 36.767 | 10.8 | 2.44247 |
| 37.328 | 10.1 | 2.40703 |
| 37.984 | 8.8 | 2.367 |

TABLE 2-continued

| Diffraction angle (2θ°) | Relative Strength (%) | d value (Å) |
|---|---|---|
| 38.408 | 10.1 | 2.34181 |
| 39.149 | 10.1 | 2.29918 |

In some preferred embodiments of the present invention, crystal form II has characteristic peaks at the following positions in the XRPD diagram represented by 20 angles are basically as shown in FIG. 6. In the TGA pattern of the crystal form II, the weight loss gradient at 200° C. is 0.31%, and the "%" is the weight percentage, and the TGA pattern is shown in FIG. 7. In the DSC spectrum of the crystal form II, there is a heat absorption peak at 251° C., and the DSC spectrum is preferably as shown in FIG. 8. This peak should be the melting peak of the sample and decompose immediately after melting. In the DVS pattern of the crystal form II, the moisture absorption at 90% relative humidity (RH) is 1.66%, the XRPD pattern of the sample has not changed, and the DVS pattern is preferably as shown in FIG. 9. It is known that fumarate has better solid form and properties. In the polarized light microscope picture of the crystal form II, the crystal form presents granular crystals, and the polarized light microscope picture is preferably as shown in FIG. 10.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide mono-hydrochloride Crystal form III, which has characteristic peaks at the following positions in the XRPD diagram represented by 2θ angles: 5.397±0.2°、8.270±0.2°、10.703±0.2°、13.561±0.2θ、16.097±0.2°、16.374±0.2°、19.460±0.2°、20.501±0.2°、21.041±0.2°、21.514±0.2°、22.298±0.2°、22.601±0.2°、23.615±0.2°、23.828±0.2°、26.440±0.2°.

In some preferred embodiments of the present invention, the crystal form III has characteristic peaks at the following positions in the XRPD diagram represented by 2θ angles, as shown in the Table 3 below;

TABLE 3

| Diffraction angle (2θ°) | Relative Strength (%) | d value (Å) |
|---|---|---|
| 5.397 | 100 | 16.36285 |
| 8.270 | 20.6 | 10.68294 |
| 10.703 | 29.8 | 8.25938 |
| 11.213 | 10.5 | 7.88469 |
| 13.561 | 20.1 | 6.5241 |
| 13.861 | 11.4 | 6.38369 |
| 15.270 | 10.1 | 5.79766 |
| 15.635 | 19.6 | 5.66331 |
| 16.097 | 22.9 | 5.50165 |
| 16.374 | 21.4 | 5.40916 |
| 16.938 | 17.3 | 5.23026 |
| 18.411 | 12.5 | 4.81501 |
| 18.860 | 11.8 | 4.70146 |
| 19.460 | 20.7 | 4.55792 |
| 20.501 | 21.7 | 4.32873 |
| 21.041 | 61.3 | 4.21873 |
| 21.514 | 26.8 | 4.12717 |
| 22.298 | 28.4 | 3.98365 |
| 22.601 | 21.6 | 3.93096 |
| 23.615 | 41.7 | 3.76449 |
| 23.828 | 40.3 | 3.73127 |
| 24.861 | 12.5 | 3.57858 |
| 25.310 | 17.8 | 3.51603 |
| 26.440 | 72.6 | 3.36833 |

TABLE 3-continued

| Diffraction angle (2θ°) | Relative Strength (%) | d value (Å) |
|---|---|---|
| 26.871 | 16.8 | 3.31527 |
| 27.924 | 17.6 | 3.19254 |
| 28.767 | 12.0 | 3.10089 |
| 29.837 | 6.7 | 2.99214 |
| 30.560 | 10.0 | 2.92293 |
| 31.016 | 12.7 | 2.88104 |
| 32.066 | 6.9 | 2.78902 |
| 33.556 | 12.6 | 2.66846 |
| 34.280 | 7.0 | 2.61376 |
| 36.069 | 5.1 | 2.48816 |
| 37.291 | 6.9 | 2.40937 |
| 38.063 | 6.8 | 2.36224 |
| 38.726 | 6.0 | 2.32331 |

In some preferred embodiments of the present invention, crystal form III has characteristic peaks at the following positions in the XRPD diagram represented by 2θ angles are basically as shown in FIG. 11. In the TGA pattern of the crystal form III, the weight loss gradient at 125° C. is 30.07%, and the "%" is a percentage by weight, and the TGA pattern is preferably as shown in FIG. 12. In the DSC spectrum of the crystal form III, there are heat absorption peaks at 128° C. and 202° C., and the DSC spectrum is preferably as shown in FIG. 13.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide dihydrochloride Crystal form IV, which has characteristic peaks at the following positions in the XRPD diagram represented by 2θ angles: 4.293±0.2°、 5.147±0.2°、 6.242±0.2°、 9.021±0.2°、 10.709±0.2°、 11.898±0.2°、 12.896±0.2°、 14.333±0.2°、 14.650±0.2°、 15.648±0.2°、 16.629±0.2°、 16.797±0.2°、 17.224±0.2°、 18.501±0.2°、 19.024±0.2°、 21.692±0.2°、 25.508±0.2°.

In some preferred embodiments of the present invention, the crystal form IV has characteristic peaks at the following positions in the XRPD diagram represented by 2θ angles, as shown in the Table 4 below;

TABLE 4

| Diffraction angle (2θ°) | Relative Strength (%) | d value (Å) |
|---|---|---|
| 4.293 | 100 | 20.56553 |
| 5.147 | 79.2 | 17.15621 |
| 6.242 | 87.4 | 14.14906 |
| 9.021 | 41.5 | 9.79522 |
| 10.709 | 47.3 | 8.25469 |
| 11.898 | 62.1 | 7.43193 |
| 12.896 | 83.3 | 6.85926 |
| 14.333 | 65.5 | 6.17468 |
| 14.650 | 61.5 | 6.04155 |
| 15.648 | 47.5 | 5.65838 |
| 16.629 | 56.3 | 5.3268 |
| 16.797 | 58.5 | 5.27394 |
| 17.224 | 79.7 | 5.14416 |
| 18.501 | 48.8 | 4.79187 |
| 19.024 | 49.3 | 4.66139 |
| 21.692 | 61.0 | 4.09373 |
| 25.508 | 79.4 | 3.48917 |
| 28.342 | 45.4 | 3.14644 |
| 29.629 | 36.6 | 3.01267 |

In some preferred embodiments of the present invention, crystal form IV has characteristic peaks at the following positions in the XRPD diagram represented by 2θ angles are basically as shown in FIG. 14. In the TGA pattern of the crystalline form IV, the weight loss gradient at 114° C. is 0.82%, the weight loss gradient at 215° C. is 3.68%, and the "%" is the weight percentage. The TGA pattern is preferably as shown in FIG. 15. In the DSC spectrum of the crystal form IV, there is a heat absorption peak at 205° C., and the DSC spectrum is preferably as shown in FIG. 16.

The present invention provides a 3-((1H-pyrazolo[3,4-b] pyridin-5-yl)ethynyl)-4-methyl-N-(4-((4-use methylpiperazine-1-yl)methyl)-3-(trifluoromethyl) phenyl) benzamide hydrobromide Crystal form V, which has characteristic peaks at the following positions in the XRPD diagram represented by 2θ angles: 3.177±0.2°、 5.370±0.2°、 10.658±0.2°、 12.667±0.2°、 17.429±0.2°、 18.333±0.2°、 21.671±0.2°、 22.216±0.2°、 22.515±0.2°、 23.466±0.2°、 24.716±0.2°、 24.976±0.2°、 25.216±0.2°、 26.68±0.2°、 27.728±0.2°.

In some preferred embodiments of the present invention, the crystal form V has characteristic peaks at the following positions in the XRPD diagram represented by 2θ angles, as shown in the Table 5 below;

TABLE 5

| Diffraction angle (2θ°) | Relative Strength (%) | d value (Å) |
|---|---|---|
| 3.177 | 34.4 | 27.78533 |
| 5.370 | 100 | 16.44447 |
| 7.129 | 17.3 | 12.38924 |
| 9.178 | 12.4 | 9.62791 |
| 10.658 | 24.6 | 8.29376 |
| 12.667 | 23.5 | 6.9827 |
| 13.247 | 16.4 | 6.6782 |
| 14.087 | 9.6 | 6.28208 |
| 14.401 | 9.8 | 6.14575 |
| 15.061 | 18.6 | 5.87766 |
| 15.539 | 17.5 | 5.69814 |
| 15.987 | 16.4 | 5.53938 |
| 17.429 | 72.7 | 5.08422 |
| 17.752 | 15.7 | 4.99227 |
| 18.333 | 22.5 | 4.83533 |
| 20.394 | 10.5 | 4.35116 |
| 20.712 | 11.9 | 4.28499 |
| 21.213 | 15.9 | 4.18499 |
| 21.671 | 23.1 | 4.09763 |
| 22.216 | 37.5 | 3.99834 |
| 22.515 | 46.8 | 3.9458 |
| 23.466 | 40.0 | 3.788 |
| 24.716 | 30.5 | 3.59926 |
| 24.976 | 36.9 | 3.56231 |
| 25.216 | 29.8 | 3.5289 |
| 25.67 | 12.6 | 3.46751 |
| 26.418 | 17.8 | 3.37108 |
| 26.68 | 35.1 | 3.33853 |
| 27.238 | 16.7 | 3.27141 |
| 27.728 | 25.9 | 3.21471 |
| 29.07 | 13.1 | 3.06929 |
| 30.003 | 18.0 | 2.97595 |
| 30.389 | 14.9 | 2.93896 |
| 32.131 | 8.7 | 2.78351 |
| 32.454 | 12.9 | 2.75655 |
| 32.85 | 16.1 | 2.72422 |
| 33.248 | 9.1 | 2.69251 |
| 33.687 | 8.6 | 2.65839 |
| 36.578 | 10.5 | 2.45468 |
| 38.049 | 10.7 | 2.36309 |
| 39.096 | 10.9 | 2.30216 |

In some preferred embodiments of the present invention, crystal form V has characteristic peaks at the following positions in the XRPD diagram represented by 2θ angles are basically as shown in FIG. 17. In the TGA pattern of the crystal form V, the weight loss gradient at 262° C. is 3.10%, and the "%" is the weight percentage, and the TGA pattern is preferably as shown in FIG. 18. In the DSC spectrum of the crystal form V, there is a broad absorption peak at 220° C., and the DSC spectrum is preferably as shown in FIG. 19.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide Sulfate Crystal form VI, which has characteristic peaks at the following positions in the XRPD diagram represented by 2θ angles: 4.365±0.2°、 8.031±0.2°、 8.309±0.2°、 10.357±0.2°、 13.036±0.2°、 13.548±0.2°、 14.566±0.2°、 15.323±0.2°、 15.518±0.2°、 16.055±0.2°、 16.70±0.2°、 17.463±0.2°、 18.292±0.2°、 18.872±0.2°、 19.114±0.2°、 19.621±0.2°、 19.970±0.2°、 20.762±0.2°、 21.253±0.2°、 22.358±0.2°、 23.251±0.2°、 24.272±0.2°、 24.646±0.2°、 25.050±0.2°、 25.474±0.2°、 26.292±0.2°、 26.727±0.2°.

In some preferred embodiments of the present invention, the crystal form VI has characteristic peaks at the following positions in the XRPD diagram represented by 2θ angles, as shown in the Table 6 below;

TABLE 6

| Diffraction angle (2θ°) | Relative Strength (%) | d value (Å) |
|---|---|---|
| 4.365 | 91.9 | 20.22792 |
| 8.031 | 25.8 | 10.99964 |
| 8.309 | 38.8 | 10.63289 |
| 10.357 | 100 | 8.53397 |
| 12.253 | 18.7 | 7.21787 |
| 13.036 | 39.2 | 6.78585 |
| 13.548 | 28.2 | 6.53064 |
| 13.899 | 17.5 | 6.36631 |
| 14.566 | 40.3 | 6.07637 |
| 15.323 | 22.8 | 5.77783 |
| 15.518 | 27.2 | 5.70574 |
| 16.055 | 29.7 | 5.51602 |
| 16.70 | 29.4 | 5.30436 |
| 17.463 | 49.6 | 5.07421 |
| 18.292 | 36.8 | 4.84621 |
| 18.872 | 25.8 | 4.69845 |
| 19.114 | 30.7 | 4.6396 |
| 19.621 | 26.3 | 4.52083 |
| 19.970 | 33.9 | 4.44257 |
| 20.762 | 25.9 | 4.27493 |
| 21.253 | 47.7 | 4.17725 |
| 22.358 | 29.4 | 3.97315 |
| 23.251 | 27.9 | 3.82251 |
| 24.272 | 32.1 | 3.66405 |
| 24.646 | 37.3 | 3.60933 |
| 25.050 | 29.7 | 3.55196 |
| 25.474 | 26.8 | 3.49378 |
| 26.292 | 24.9 | 3.3869 |
| 26.727 | 24.2 | 3.33284 |
| 29.136 | 14.8 | 3.06248 |

In some preferred embodiments of the present invention, crystal form VI has characteristic peaks at the following positions in the XRPD diagram represented by 2θ angles are basically as shown in FIG. 20. In the TGA spectrum of the crystalline form VI, there is a 3.42% weight loss at 100° C. and a 1.25% weight loss at 200° C. The "%" is a weight percentage. The TGA spectrum is preferably as shown in FIG. 21. In the DSC spectrum of the crystal form VI, there are heat absorption peaks at 100° C. and 161° C., and the DSC spectrum is preferably as shown in FIG. 22.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide Phosphate Crystal form VII, which has characteristic peaks at the following positions in the XRPD diagram represented by 2θ angles: 3.178±0.2°、 8.510±0.2°、 10.637±0.2°、 12.741±0.2°、 14.097±0.2°、

8

14.471±0.2°、 15.144±0.2°、 17.056±0.2°、 19.043±0.2°、 23.974±0.2°、 26.785±0.2°.

In some preferred embodiments of the present invention, the crystal form VII has characteristic peaks at the following positions in the XRPD diagram represented by 2θ angles, As shown in the Table 7 below;

TABLE 7

| Diffraction angle (2θ°) | Relative Strength (%) | d value (Å) |
|---|---|---|
| 3.178 | 39.6 | 27.78238 |
| 7.206 | 18.6 | 12.25751 |
| 8.510 | 32.1 | 10.38204 |
| 9.560 | 9.1 | 9.24387 |
| 10.637 | 49.8 | 8.31024 |
| 12.741 | 40.3 | 6.94248 |
| 13.197 | 12.5 | 6.70324 |
| 13.606 | 26.8 | 6.50306 |
| 14.097 | 29.9 | 6.27738 |
| 14.471 | 43.6 | 6.11586 |
| 15.144 | 55.3 | 5.84562 |
| 15.939 | 7.9 | 5.55582 |
| 16.52 | 19.7 | 5.36179 |
| 17.056 | 46.5 | 5.19455 |
| 17.543 | 17.2 | 5.05133 |
| 17.904 | 10.7 | 4.95039 |
| 19.043 | 100 | 4.65668 |
| 20.245 | 14.9 | 4.38286 |
| 20.982 | 11.0 | 4.23055 |
| 21.307 | 25.1 | 4.16667 |
| 21.984 | 22.8 | 4.03998 |
| 22.657 | 12.1 | 3.92143 |
| 23.148 | 12.0 | 3.83928 |
| 23.974 | 94.4 | 3.70886 |
| 24.848 | 14.0 | 3.58037 |
| 25.784 | 21.5 | 3.45248 |
| 26.785 | 43.0 | 3.32569 |
| 27.756 | 13.8 | 3.21154 |
| 28.211 | 10.3 | 3.16072 |
| 28.593 | 9.8 | 3.11936 |
| 29.726 | 11.6 | 3.00301 |
| 30.498 | 10.7 | 2.92878 |
| 32.317 | 7.1 | 2.76793 |
| 33.603 | 6.8 | 2.66486 |
| 36.459 | 5.4 | 2.46243 |
| 37.825 | 5.8 | 2.37656 |

In some preferred embodiments of the present invention, crystal form VII has characteristic peaks at the following positions in the XRPD diagram represented by 2θ angles are basically as shown in FIG. 23. In the TGA pattern of the crystal form VII, the weight loss gradient at 200° C. is about 0.08%, and the "0%" is a weight percentage, and the TGA pattern is preferably as shown in FIG. 24. In the DSC spectrum of the crystal form VII, there is a melting peak at 223° C., and the DSC spectrum is preferably as shown in FIG. 25.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide Citrate Crystal form VIII, which has characteristic peaks at the following positions in the XRPD diagram represented by 2θ angles: 4.455±0.2°、 8.297±0.2°、 12.856±0.2°、 13.307±0.2°.

In some preferred embodiments of the present invention, the crystal form VIII has characteristic peaks at the following positions in the XRPD diagram represented by 2θ angles, as shown in the Table 8 below;

TABLE 8

| Diffraction angle (2θ°) | Relative Strength (%) | d value (Å) |
|---|---|---|
| 4.455 | 100 | 19.82056 |
| 6.694 | 8.9 | 13.19358 |
| 8.297 | 27.1 | 10.64757 |
| 8.60 | 16.7 | 10.27356 |
| 8.883 | 15.5 | 9.94707 |
| 10.036 | 8.6 | 8.80676 |
| 10.886 | 13.7 | 8.12114 |
| 11.743 | 13.5 | 7.52999 |
| 12.138 | 16.0 | 7.28565 |
| 12.856 | 33.8 | 6.88041 |
| 13.307 | 54.0 | 6.64819 |
| 14.614 | 18.7 | 6.05634 |
| 15.126 | 12.3 | 5.85277 |
| 15.481 | 10.2 | 5.71922 |
| 16.296 | 11.8 | 5.43481 |
| 16.588 | 11.5 | 5.3398 |
| 17.172 | 18.7 | 5.15969 |
| 17.892 | 17.4 | 4.95363 |
| 19.163 | 13.0 | 4.6279 |
| 20.008 | 16.6 | 4.43414 |
| 21.651 | 13.5 | 4.10127 |
| 22.517 | 9.4 | 3.9455 |
| 25.90 | 8.3 | 3.43736 |
| 26.436 | 10.5 | 3.36882 |
| 27.76 | 7.8 | 3.21102 |
| 29.377 | 5.0 | 3.0379 |

In some preferred embodiments of the present invention, crystal form VIII has characteristic peaks at the following positions in the XRPD diagram represented by 2θ angles are basically as shown in FIG. 26. In the TGA pattern of the crystal form VIII, the weight loss gradient at 125° C. is 1.46%, and the "%" is a weight percentage, and the TGA pattern is preferably as shown in FIG. 27. In the DSC spectrum of the crystal form VIII, there is a heat absorption peak at 153° C., and the DSC spectrum is preferably as shown in FIG. 28.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide L-tartrate Crystal form IX, which has characteristic peaks at the following positions in the XRPD diagram represented by 2θ angles: 3.591±0.2°、7.250±0.2°、11.462±0.2°、13.734±0.2°、14.019±0.2°、14.485±0.2°、15.124±0.2°、17.727±0.2°、18.080±0.2°、19.438±0.2°、19.674±0.2°、20.18±0.2°、20.745±0.2°、22.956±0.2°、23.532±0.2°、24.255±0.2°、25.963±0.2°.

In some preferred embodiments of the present invention, the crystal form IX has characteristic peaks at the following positions in the XRPD diagram represented by 2θ angles, as shown in the Table 9 below;

TABLE 9

| Diffraction angle (2θ°) | Relative Strength (%) | d value (Å) |
|---|---|---|
| 3.591 | 35.2 | 24.58583 |
| 6.579 | 15.8 | 13.42473 |
| 7.250 | 32.8 | 12.1835 |
| 8.85 | 14.6 | 9.98418 |
| 9.582 | 14.6 | 9.2228 |
| 11.462 | 36.4 | 7.71413 |
| 12.787 | 15.4 | 6.91767 |
| 13.734 | 49.3 | 6.44235 |
| 14.019 | 90.5 | 6.31208 |
| 14.485 | 88.1 | 6.11005 |
| 15.124 | 47.5 | 5.85328 |
| 15.797 | 25.5 | 5.60555 |

TABLE 9-continued

| Diffraction angle (2θ°) | Relative Strength (%) | d value (Å) |
|---|---|---|
| 17.083 | 41.5 | 5.18636 |
| 17.727 | 68.7 | 4.99923 |
| 18.080 | 100 | 4.90253 |
| 19.111 | 25.9 | 4.64032 |
| 19.438 | 41.3 | 4.56292 |
| 19.674 | 56.9 | 4.50876 |
| 20.180 | 76.3 | 4.39678 |
| 20.745 | 40.1 | 4.27835 |
| 21.772 | 28.4 | 4.0788 |
| 22.956 | 62.8 | 3.87099 |
| 23.532 | 37.3 | 3.77754 |
| 24.255 | 31.3 | 3.66659 |
| 25.963 | 76.5 | 3.42913 |
| 26.649 | 26.0 | 3.34235 |
| 27.735 | 19.6 | 3.21389 |
| 28.171 | 25.7 | 3.16512 |
| 29.15 | 29.9 | 3.06102 |
| 30.556 | 15.0 | 2.92327 |
| 32.135 | 14.3 | 2.78316 |
| 33.007 | 10.7 | 2.71159 |
| 35.831 | 14.5 | 2.50411 |
| 36.646 | 11.7 | 2.45025 |

In some preferred embodiments of the present invention, crystal form IX has characteristic peaks at the following positions in the XRPD diagram represented by 2θ angles are basically as shown in FIG. 29. In the TGA spectrum of the crystal form IX, there is a weight loss gradient of 3.36% at 150° C., and the "%" is a weight percentage, and the TGA spectrum is preferably as shown in FIG. 30. In the DSC spectrum of the crystal form IX, there is a broad heat absorption peak at 126° C., and the DSC spectrum is preferably as shown in FIG. 31.

The present invention provides a 3-((1H-pyrazolo[3,4-b] pyridin-5-yl)ethynyl)-4-methyl-N-(4-((4-Text methylpiperazine-1-yl)methyl)-3-(trifluoromethyl) phenyl) benzamide methanesulfonate Crystal form X, use which has characteristic peaks at the following positions in the XRPD diagram represented by 2θ angles: 3.253±0.2°、7.350±0.2°、12.984±0.2°、14.329±0.2°、14.682±0.2°、16.221±0.2°、17.60±0.2°、19.378±0.2、19.567±0.2°、20.055±0.2°、22.721±0.2°、23.978±0.2°、25.515±0.2°.

In some preferred embodiments of the present invention, the crystal form X has characteristic peaks at the following positions in the XRPD diagram represented by 2θ angles, as shown in the Table 10 below;

TABLE 10

| Diffraction angle (2θ°) | Relative Strength (%) | d value (Å) |
|---|---|---|
| 3.253 | 40.2 | 27.1423 |
| 7.350 | 43.6 | 12.01757 |
| 12.542 | 14.9 | 7.05189 |
| 12.984 | 32.2 | 6.81312 |
| 13.422 | 28.0 | 6.59174 |
| 13.785 | 24.4 | 6.41878 |
| 14.329 | 100 | 6.17629 |
| 14.682 | 38.9 | 6.0284 |
| 15.743 | 20.8 | 5.62463 |
| 16.221 | 39.8 | 5.45992 |
| 17.406 | 26.5 | 5.09071 |
| 17.60 | 30.1 | 5.03498 |
| 18.432 | 27.2 | 4.80961 |
| 19.378 | 63.9 | 4.57699 |
| 19.567 | 59.8 | 4.53327 |
| 20.055 | 46.6 | 4.42403 |
| 20.579 | 24.1 | 4.31254 |
| 21.914 | 22.8 | 4.05259 |

TABLE 10-continued

| Diffraction angle (2θ°) | Relative Strength (%) | d value (Å) |
|---|---|---|
| 22.721 | 40.1 | 3.91046 |
| 23.978 | 42.4 | 3.70822 |
| 25.515 | 87.9 | 3.4883 |
| 27.191 | 16.1 | 3.27701 |
| 28.447 | 17.6 | 3.13507 |
| 30.047 | 13.0 | 2.97163 |
| 30.69 | 13.8 | 2.91089 |

In some preferred embodiments of the present invention, crystal form X has characteristic peaks at the following positions in the XRPD diagram represented by 2θ angles are basically as shown in FIG. 32. In the TGA pattern of the crystal form X, the weight loss gradient at 200° C. is 0.28%, and the "%" is a weight percentage, and the TGA pattern is preferably as shown in FIG. 33. In the DSC spectrum of the crystal form X, there is a heat absorption peak at 174° C., and the DSC spectrum is preferably as shown in FIG. 34.

The present invention provides a Solvate crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide, the Solvate crystal form is formed by 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide and solvent. the solvent is preferably ether and/or aromatic solvent, more preferably one or more of tetrahydrofuran, methyl tert-butyl ether and toluene.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide tetrahydrofuran solvate Crystal form XI, which has characteristic peaks at the following positions in the XRPD diagram represented by 2θ angles: 6.411±0.2°、 8.873±0.2°、 9.266±0.2°、 10.402±0.2°、 12.063±0.2°、 12.419±0.2°、 22.336±0.2°.

In some preferred embodiments of the present invention, the crystal form XI has characteristic peaks at the following positions in the XRPD diagram represented by 2θ angles, as shown in the Table 11 below;

TABLE 11

| Diffraction angle (2θ°) | Relative Strength (%) | d value (Å) |
|---|---|---|
| 6.411 | 95.6 | 454 |
| 8.873 | 39.8 | 189 |
| 9.266 | 88.4 | 420 |
| 10.402 | 100 | 475 |
| 12.063 | 41.5 | 197 |
| 12.419 | 30.5 | 145 |
| 12.989 | 26.7 | 127 |
| 14.886 | 17.9 | 85 |
| 15.814 | 28.8 | 137 |
| 17.026 | 29.7 | 141 |
| 17.738 | 21.9 | 104 |
| 18.308 | 15.6 | 74 |
| 18.697 | 16.2 | 77 |
| 19.034 | 15.2 | 72 |
| 19.667 | 14.9 | 71 |
| 20.615 | 14.8 | 70.1 |
| 21.323 | 14.3 | 68 |
| 21.691 | 26.5 | 126 |
| 22.336 | 47.8 | 227 |
| 23.932 | 18.1 | 86 |
| 24.4 | 21.1 | 100 |

TABLE 11-continued

| Diffraction angle (2θ°) | Relative Strength (%) | d value (Å) |
|---|---|---|
| 25.086 | 14.1 | 66.8 |
| 25.568 | 12.0 | 57 |
| 28.243 | 13.5 | 64 |

In some preferred embodiments of the present invention, crystal form XI has characteristic peaks at the following positions in the XRPD diagram represented by 2θ angles are basically as shown in FIG. 35. In the TGA pattern of the crystalline form XI, the weight loss gradient at 173° C. is about 11.52%, the "%" is a weight percentage, and the TGA pattern is preferably as shown in FIG. 36. In the DSC spectrum of the crystal form XI, there are heat absorption peaks at 119° C. and 232° C., and the DSC spectrum is preferably as shown in FIG. 37.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide tetrahydrofuran-methyl tert-butyl ether solvate Crystal form XII, which has characteristic peaks at the following positions in the XRPD diagram represented by 2θ angles: 7.08±0.2°、 8.895±0.2° 和 24.068±0.2°.

In some preferred embodiments of the present invention, the crystal form XII has characteristic peaks at the following positions in the XRPD diagram represented by 2θ angles, as shown in the Table 12 below;

TABLE 12

| Diffraction angle (2θ°) | Relative Strength (%) | d value (Å) |
|---|---|---|
| 7.978 | 100 | 1381 |
| 8.895 | 24.9 | 344 |
| 11.529 | 12.5 | 173 |
| 11.954 | 18.0 | 249 |
| 12.542 | 10.2 | 141 |
| 12.297 | 10.6 | 146 |
| 13.623 | 16.9 | 233 |
| 15.37 | 10.5 | 145 |
| 15.724 | 14.0 | 193 |
| 16.269 | 11.3 | 156 |
| 16.812 | 15.2 | 210 |
| 17.14 | 14.8 | 205 |
| 17.808 | 8.2 | 113 |
| 18.237 | 14.0 | 194 |
| 19.057 | 10.2 | 140 |
| 19.3 | 15.9 | 220 |
| 19.741 | 11.7 | 161 |
| 20.316 | 13.2 | 182 |
| 20.052 | 9.1 | 125 |
| 20.716 | 14.8 | 204 |
| 21.445 | 9.6 | 133 |
| 22.496 | 12.7 | 176 |
| 23.155 | 8.0 | 110 |
| 23.667 | 8.4 | 116 |
| 24.068 | 29.5 | 407 |
| 24.448 | 9.3 | 129 |
| 25.356 | 9.3 | 128 |
| 25.615 | 8.3 | 115 |
| 26.864 | 8.3 | 114 |
| 27.442 | 5.0 | 69 |

In some preferred embodiments of the present invention, crystal form XII has characteristic peaks at the following positions in the XRPD diagram represented by 2θ angles are basically as shown in FIG. 38. In the TGA pattern of the crystalline form XII, the weight loss gradient at 134° C. is about 7.32%, and the weight loss gradient at 180° C. is about 4.30%. The "%" is the weight percentage. The TGA pattern is preferably as shown in FIG. 39. In the DSC spectrum of the crystalline form XII, there are heat absorption peaks at 139° C. and 235° C., and an exothermic peak at 145° C. The DSC spectrum is preferably as shown in FIG. 40.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide toluene solvate Crystal form XIII, which has characteristic peaks at the following positions in the XRPD diagram represented by 2θ angles: 7.224±0.2°、8.0580±2°、13.86±0.2°、19.312±0.2°、21.843±0.2°、24.398±0.2°.

In some preferred embodiments of the present invention, the crystal form XIII has characteristic peaks at the following positions in the XRPD diagram represented by 2θ angles, as shown in the Table 13 below;

TABLE 13

| Diffraction angle (2θ°) | Relative Strength (%) | d value (Å) |
|---|---|---|
| 7.224 | 33.9 | 269 |
| 8.058 | 100 | 793 |
| 9.705 | 24.6 | 195 |
| 11.587 | 26.4 | 209 |
| 13.001 | 18.2 | 144 |
| 13.86 | 32.0 | 254 |
| 14.46 | 20.3 | 161 |
| 14.867 | 23.2 | 184 |
| 15.848 | 29.6 | 235 |
| 16.259 | 17.7 | 140 |
| 18.148 | 13.5 | 107 |
| 19.024 | 26.2 | 208 |
| 19.312 | 38.0 | 301 |
| 20.031 | 15.6 | 124 |
| 20.365 | 15.6 | 124 |
| 20.865 | 15.1 | 120 |
| 21.241 | 14.2 | 113 |
| 21.843 | 68.1 | 540 |
| 22.855 | 12.7 | 101 |
| 24.006 | 24.1 | 191 |
| 24.398 | 45.4 | 360 |
| 25.041 | 12.7 | 101 |
| 26.168 | 15.8 | 125 |
| 27.174 | 12.1 | 96 |
| 28.087 | 9.1 | 71.9 |
| 28.358 | 15.5 | 123 |
| 29.737 | 9.4 | 74.5 |

In some preferred embodiments of the present invention, crystal form XIII has characteristic peaks at the following positions in the XRPD diagram represented by 2θ angles are basically as shown in FIG. 41. In the TGA pattern of the crystalline form XIII, the weight loss gradient at 129° C. is about 7.9200, and the weight loss gradient at 190° C. is about 4.62%. The "0%" is weight percentage, and its TGA pattern is preferably as shown in FIG. 42. In the DSC spectrum of the crystal form XIII, there are heat absorption peaks at 132° C. and 235° C., and the DSC spectrum is preferably as shown in FIG. 43.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide fumarate acetonate Crystal form XIV, the crystal form XIV has characteristic peaks at the following positions in the XRPD diagram represented by 2θ angles, as shown in the Table 14 below;

TABLE 14

| Diffraction angle (2θ°) | d value (Å) | Relative Strength (%) |
|---|---|---|
| 5.993 | 14.7357 | 32.9 |
| 7.101 | 12.4388 | 34.2 |
| 8.541 | 10.3443 | 13.9 |
| 9.552 | 9.2515 | 30.8 |
| 10.248 | 8.6247 | 74.4 |
| 11.957 | 7.3952 | 7.3 |
| 12.874 | 6.8709 | 46.6 |
| 13.361 | 6.6215 | 15.2 |
| 14.138 | 6.2592 | 43.2 |
| 14.988 | 5.9062 | 5.0 |
| 15.34 | 5.7713 | 9.5 |
| 16.004 | 5.5332 | 19.7 |
| 16.643 | 5.3222 | 18.4 |
| 16.993 | 5.2134 | 30.1 |
| 17.905 | 4.9498 | 29.8 |
| 18.451 | 4.8047 | 32.2 |
| 19.169 | 4.6262 | 87.8 |
| 20.142 | 4.4049 | 21.1 |
| 20.453 | 4.3387 | 67.4 |
| 21.288 | 4.1703 | 33.2 |
| 22.063 | 4.0256 | 7.7 |
| 22.901 | 3.8801 | 6.2 |
| 23.54 | 3.7762 | 26.7 |
| 23.891 | 3.7215 | 24.9 |
| 24.494 | 3.6312 | 23.7 |
| 24.999 | 3.559 | 100 |
| 25.815 | 3.4483 | 13.5 |
| 26.149 | 3.405 | 16.3 |
| 26.75 | 3.3299 | 29.8 |
| 27.878 | 3.1977 | 9.7 |
| 28.223 | 3.1593 | 11.6 |
| 28.925 | 3.0842 | 29.4 |
| 29.816 | 2.994 | 4.3 |
| 30.522 | 2.9264 | 6.0 |
| 31.384 | 2.8479 | 4.3 |
| 33.658 | 2.6606 | 5.4 |
| 36.171 | 2.4813 | 3.4 |
| 37.575 | 2.3917 | 5.8 |
| 38.82 | 2.3178 | 6.8 |

In some preferred embodiments of the present invention, crystal form XIV has characteristic peaks at the following positions in the XRPD diagram represented by 2θ angles are basically as shown in FIG. 44. In the TGA profile of the crystalline form XIV, the weight loss gradient at 154° C. is about 6.3200, the weight loss gradient at 198° C. is about 1.57%, and the weight loss gradient at 266° C. is about 12.94%. "%" is a percentage by weight, and its TGA profile is preferably as shown in FIG. 45. In the DSC spectrum of the crystalline form XIV, there are heat absorption peaks at 148° C. and 247° C., and an exothermic peak at 166° C. The DSC spectrum is preferably as shown in FIG. 46.

The present invention provides a 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Mono-hydrochloride Crystal form XV, the crystal form XV has characteristic peaks at the following positions in the XRPD diagram represented by 2θ angles, as shown in the Table 15 below;

TABLE 15

| Diffraction angle (2θ°) | d value (Å) | Relative Strength (%) |
|---|---|---|
| 8.948 | 9.8742 | 15.6 |
| 10.014 | 8.8261 | 4.8 |
| 10.347 | 8.5426 | 9.5 |
| 11.007 | 8.0318 | 3.9 |
| 12.041 | 7.344 | 5.2 |
| 13.395 | 6.6046 | 60.8 |

TABLE 15-continued

| Diffraction angle (2θ°) | d value (Å) | Relative Strength (%) |
|---|---|---|
| 13.923 | 6.3554 | 3.4 |
| 14.722 | 6.0122 | 11.5 |
| 15.4 | 5.7489 | 34.2 |
| 16.661 | 5.3167 | 44.6 |
| 16.971 | 5.2201 | 15.2 |
| 17.263 | 5.1325 | 16.5 |
| 17.828 | 4.971 | 30.2 |
| 19.498 | 4.549 | 14.3 |
| 19.946 | 4.4477 | 20.6 |
| 20.333 | 4.3639 | 16.3 |
| 21.58 | 4.1146 | 18.0 |
| 22.629 | 3.926 | 7.8 |
| 23.931 | 3.7154 | 100 |
| 24.377 | 3.6484 | 34.6 |
| 25.947 | 3.431 | 11.2 |
| 26.479 | 3.3634 | 8.4 |
| 27.14 | 3.283 | 7.2 |
| 27.502 | 3.2405 | 5.5 |
| 29.102 | 3.0659 | 26.5 |
| 31.047 | 2.8781 | 8.2 |
| 32.635 | 2.7416 | 6.7 |
| 38.915 | 2.3124 | 3.7 |

In some preferred embodiments of the present invention, crystal form XV has characteristic peaks at the following positions in the XRPD diagram represented by 2θ angles are basically as shown in FIG. 47. In the TGA pattern of the crystalline form XV, the weight loss gradient at 182° C. is about 0.2900, and the "0%" is a weight percentage, and the TGA pattern is preferably as shown in FIG. 48. In the DSC spectrum of the crystalline form XV, there are heat absorption peaks at 292° C. and 323° C., and an exothermic peak at 298° C. The DSC spectrum is preferably as shown in FIG. 49. The DVS spectrum of the crystal form XV is shown in FIG. 50.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide Dihy-drochloride crystal form XVI, the crystal form XVI has characteristic peaks at the following positions in the XRPD diagram represented by 2θ angles, as shown in the Table 16 below;

TABLE 16

| Diffraction angle (2θ°) | d value (Å) | Relative Strength (%) |
|---|---|---|
| 3.248 | 27.1819 | 47.1 |
| 6.358 | 13.891 | 100 |
| 12.571 | 7.0359 | 5.9 |
| 13.398 | 6.6029 | 9.5 |
| 13.869 | 6.3799 | 20.5 |
| 14.619 | 6.0541 | 11.2 |
| 15.186 | 5.8295 | 15.8 |
| 15.534 | 5.6996 | 16.7 |
| 15.728 | 5.6297 | 23.9 |
| 16.37 | 5.4104 | 17.4 |
| 16.724 | 5.2968 | 14.8 |
| 17.673 | 5.0143 | 18.8 |
| 18.119 | 4.892 | 21.1 |
| 18.371 | 4.8252 | 15.3 |
| 18.893 | 4.6932 | 43.8 |
| 19.246 | 4.6079 | 22.6 |
| 19.791 | 4.4822 | 2.8 |
| 20.398 | 4.3502 | 3.1 |
| 22.027 | 4.0321 | 16.4 |
| 22.728 | 3.9093 | 22.7 |
| 23.05 | 3.8553 | 3.6 |
| 23.442 | 3.7918 | 6.4 |

TABLE 16-continued

| Diffraction angle (2θ°) | d value (Å) | Relative Strength (%) |
|---|---|---|
| 23.544 | 3.7755 | 7.4 |
| 23.892 | 3.7214 | 30.3 |
| 24.438 | 3.6394 | 5.6 |
| 25.214 | 3.5291 | 4.6 |
| 25.642 | 3.4712 | 19.4 |
| 26.203 | 3.3981 | 57.8 |
| 27.329 | 3.2606 | 13.3 |
| 27.78 | 3.2087 | 11.2 |
| 28.458 | 3.1337 | 30.9 |
| 28.804 | 3.0969 | 4.3 |
| 29.482 | 3.0273 | 4.3 |
| 29.936 | 2.9824 | 6.4 |
| 30.232 | 2.9538 | 6.6 |
| 30.621 | 2.9172 | 7.7 |
| 31.335 | 2.8523 | 6.7 |
| 32.073 | 2.7883 | 4.3 |
| 32.417 | 2.7595 | 4.8 |
| 32.772 | 2.7305 | 6.9 |
| 32.985 | 2.7133 | 6.4 |
| 34.625 | 2.5885 | 6.2 |
| 34.989 | 2.5623 | 4.5 |
| 35.962 | 2.4952 | 8 |
| 37.301 | 2.4087 | 3.6 |
| 37.398 | 2.4026 | 4.1 |
| 37.793 | 2.3784 | 5.8 |
| 38.174 | 2.3556 | 9 |

In some preferred embodiments of the present invention, crystal form XVI has characteristic peaks at the following positions in the XRPD diagram represented by 2θ angles are basically as shown in FIG. 51. In the TGA pattern of the crystalline form XVI, the weight loss gradient at 120° C. is about 1.61%, and the weight loss gradient at 212° C. is about 6.23%. The "%" is the weight percentage. The TGA pattern is preferably as shown in FIG. 52. In the DSC spectrum of the crystalline form XVI, there are heat absorption peaks at 224° C. and 323° C., and the DSC spectrum is preferably as shown in FIG. 53.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide Dihy-drochloride crystal form XVII, the crystal form XVII has characteristic peaks at the following positions in the XRPD diagram represented by 2θ angles, as shown in the Table 17 below;

TABLE 17

| Diffraction angle (2θ°) | Relative Strength (%) | d value (Å) |
|---|---|---|
| 7.488 | 11.797 | 28.8 |
| 11.514 | 7.6793 | 41.3 |
| 12.562 | 7.0409 | 4.1 |
| 13.319 | 6.6423 | 23.3 |
| 13.611 | 6.5003 | 23.4 |
| 14.599 | 6.0626 | 8.9 |
| 14.88 | 5.9486 | 3.4 |
| 15.285 | 5.7919 | 5.1 |
| 16.469 | 5.3782 | 53.8 |
| 17.461 | 5.0748 | 5.7 |
| 18.042 | 4.9125 | 18.3 |
| 18.607 | 4.7647 | 22.3 |
| 20.53 | 4.3226 | 13.9 |
| 21.307 | 4.1666 | 21.0 |
| 21.675 | 4.0967 | 12.3 |
| 22.084 | 4.0217 | 49.3 |
| 22.319 | 3.9799 | 23.0 |
| 23.115 | 3.8447 | 71.4 |

TABLE 17-continued

| Diffraction angle (2θ°) | Relative Strength (%) | d value (Å) |
|---|---|---|
| 24.688 | 3.6031 | 100 |
| 25.001 | 3.5587 | 82.2 |
| 25.74 | 3.4582 | 35.4 |
| 26.536 | 3.3562 | 15.9 |
| 26.904 | 3.3112 | 22.1 |
| 27.354 | 3.2577 | 3.1 |
| 27.858 | 3.1999 | 7.2 |
| 28.245 | 3.1569 | 6.5 |
| 29.062 | 3.07 | 23.2 |
| 29.975 | 2.9785 | 7.9 |
| 30.578 | 2.9212 | 31.0 |
| 31.082 | 2.8749 | 8.9 |
| 31.705 | 2.8199 | 5.3 |
| 32.01 | 2.7937 | 3.3 |
| 33.433 | 2.678 | 8.0 |
| 33.761 | 2.6527 | 5.8 |
| 34.603 | 2.5901 | 4.6 |
| 35.068 | 2.5568 | 9.7 |
| 37.881 | 2.3731 | 3.5 |
| 38.488 | 2.337 | 5.0 |

In some preferred embodiments of the present invention, crystal form XVII has characteristic peaks at the following positions in the XRPD diagram represented by 2θ angles are basically as shown in FIG. 54. In the TGA pattern of the crystalline form XVII, the weight loss gradient at 120° C. is about 0.19%, and the weight loss gradient at 265° C. is about 6.17%. The "%" is weight percentage, and its TGA pattern is preferably as shown in the FIG. 55. In the DSC spectrum of the crystal form XVII, there are heat absorption peaks at 258° C. and 339° C., and the DSC spectrum is preferably as shown in FIG. 56.

The present invention provides a 3-((1H-pyrazolo[3,4-b] pyridin-5-yl)ethynyl)-4-methyl-N-(4-((4-methylpiperazine-1-yl)methyl)-3-(trifluoromethyl) phenyl) benzamide citrate crystal form XVIII, the crystal form XVIII has characteristic peaks at the following positions in the XRPD diagram represented by 2θ angles, as shown in the Table 18 below;

TABLE 18

| Diffraction angle (2θ°) | Relative Strength (%) | d value (Å) |
|---|---|---|
| 6.151 | 14.356 | 11.4 |
| 10.4 | 8.4989 | 4.0 |
| 11.708 | 7.5521 | 17.8 |
| 12.215 | 7.2399 | 6.2 |
| 12.892 | 6.8609 | 21.6 |
| 13.492 | 6.5575 | 12.9 |
| 13.86 | 6.384 | 11.5 |
| 14.371 | 6.1581 | 9.5 |
| 14.859 | 5.9572 | 1.7 |
| 15.692 | 5.6426 | 61.3 |
| 16.198 | 5.4676 | 12.3 |
| 16.7 | 5.3041 | 20.8 |
| 17.244 | 5.1381 | 47.3 |
| 17.826 | 4.9717 | 8.9 |
| 18.393 | 4.8198 | 32.6 |
| 18.973 | 4.6737 | 52.0 |
| 19.345 | 4.5846 | 100 |
| 19.677 | 4.508 | 54.1 |
| 20.061 | 4.4224 | 5.0 |
| 20.61 | 4.3059 | 12.6 |
| 20.917 | 4.2435 | 19.4 |
| 21.6 | 4.1107 | 69.5 |
| 22.143 | 4.0111 | 7.8 |
| 22.476 | 3.9525 | 4.9 |
| 22.805 | 3.8962 | 6.2 |

TABLE 18-continued

| Diffraction angle (2θ°) | Relative Strength (%) | d value (Å) |
|---|---|---|
| 23.017 | 3.8608 | 12.9 |
| 23.522 | 3.779 | 16.8 |
| 24.09 | 3.6912 | 12.1 |
| 24.397 | 3.6455 | 13.4 |
| 24.996 | 3.5594 | 8.2 |
| 25.583 | 3.4791 | 35.0 |
| 25.875 | 3.4404 | 22.5 |
| 26.205 | 3.3979 | 20.5 |
| 26.808 | 3.3228 | 6.3 |
| 27.439 | 3.2478 | 5.1 |
| 28.809 | 3.0964 | 16.4 |
| 29.37 | 3.0386 | 11.4 |
| 30.287 | 2.9486 | 3.6 |
| 30.776 | 2.9028 | 3.7 |
| 31.276 | 2.8575 | 13.6 |
| 31.512 | 2.8367 | 7.1 |
| 32.248 | 2.7736 | 7.8 |
| 32.911 | 2.7193 | 4.7 |
| 33.314 | 2.6872 | 3.3 |
| 33.555 | 2.6685 | 5.6 |
| 34.056 | 2.6304 | 3.6 |
| 34.405 | 2.6045 | 6.6 |
| 34.641 | 2.5873 | 3.1 |
| 35.239 | 2.5447 | 3.0 |
| 35.727 | 2.5111 | 4.7 |
| 37.052 | 2.4243 | 6.6 |
| 39.054 | 2.3045 | 5.9 |

In some preferred embodiments of the present invention, crystal form XVIII has characteristic peaks at the following positions in the XRPD diagram represented by 2θ angles are basically as shown in FIG. 57. In the TGA pattern of the crystalline form XVIII, the weight loss gradient at 165° C. is about 0.49%, and the weight loss gradient at 250° C. is about 22.89%. The "%" is the weight percentage. The TGA pattern is preferably shown in the FIG. 58. In the DSC spectrum of the crystalline form XVIII, there is a heat absorption peak at 192° C., and the DSC spectrum is preferably as shown in FIG. 59.

In the present invention, the rays used in the X-ray powder diffraction are Kα rays.

In the present invention, the target type used in the X-ray powder diffraction is a Cu target.

The present invention also provides a method for preparing compound crystal form I, which comprises the following steps: 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide is crystallized in an organic solvent, the organic solvent is one or more of C1-C10 alkane, C1-C4 alcohol, ether, nitrile, ketone, ester and DMSO.

In the preparation method of the crystal form I, the crystallization method can be a well known in the art, such as suspension stirring, room temperature stirring, heating and cooling crystallization, solvent volatilization or anti-solvent addition.

In the preparation method of the crystal form I, the 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide is prepared by referring to the patent method.

In the preparation method of the crystal form I, the organic solvent is One or more of preferably heptane, methanol, ethanol, isopropanol, methyl tert-butyl ether, acetonitrile, acetone, 2-butanone, ethyl acetate, acetic acid isopropyl ester and DMSO.

In the preparation method of the crystal form I, the mass-volume ratio of the 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide to the organic solvent may be a conventional mass-volume ratio in the art, preferably 1:1-1:5 g/mL, more preferably 1:1-1:3 g/mL, such as 1:2.5 g/mL.

In the preparation method of the crystal form I, the crystallization temperature may be a conventional temperature in the art, for example, 20-50° C.

In the preparation method of the crystal form I, there is no special restriction on the crystallization time, as long as the crystals can be precipitated, such as 1-36 h, or 1-5 h, or 1-3 h.

In the preparation method of the crystal form I, when the crystallization adopts the stirring method at room temperature, the organic solvent is preferably One or more of C1-C10 alkane solvents, C1-C4 alcohol solvents, nitriles, and ketones, ether and ester, more preferably one or more of heptane, methanol, ethanol, isopropanol, acetonitrile, acetone, 2-butanone, methyl tert-butyl ether, isopropyl acetate, ethyl acetate.

In the preparation method of the crystal form I, when the anti-solvent addition is used for the crystallization, the organic solvent is preferably DMSO.

In the preparation method of the crystal form I, when the anti-solvent addition is used for the crystallization, the anti-solvent is preferably one or more of water, alcohol and nitrile. The water can be one or more of distilled water, deionized water, purified water, tap water and mineral water. The alcohol is preferably isopropanol. The nitrile is preferably acetonitrile. The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl) phenyl)benzamide and the anti-solvent may be a conventional mass-volume ratio in the art, preferably 1:2-1:25 g/mL, more preferably 1:2-1:20 g/mL, such as 1:2.5 g/mL, 1:7.5 g/mL, or 1:20 g/mL.

The method for preparing the crystal form I, which preferably comprises the following steps: mixing 3-((1H-pyrazolo[3,4-b]pyridin-5-yl)ethynyl)-4-methyl-N-(4-((4-methylpiperazine-1-yl)methyl)-3-(trifluoromethyl)phenyl) benzamide with an organic solvent, stirring, and filtering to obtain the target crystal form; the organic solvent is One or more of C1-C10 alkane, C1-C4 alcohol, nitrile, ketone, ether and ester, preferably One or more of heptane, methanol, ethanol, isopropanol, acetonitrile, acetone, 2-butanone, methyl tert-butyl ether, isopropyl acetate and ethyl acetate. The stirring is preferably carried out at 20-50° C. The stirring is preferably carried out for 1-5 hours. After the filtering is completed, drying is also preferably included. The drying is preferably vacuum drying. The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide to the organic solvent is preferably 1:1-1:5 g/mL.

The method for preparing the crystal form I, which preferably comprises the following steps: Adding 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide to mix with DMSO, anti-solvent was added, and filtered to obtain the target crystal form; The anti-solvent is one or more of water, alcohol and nitrile, preferably one or more of water, isopropanol and acetonitrile. The added amount of the anti-solvent is preferably based on the precipitation of a large amount of solids. The said anti-solvent is preferably added slowly. The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide to the DMSO is preferably 1:1-1:5 g/mL. The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl)phenyl) benzamide to the anti-solvent is preferably 1:2-1:25 g/mL.

The present invention also provides a preparation method of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt crystal form, which comprises the following steps: 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide reacts with acid in an organic solvent, and then crystallizes.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, the crystallization method can be a well-known method in the art, such as suspension stirring, room temperature stirring, heating and cooling crystallization, solvent volatilization or anti-solvent addition.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, the 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide is prepared by referring to a patented method.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, The organic solvent can be a conventional organic solvent in the field, and can also be one or more of alkane, alcohol, ketone, ester, aromatic hydrocarbon solvents, halogenated hydrocarbon solvents, nitrile, ethers, aliphatic hydrocarbon solvents, DMF and DMSO (e.g. C1-C10 alkane, C1-C4 alcohol, acetone, 2-butanone, ethyl acetate, isopropyl acetate, Toluene, dichloromethane, dichloroethane, chloroform, acetonitrile, diethyl ether, methyl tert-butyl ether, tetrahydrofuran, cyclohexane, DMF and DMSO one or more), preferably one or more of alcohol, halogenated hydrocarbon solvents and ether, more preferably one or more of methanol, ethanol, isopropanol, dichloromethane, and tetrahydrofuran.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide to the organic solvent may be a conventional mass-volume ratio in the art, preferably 1:1-1:25 g/mL, more preferably 1:5-1:25 g/mL, such as 1:5 g/mL, 1:10 g/mL, 1:12.5 g/mL, or 1:25 g/mL.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, the acid may be a pharmaceutically acceptable acid or a common acid in the art, and may be an inorganic acid or an organic acid. The inorganic acid is preferably hydrochloric acid, sulfuric acid or phosphoric acid, more preferably hydrochloric acid. The organic acid is preferably hydrobromic acid, methanesulfonic acid, p-toluenesulfonic acid, maleic acid, L-tartaric acid, fumaric acid, citric acid, malic acid or succinic acid, more preferably hydrobromic acid, L-tartaric acid, Fumaric acid or citric acid, more preferably fumaric acid.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, The molar ratio of the acid to 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide can be a conventional molar ratio in the art, preferably 1:0.9-1:3, such as 1:0.9, 1:1, 1:1.05 or 1:2.1.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, The crystallization temperature can be a conventional temperature in the art, for example, 20-60° C.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, There is no special restriction on the crystallization time, as long as the crystals can be precipitated, such as 1-36 h, or 1-5 h.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, When the anti-solvent addition is used for the crystallization, the anti-solvent is preferably an ester solvent, and more preferably ethyl acetate. There is no special restriction on the mass-volume ratio of the compound and the anti-solvent, as long as it does not affect the precipitation of crystals.

In the method for preparing the crystalline form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide salt, which preferably comprises the following steps: Mixing 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide with an organic solvent, adding acid, and filtering to obtain the target crystal form. The organic solvent is preferably one or more of alcohol, halogenated hydrocarbon solvents and ether, more preferably one or more of methanol, ethanol, isopropanol, dichloromethane and tetrahydrofuran. The acid is preferably hydrochloric acid, sulfuric acid, phosphoric acid, hydrobromic acid, L-tartaric acid, fumaric acid or citric acid, and more preferably fumaric acid. the mixing and adding acid are preferably carried out under stirring. After the filtering is completed, drying is preferably included. The drying is preferably vacuum drying, and the drying temperature is preferably 40-60° C., for example, 50° C.

The present invention also provides a method for preparing the crystal form of 3-((1H-pyrazolo[3,4-b]pyridin-5-yl) ethynyl)-4-methyl-N-(4-((4-methylpiperazine-1-yl)methyl)-3-(trifluoromethyl) phenyl) benzamide solvate, which comprises the following steps: the compound is crystallized In the organic solvent, and the organic solvent is an ether and/or an aromatic hydrocarbon solvent.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, The crystallization method can be a well-known method in the art, such as suspension stirring, room temperature stirring or solvent volatilization.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, 3-((1H-pyrazolo[3,4-b]pyridin-5-yl)

ethynyl)-4-methyl-N-(4-((4-methylpiperazine-1-yl)methyl)-3-(trifluoromethyl) phenyl) benzamide is prepared by referring to the patent method.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, The organic solvent is preferably one or more of tetrahydrofuran, methyl tert-butyl methyl ether and toluene.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, The mass-volume ratio of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamid to the organic solvent may be a conventional mass-volume ratio in the art, preferably 50:1-1:200 g/mL, more preferably 1:75-1:150 g/mL, such as 1:75 g/mL, 100 g/mL or 150 g/mL.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, the crystallization temperature can be a conventional temperature in the art, for example, 20-50° C.

In the method for preparing the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide solvate, There is no special restriction on the crystallization time, as long as the crystals can be precipitated, for example, 1-36 h.

The present invention also provides a pharmaceutical composition, which comprises the crystal form, salt crystal form or solvate crystal form of the above 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide, and pharmaceutically acceptable excipients. The crystal form, salt crystal form or solvate crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide can be a therapeutically effective amount. The pharmaceutically acceptable excipients can be well-known excipients in the art. In the case of solid preparations, they include, but are not limited to: diluents, binders, disintegrants, lubricants, glidants, release rate control Agents, plasticizers, preservatives, antioxidants, etc.

The pharmaceutical composition can be selected from a dosage form suitable for human consumption, such as: tablets, capsules, granules, powders, or pills, etc., preferably tablets, capsules, granules, disintegrating tablets, sustained release or controlled release tablet.

The pharmaceutical composition of the present invention can be prepared by a method well known in the art, which can combine a therapeutically effective amount of one or more of the crystal form, salt crystal form or solvate crystal form of the 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide with One or more pharmaceutical excipients are mixed to prepare a dosage form suitable for human consumption. For example, tablets, capsules, and granules can be prepared by mixing, granulating, granulating, pressing, or filling capsules.

The present invention also provides an application of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form, salt crystal form or solvate or the above-mentioned pharmaceutical composition in the preparation of medicines. The drug is preferably a drug for preventing and/or treating cancer. The cancer includes, but is not limited to, one or more of gastrointestinal stromal tumor, histiocytic lymphoma, non-small cell lung cancer, small cell lung cancer, pancreatic cancer, breast cancer, prostate cancer, liver cancer, skin cancer, epithelial cell carcinoma, nasopharyngeal carcinoma and leukemia. The medicament preferably contains a therapeutically effective amount of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form, salt crystal form or solvate crystal form, or the above-mentioned pharmaceutical composition.

The crystal form prepared by the present invention has the following advantages:

1. There is no record of the crystal form of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide in the prior art, and a variety of new crystal forms, salts or solvate crystal forms of it have been discovered for the first time in this application. Through a large number of experiments and screening, crystal form I and crystal form II were selected as candidates.

2. The crystal form I and crystal form II prepared by the invention have good stability and convenient storage, can avoid the risk of crystal transformation during drug development or production, avoid changes in bioavailability and drug efficacy, and can be developed into a clinically suitable product. The dosage form used has strong economic value.

3. The invention also provides a method for preparing new crystal forms, salts crystal forms or solvate, crystal forms of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide, which has simple operation and high reproducibility, the solvent is not easy to remain, is environmentally friendly, and is suitable for different scale production.

DETAILED DESCRIPTION

The present invention will be further described in detail below in conjunction with specific embodiments. It should be understood that these embodiments are used to illustrate the basic principles, main features, and advantages of the present invention, and the present invention is not limited by the following embodiments. The implementation conditions used in the examples can be further adjusted according to specific requirements, and implementation conditions not specified are usually conditions in routine experiments.

In the following examples, the experimental methods are usually completed according to conventional conditions or conventional test conditions, and the compounds can be obtained by organic synthesis or by commercially available methods. The compounds used in the following examples were obtained by commercially available methods with a purity of 99%.

The abbreviations used in the present invention are explained as follows:

XPRD—X-ray powder diffraction

TGA—Thermogravimetric analysis

DSC—Differential Scanning Calorimetry

DVS—Dynamic moisture absorption and desorption analysis

PLM—Polarized light microscope analysis

The test conditions are as follows:

XRPD

Using X-ray powder diffractometer (Brooke D8 advance or D2 Phase) was used to characterize the solid.

Scanning angle: 30 (2θ)-40 (2θ).

Step size: 0.02° (2θ).

Scan speed: 0.3 sec/step (D8), 0.2 sec/step (D2).

Light tube voltage: 40 KV (D8), 30 KV (D2).

Light tube current: 40 mA (D8), 10 mA (D2).

Rotation: On.

Sample tray: zero background sample tray.

TGA

Use TA Instrument thermogravimetric analysis Q500 or Discovery TGA 55 to perform thermogravimetric analysis of solid samples. After balancing the sample pan, hang the sample on the hanging wire and raise it onto the furnace. After stabilization, heat the sample to different endpoint temperatures at a rate of 10° C./min.

DSC

TA Instrument differential scanning calorimeter Q200 and Discovery DSC 250 were used for DSC analysis of solid samples. Weigh the sample and record the value, then place the sample in the sample chamber. The samples were heated from 25° C. to different endpoint temperatures at a rate of 10° C./min.

DVS

DVS analysis of solids using IGASORP dynamic water adsorption instrument.

temperature: 25° C.

airflow: 250 mL/min.

Scan loop: 2.

Minimum test time: 30 min.

Longest test time: 2 h.

Waiting for balance: 98%.

PLM

Observe the sample with Nikon Eclipse LV100N POL polarizing microscope.

Example 1: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of methanol, stirred at room temperature for 1-3 h, filtered and collected the solid to obtain crystal form I.

Figure 1:
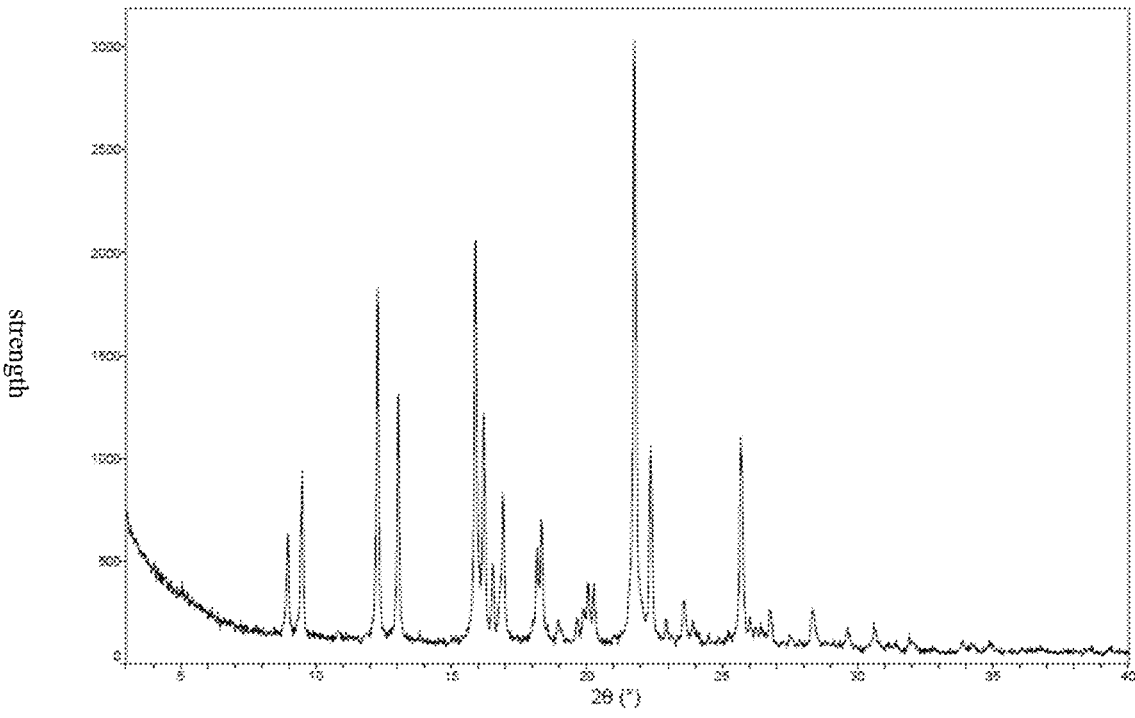
FIG. 1 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form I.
Figure 2:
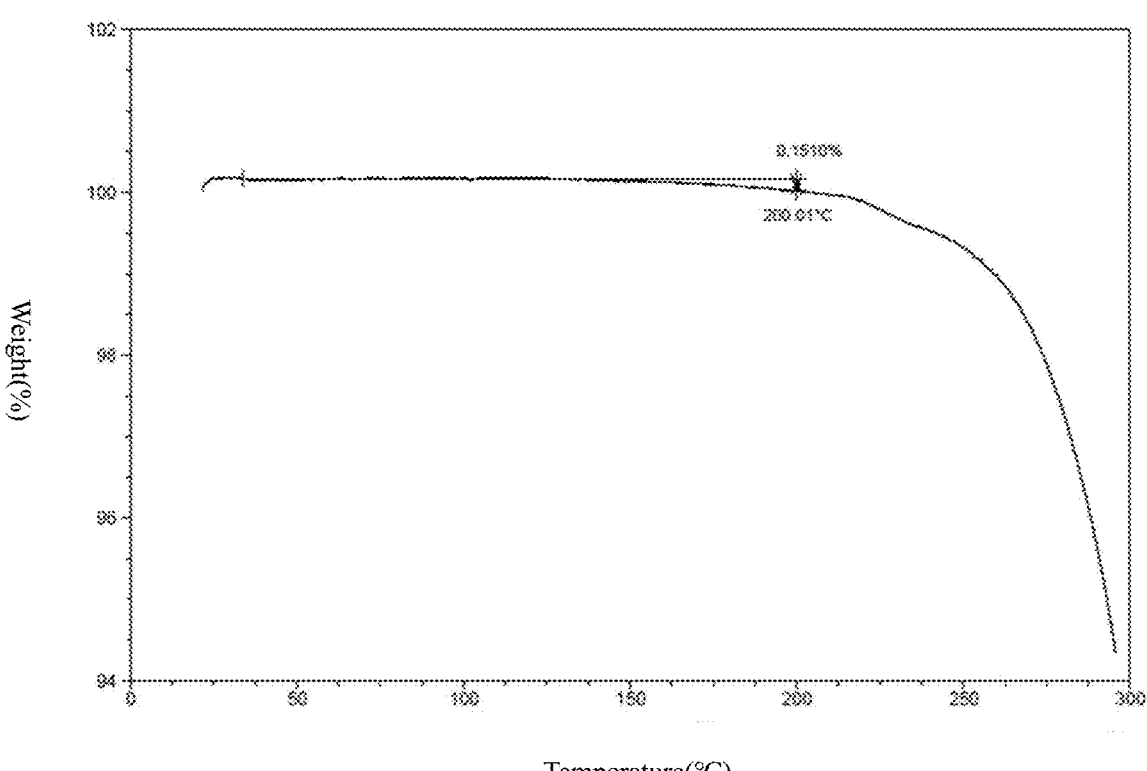
FIG. 2 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form I.
Figure 3:
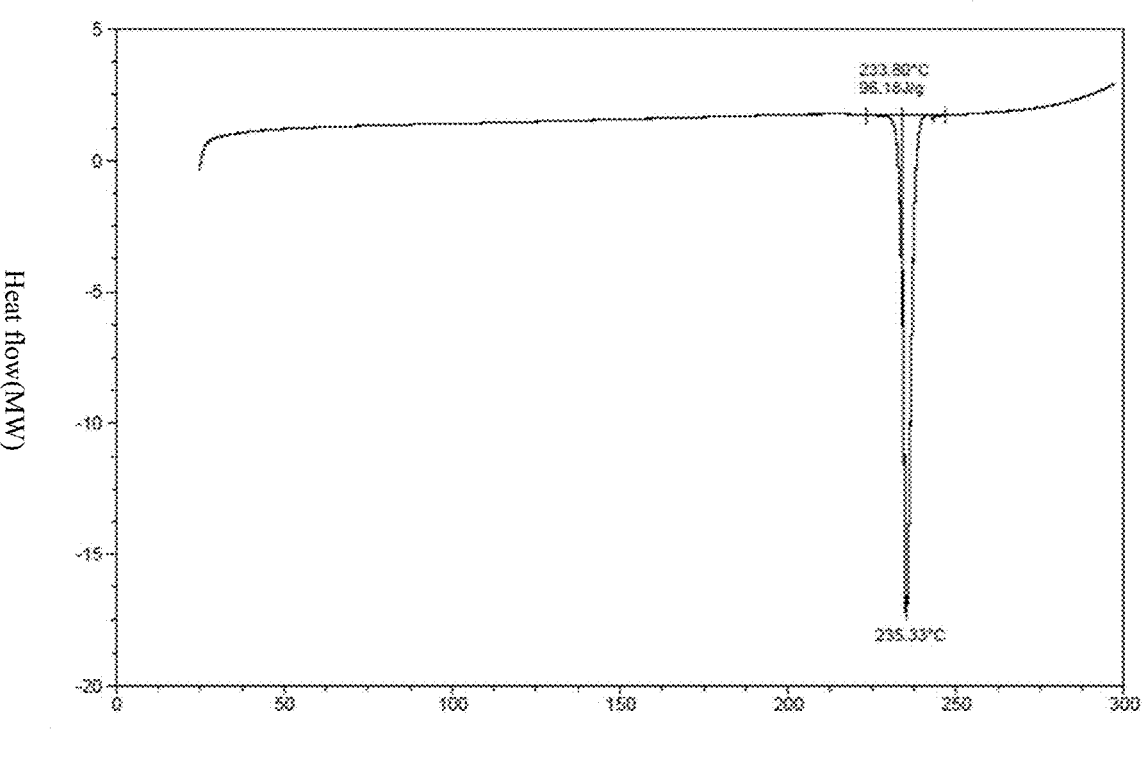
FIG. 3 is a DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form I.
Figure 4:
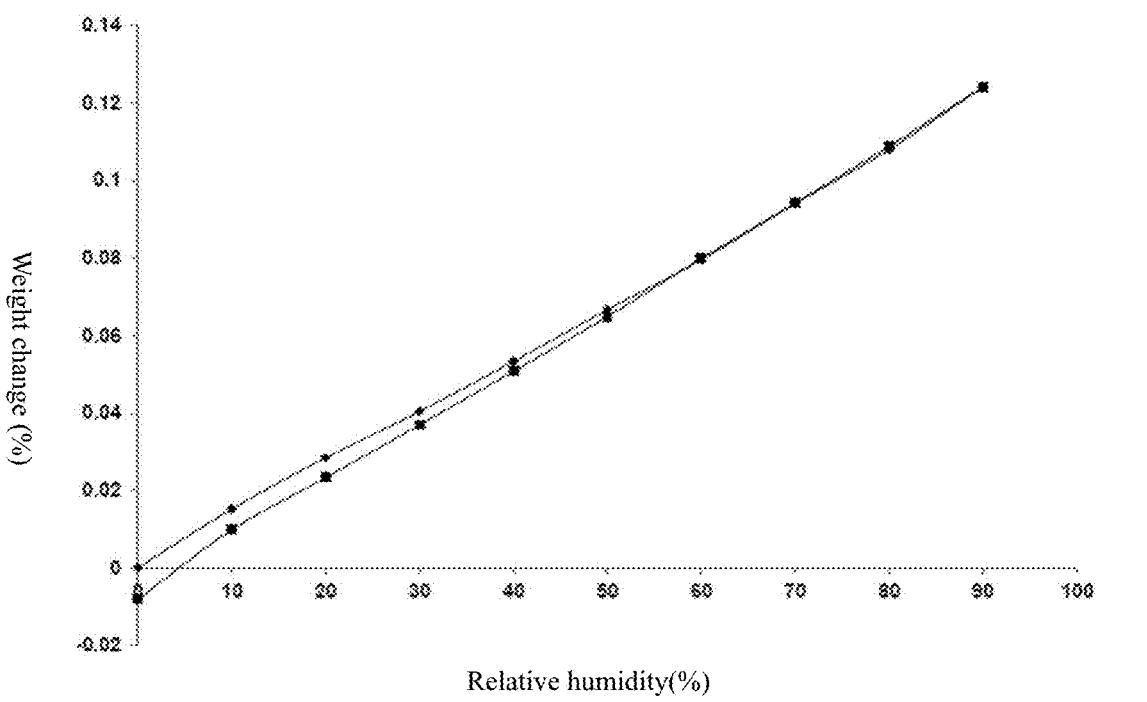
FIG. 4 is the DVS diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form I.
Figure 5:
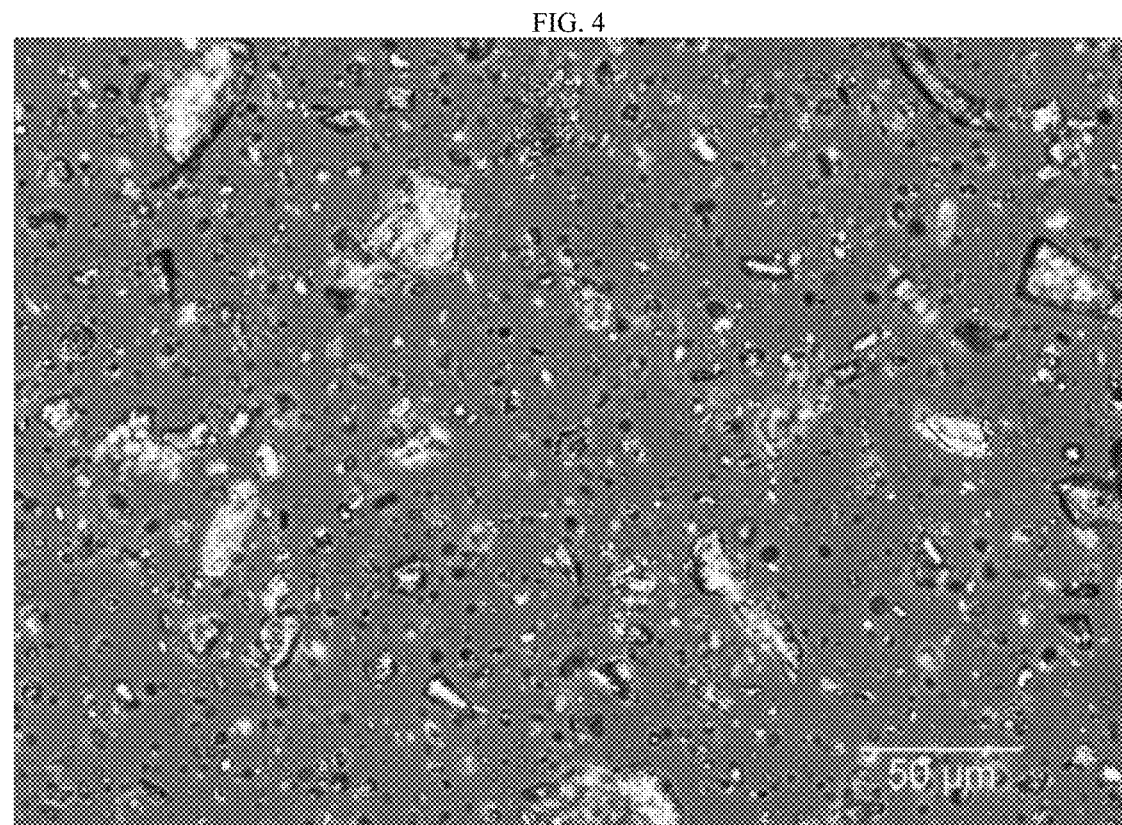
FIG. 5 is a microscope image of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide crystal form I.
Figure 6:
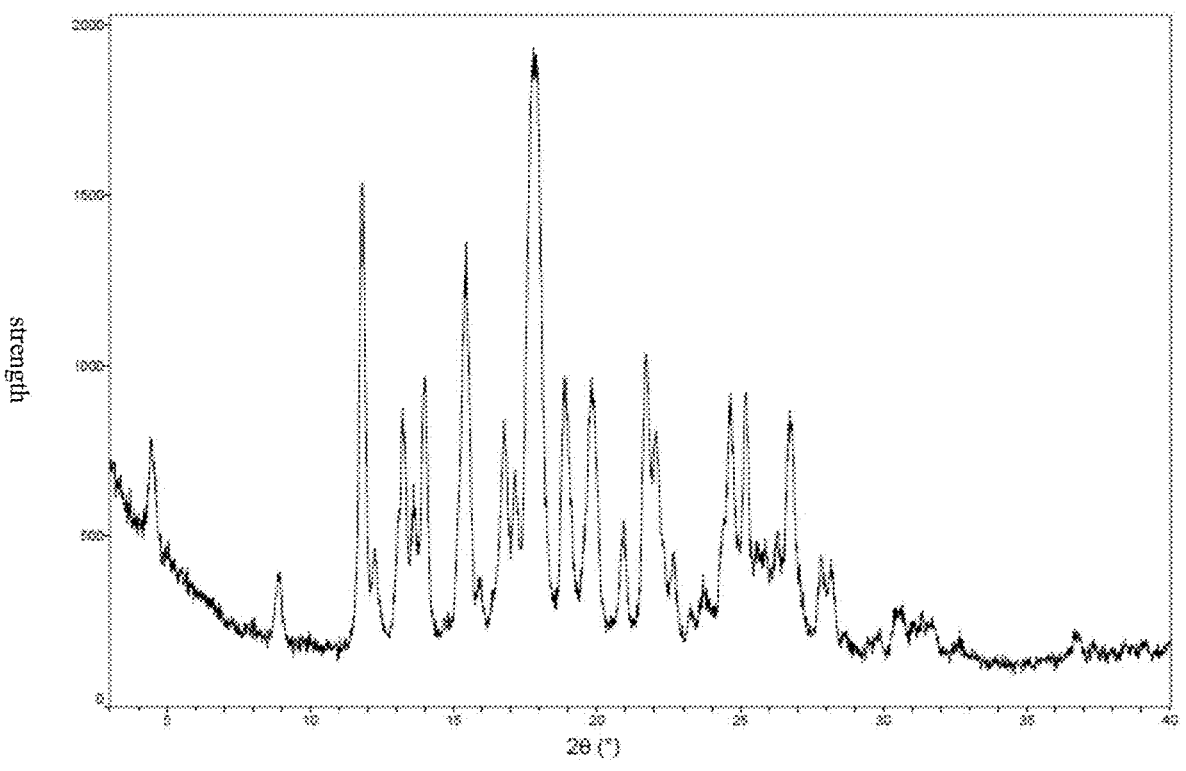
FIG. 6 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide fumarate crystal form II.
Figure 7:
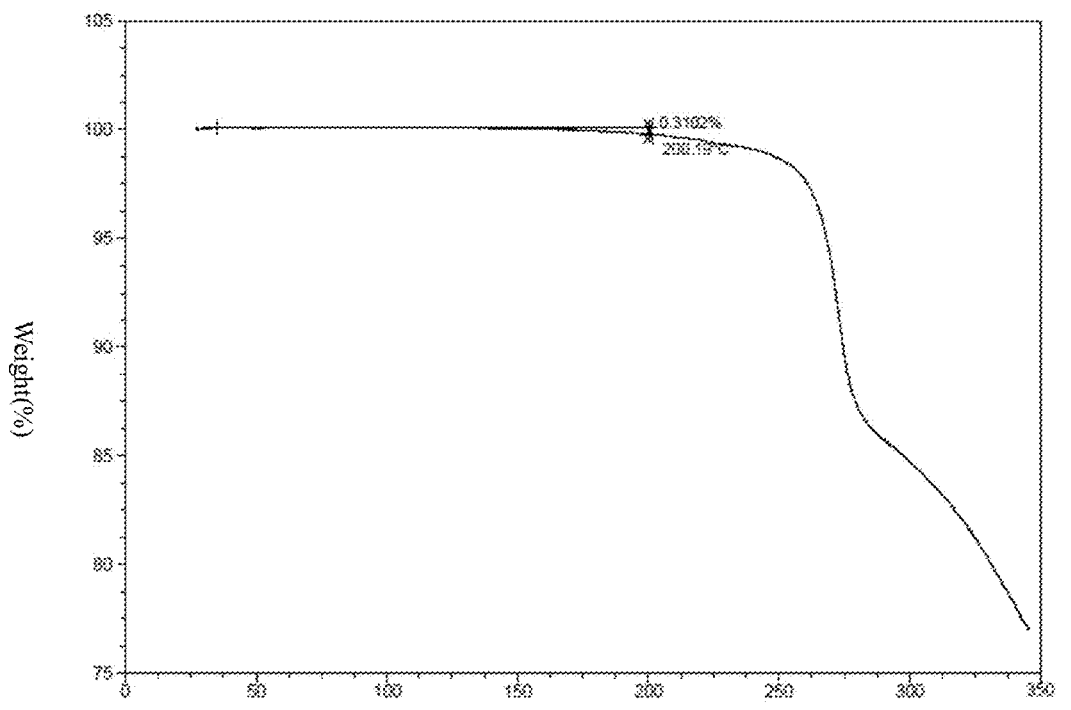
FIG. 7 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide fumarate crystal form II.
Figure 8:
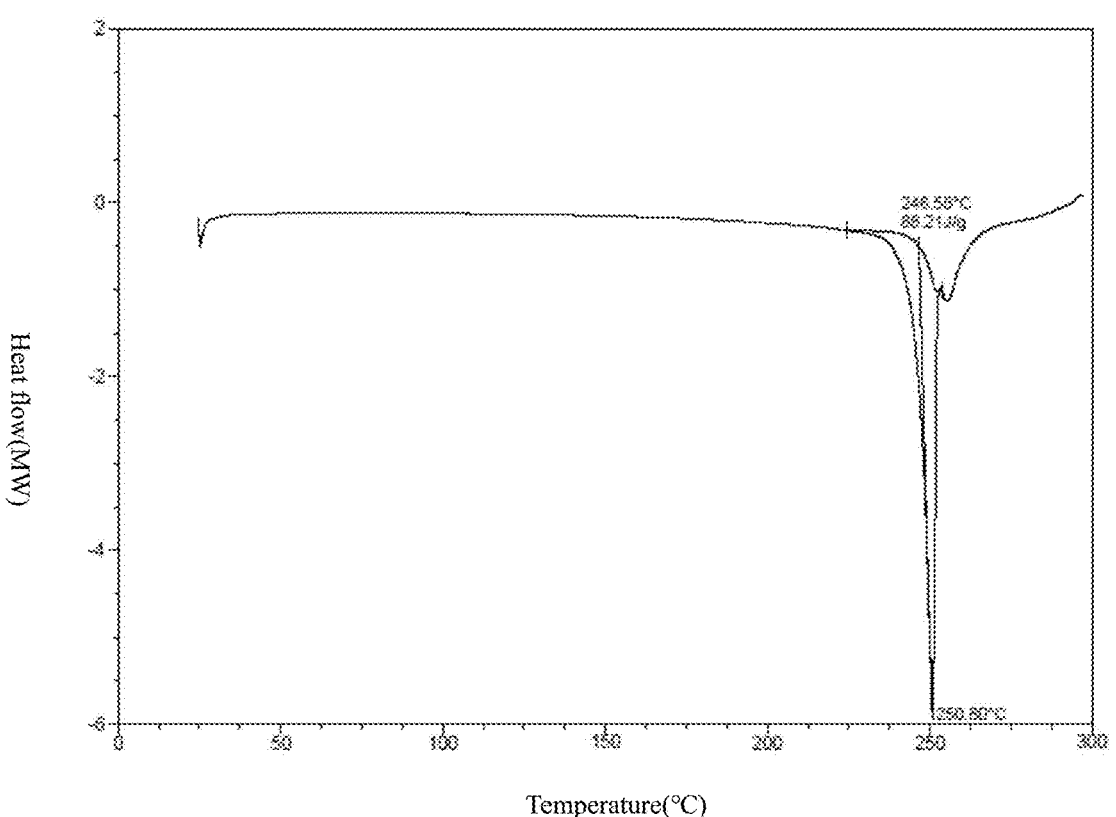
FIG. 8 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate crystal form II.
Figure 9:
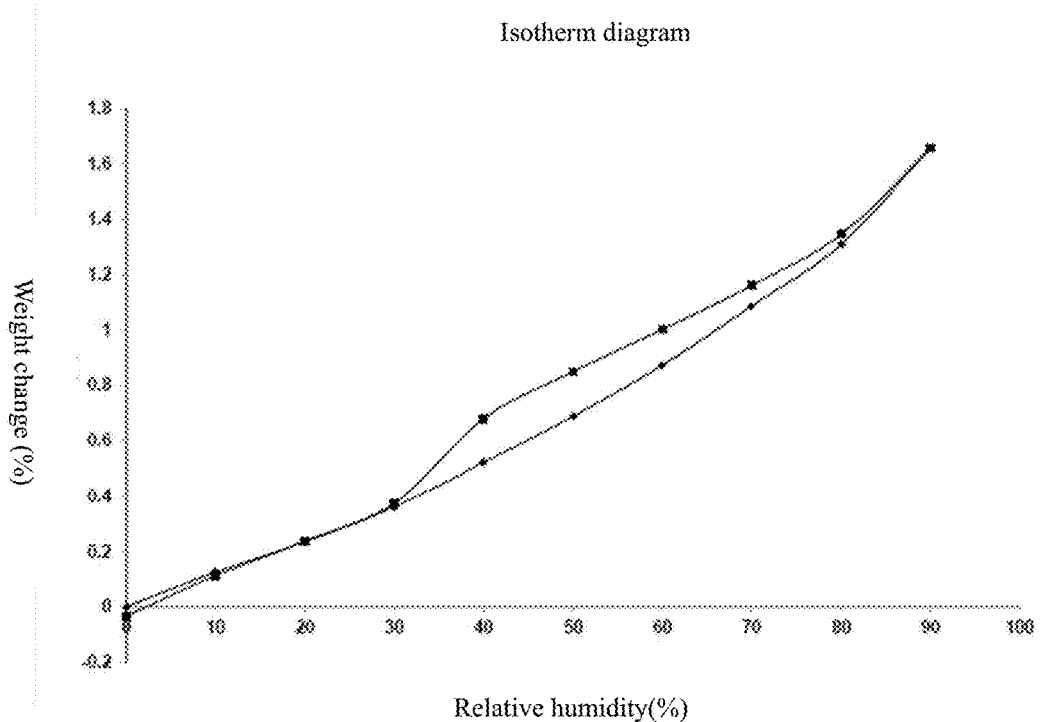
FIG. 9 is the DVS diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate crystal form II.
Figure 10:
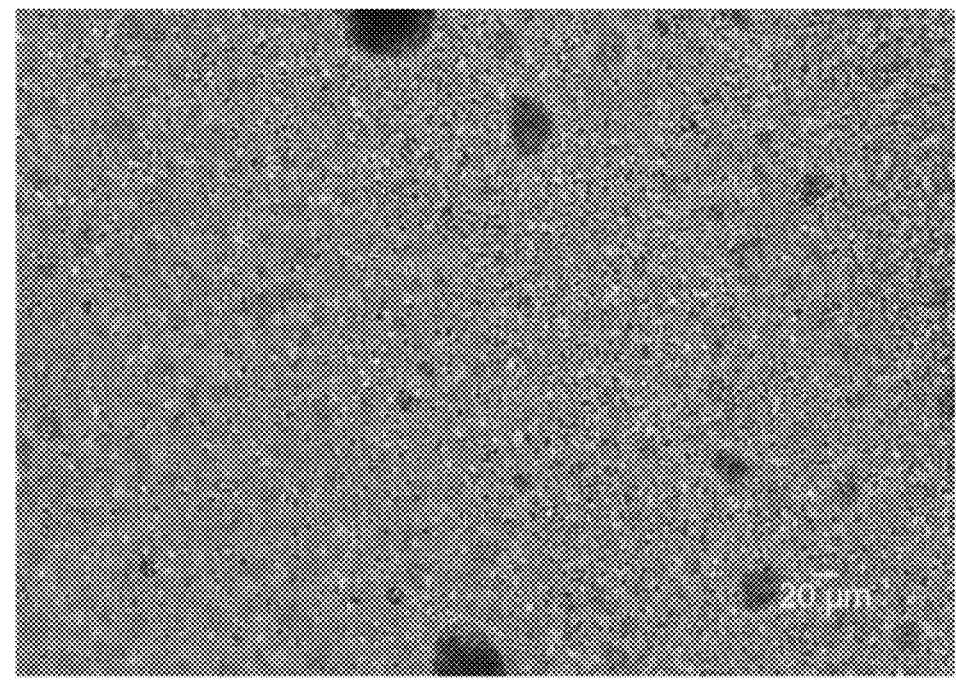
FIG. 10 is the microscope image of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate crystal form II.

The XPRD chart of crystal form I is shown in FIG. 1; the TGA chart is shown in FIG. 2; the DSC chart is shown in FIG. 3; The DVS picture is shown in FIG. 4; the microscope picture is shown in FIG. 5.

Example 2: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of ethanol, stirred at room temperature for 1-3 h, filtered and collected the solid to obtain crystal form I.

Example 3: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of isopropanol, stirred at room temperature for 1-3 h, filtered and collected the solid to obtain crystal form I.

Example 4: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of methyl tert-butyl ether, stirred at room temperature for 1-3 h, filtered and collected the solid to obtain crystal form I.

Example 5: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of 2-butanone, stirred at room temperature for 1-3 h, filtered and collected the solid to obtain crystal form I.

Example 6: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of acetonitrile, stirred at room temperature for 1-3 h, filtered and collected the solid to obtain crystal form I.

Example 7: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of acetone, stirred at room temperature for 1-3 h, filtered and collected the solid to obtain crystal form I.

Example 8: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of isopropyl acetate, stirred at room temperature for 1-3 h, filtered and collected the solid to obtain crystal form I.

Example 9: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of methanol, heated to 50° C. and stirred for 1-5 h, then cooled to room temperature, filtered and collected the solid to obtain crystal form I.

Example 10: Preparation of Form I

Using the same reaction conditions as in Example 1, and replacing the solvent with heptane or ethyl acetate, crystalline form I can be obtained.

Example 11: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of DMSO, stirred at room temperature for 1-3 h, 0.1 mL of water was slowly added, and the solid was filtered and collected to obtain crystal form I.

Example 12: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of DMSO, stirred at room temperature for 1-3 h, 0.3 mL of acetonitrile was slowly added, and the solid was filtered and collected to obtain crystal form I.

Example 13: Preparation of Form I 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.1 mL of DMSO, stirred at room temperature for 1-3 h, 0.8 mL of Isopropanol was slowly added, and the solid was filtered and collected to obtain crystal form I.

The XPRD pattern, TGA pattern, DSC pattern, DVS pattern and microscope picture of the crystal form I prepared in the foregoing Examples 2-13 are basically the same as the crystal form I prepared in Example 1.

Effect Example 1: Stability Test of Crystal Form I (Different Temperature, Humidity and Light)

The stability of the crystal form I prepared in Examples 1-13 was studied. Before the test, the single impurities of the crystal form I were less than 0.05%, and the total impurities were less than 0.05%.

Place the crystal form I under 60° C., high humidity, and light conditions, and sample at 0 days/5 days/10 days to investigate its content and related substances. The lighting conditions are: total illuminance: ≥1.2×106 Lux·hr, near ultraviolet energy ≥200 w·hr/m2. The results are shown in Table 19.

TABLE 19

| Form I | content | Single impurity | Total impurities | XPRD |
|---|---|---|---|---|
| 0 day | 101.2% | <0.05% | <0.05% | Form I |
| 5 days-high humidity | 101.4% | <0.05% | <0.05% | Form I |
| 5 days-light | 101.5% | <0.05% | <0.05% | Form I |
| 5 days-60° C. | 100.8% | <0.05% | <0.05% | Form I |
| 10 days-high humidity | 100.9% | <0.05% | <0.05% | Form I |
|  |  |  |  | Form I |
| 10 days-light | 100.4% | <0.05% | <0.05% | Form I |
| 10 days-60° C. | 100.8% | <0.05% | <0.05% | Form I |

The results showed that the content and purity of crystal form I measured at 60° C., high humidity and light conditions on 5 and 10 days were almost unchanged, and the content was close to 100%, and the single impurity content was less than 0.05%, total impurity content <0.05%, crystal form I showed good stability.

Effect Example 2: Stability Test of the Crystal Form I Prepared in Examples 1-13 (Different Solvents)

Weigh the sample crystal form I and place it in a sample bottle, and then add a solvent to prepare a suspension. The resulting suspension is stirred at room temperature and 50° C. for 3 days, then filtered and collected the solid, and the solid is characterized. The results are shown in Table 20 below.

TABLE 20

| The suspension stirring experiment of crystal form I | | | |
|---|---|---|---|
| Serial number | solvent | Room temperature suspension | 50° C. suspension |
| 1 | Methanol | Form I | Form I |
| 2 | Ethanol | Form I | Form I |
| 3 | Isopropanol | Form I | Form I |
| 4 | Methyl tert-butyl ether | Form I | Form I |
| 5 | Butanone | Form I | Form I |
| 6 | Acetonitrile | Form I | Form I |
| 7 | Acetone | Form I | Form I |
| 8 | Ethyl acetate | Form I | Form I |
| 9 | Isopropyl acetate | Form I | Form I |
| 11 | Acetonitrile:water 1:1 (v:v) | Form I | Form I |

It can be seen from the above table that the crystal form I has good stability in a variety of solvents.

Effect Example 3: Hygroscopicity Test of Crystal Form I

The hygroscopicity of the crystal form I prepared in Examples 1-13 was studied, and 10 mg of the crystal form I was taken for a dynamic moisture adsorption (DVS) test. The conclusions are described in Table 21 below:

TABLE 21

| Free base/salt | DVS (90% RH) | DVS 前后 XRPD |
|---|---|---|
| Crystal form I | 0.12% | Unchanged |

The above shows that the crystal form I is not easy to absorb water during storage, is easy to store, and can have a longer shelf life.

Example 14: Preparation of Form III 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.2 mL methanol and dichloromethane (the volume ratio of methanol to dichloromethane is 1:1) and mixed into the system, stirred at room temperature, 1.05 equivalent of hydrochloric acid was added, the solid was completely dissolved, ethyl acetate was added, and stirring was continued for 0.5 h, a solid precipitated, continued stirring for 4 h, filtered, and dried under vacuum at 50° C. overnight to obtain crystal form III.

Figure 11:
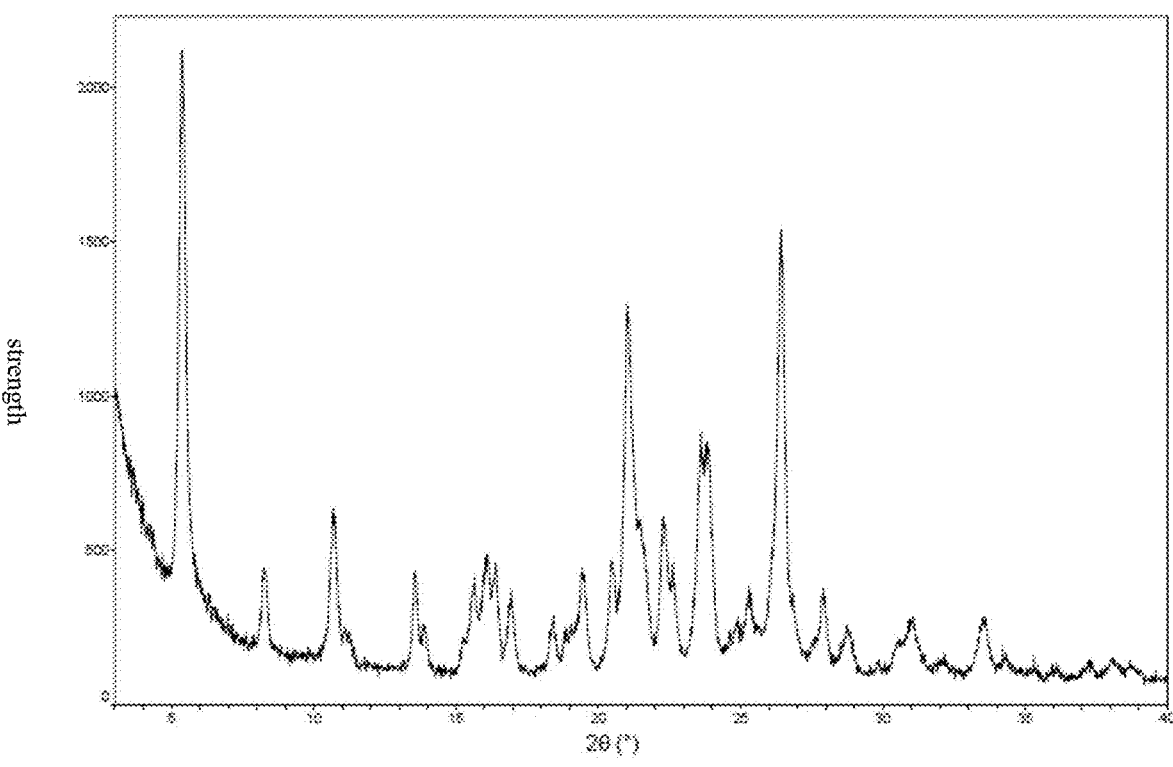
FIG. 11 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide monohydrochloride crystal form III.
Figure 12:
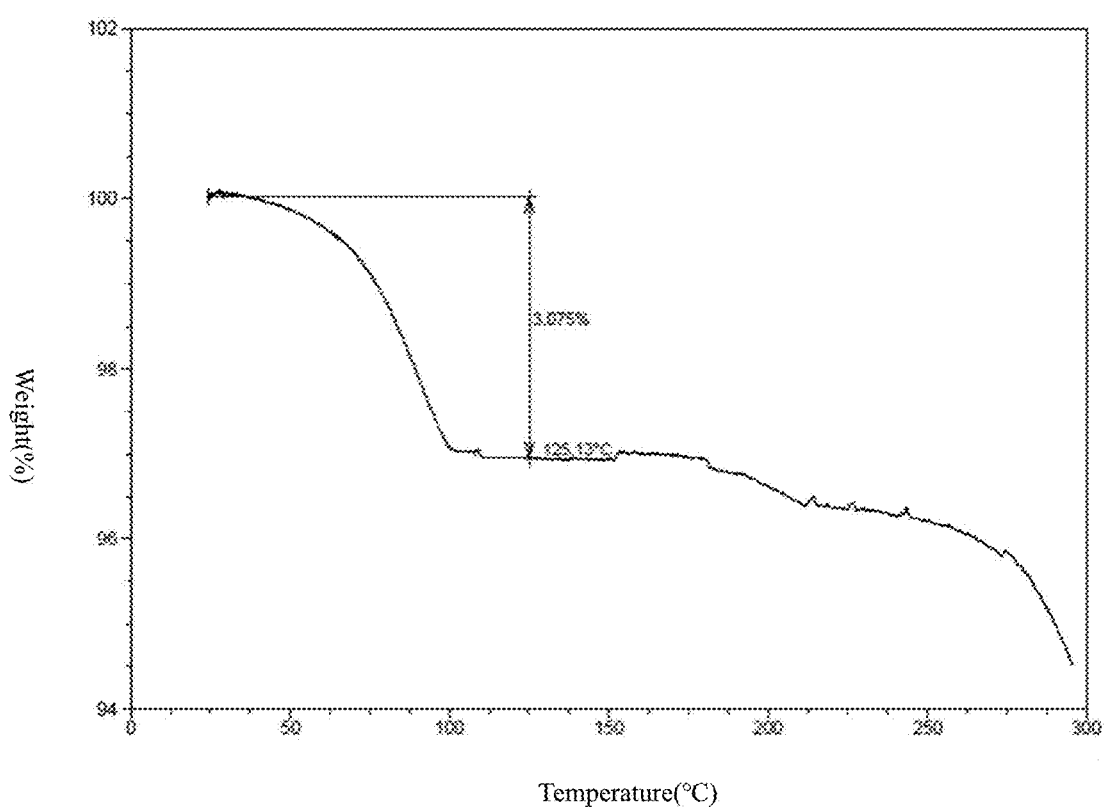
FIG. 12 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide monohydrochloride crystal form III.
Figure 13:
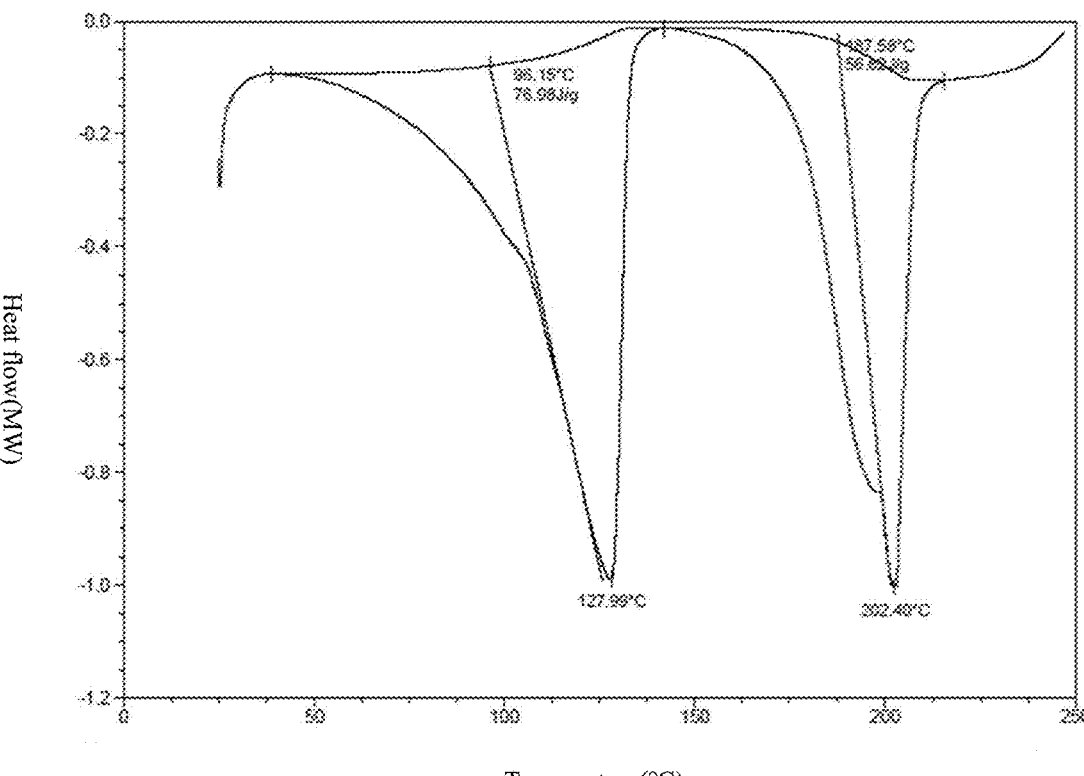
FIG. 13 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide monohydrochloride crystal form III.

The XPRD pattern of crystal form III is shown in FIG. 11; the TGA pattern is shown in FIG. 12; and the DSC pattern is shown in FIG. 13.

Example 15: Preparation of Form IV 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.4 mL of methanol and dichloromethane (the volume ratio of methanol to dichloromethane is 1:1) and mix into the system, stir at room temperature, add 2.1 equivalents of hydrochloric acid to precipitate a solid, continue to stir for 1-2 h, and filter. Dry under vacuum at 50° C. overnight to obtain crystal form IV.

Figure 14:
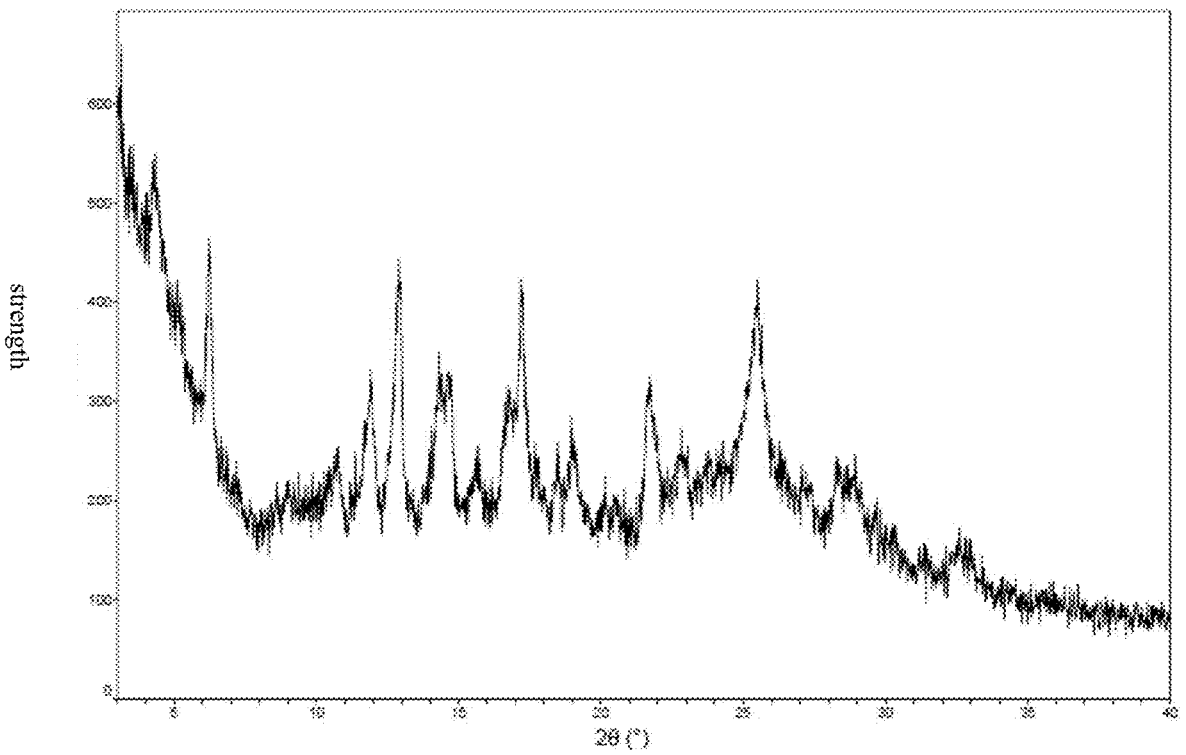
FIG. 14 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form IV.
Figure 15:
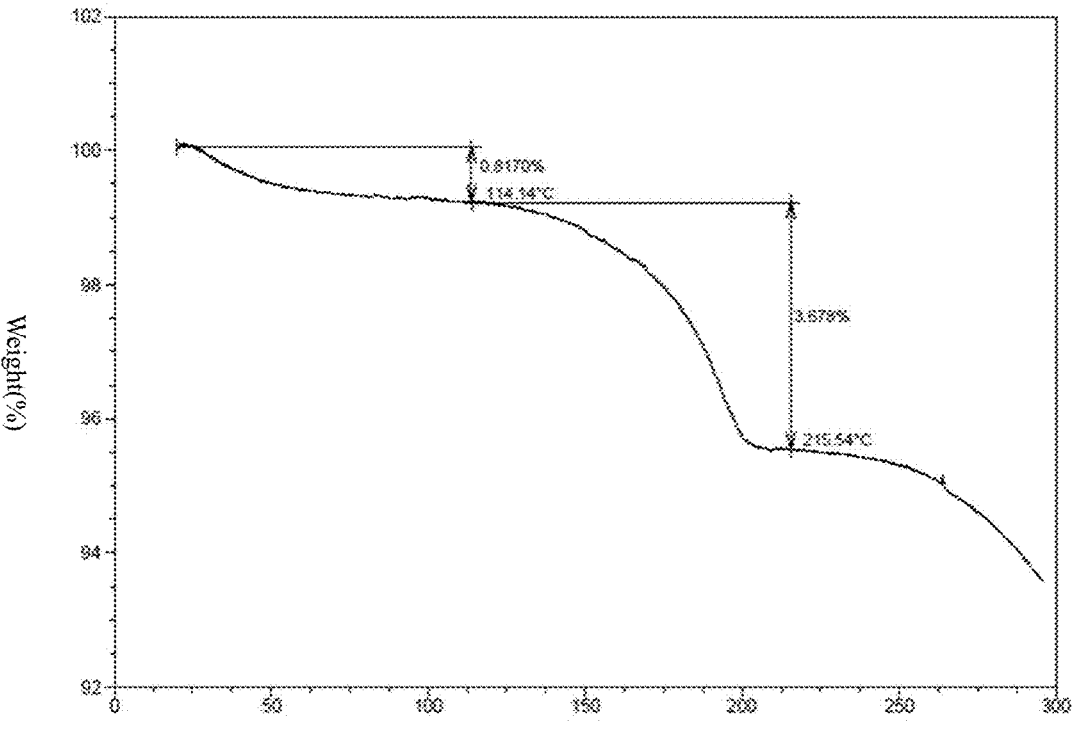
FIG. 15 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form IV.
Figure 16:
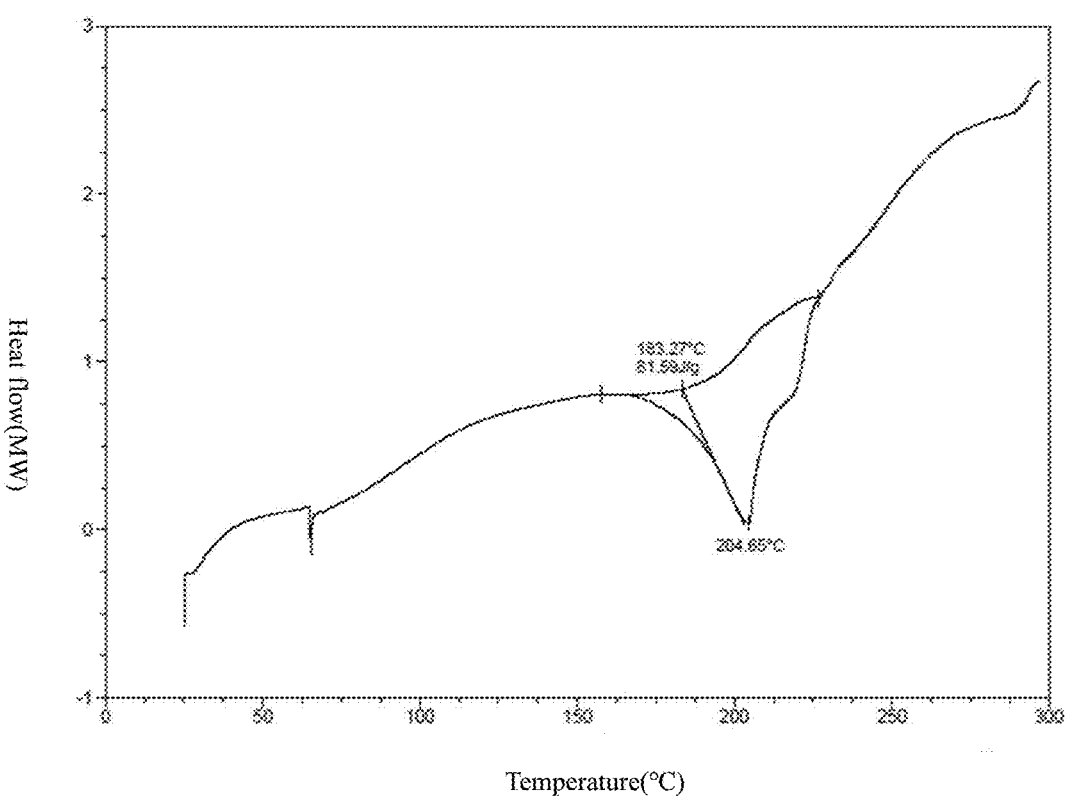
FIG. 16 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form IV.

The XPRD pattern of crystal form IV is shown in FIG. 14; the TGA pattern is shown in FIG. 15; and the DSC pattern is shown in FIG. 16.

Example 16: Preparation of Form VI 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.4 mL of methanol and dichloromethane (1:1), stirred at room temperature, and 1 equivalent of sulfuric acid was added to dissolve the solid and continue stirring. Ethyl acetate (2 mL) was added to produce a solid precipitate, which was slowly reduced to room temperature, stirred overnight, filtered, and dried in vacuum at 50° C. overnight to obtain crystal form VI.

Figures 20, 21:
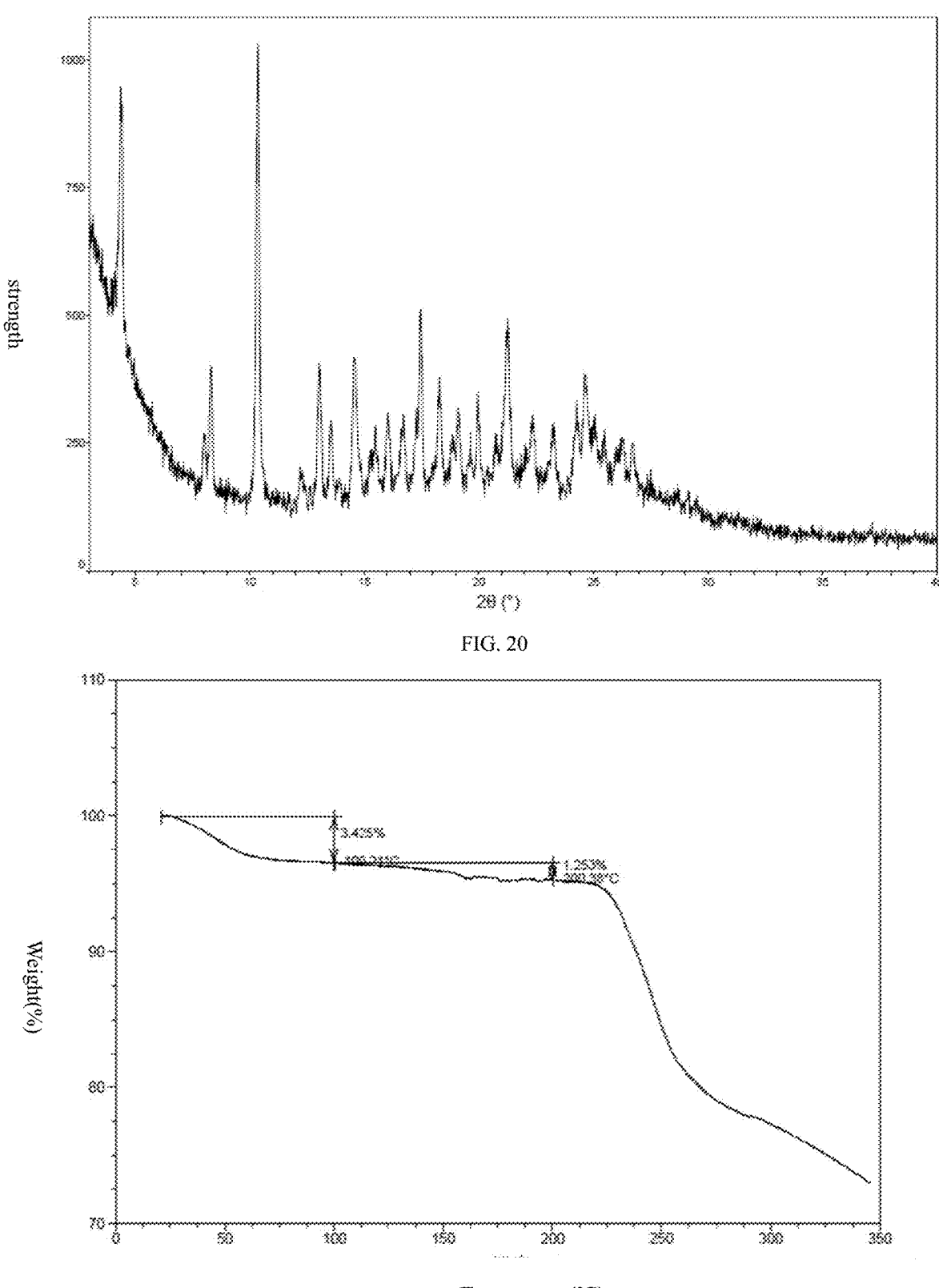
FIG. 20 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Sulfate crystal form VI.
FIG. 21 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Sulfate crystal form VI.
Figure 22:
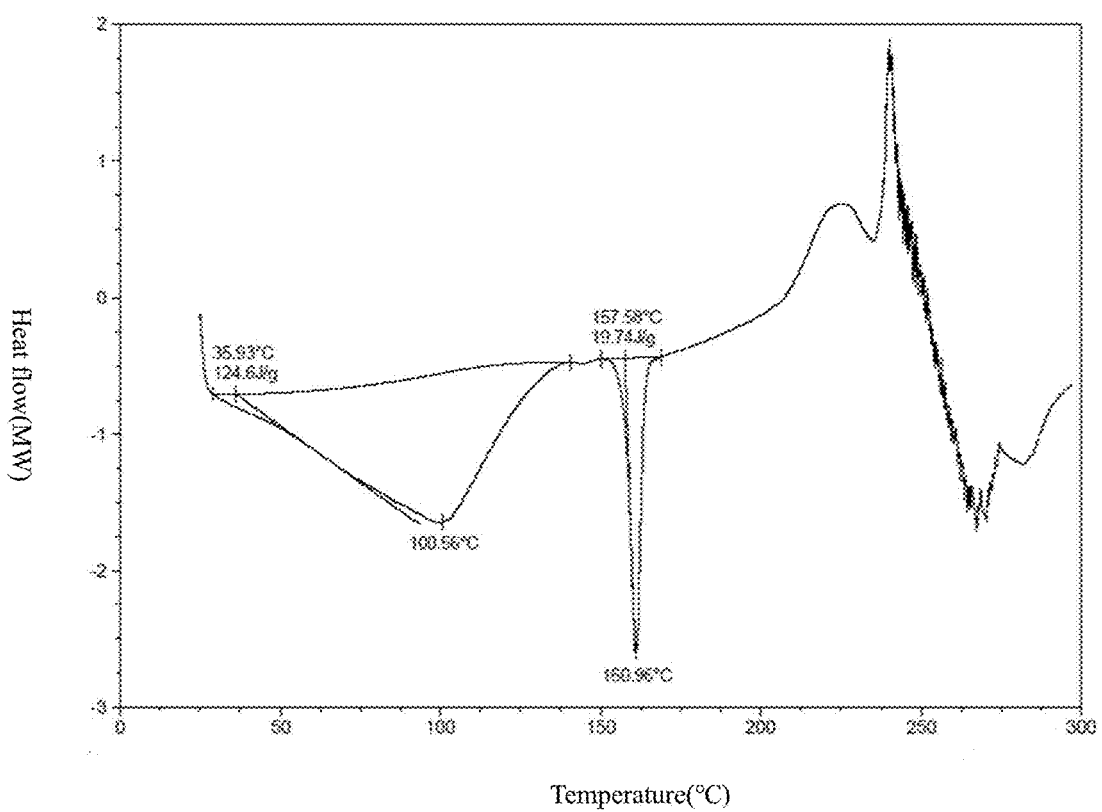
FIG. 22 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Sulfate crystal form VI.

The XPRD pattern of crystal form VI is shown in FIG. 20; the TGA pattern is shown in FIG. 21; and the DSC pattern is shown in FIG. 22.

Example 17: Preparation of Form VII 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 1 mL ethanol, heated to 50° C. and stirred, 1 equivalent of phosphoric acid was added, the solid was dissolved, and the stirring was continued to produce solid precipitation. Continue stirring at 50° C. for 0.5 h, then lower to room temperature and stir for 2 h, filter, dry in vacuum overnight at 50° C. to obtain crystal form VII.

Figure 23:
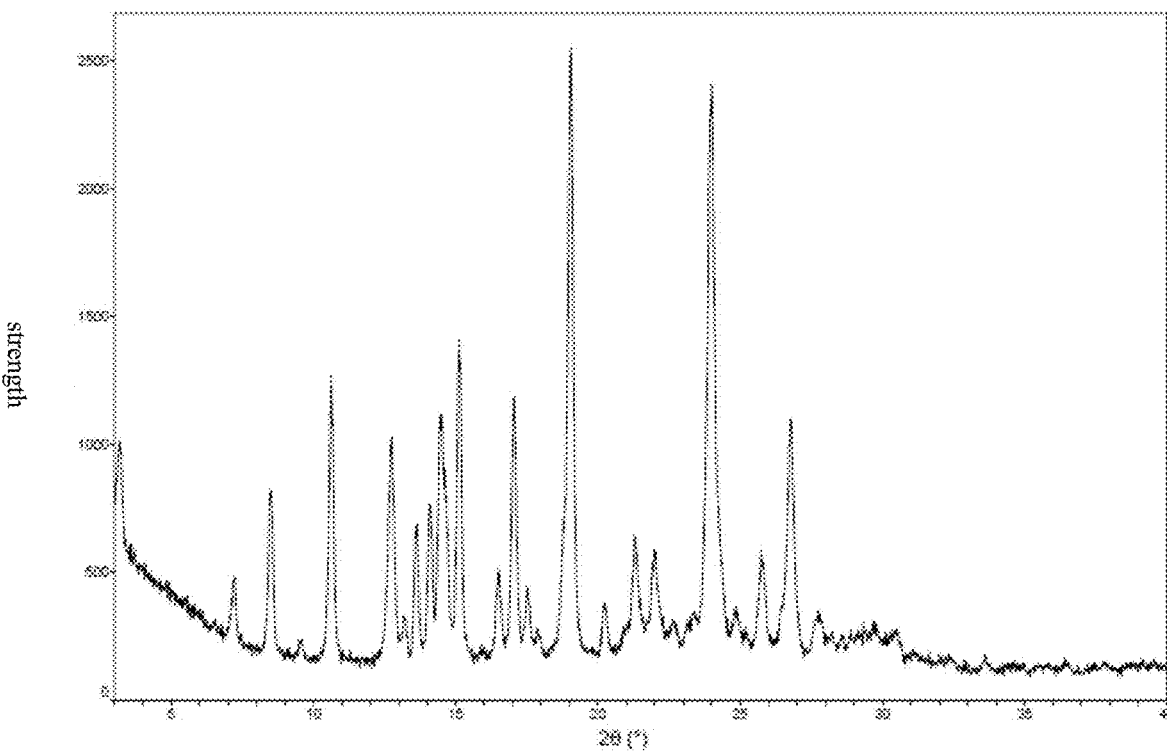
FIG. 23 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Phosphate crystal form VII.
Figure 24:
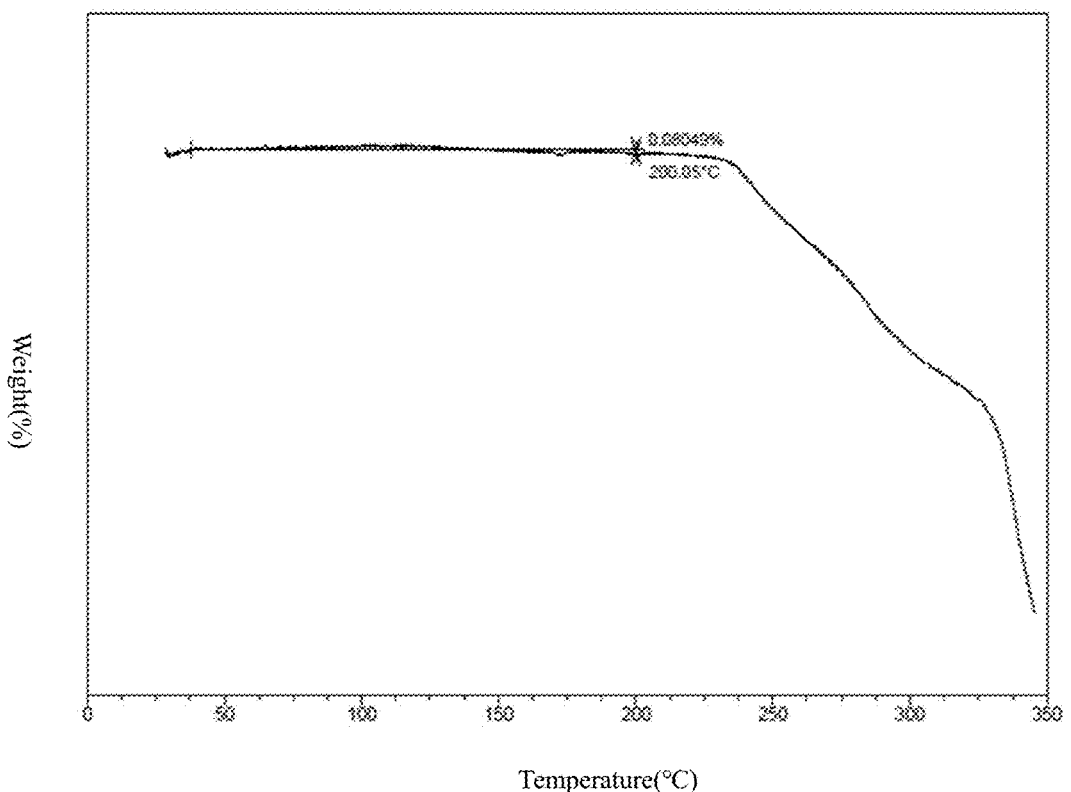
FIG. 24 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Phosphate crystal form VII.
Figure 25:
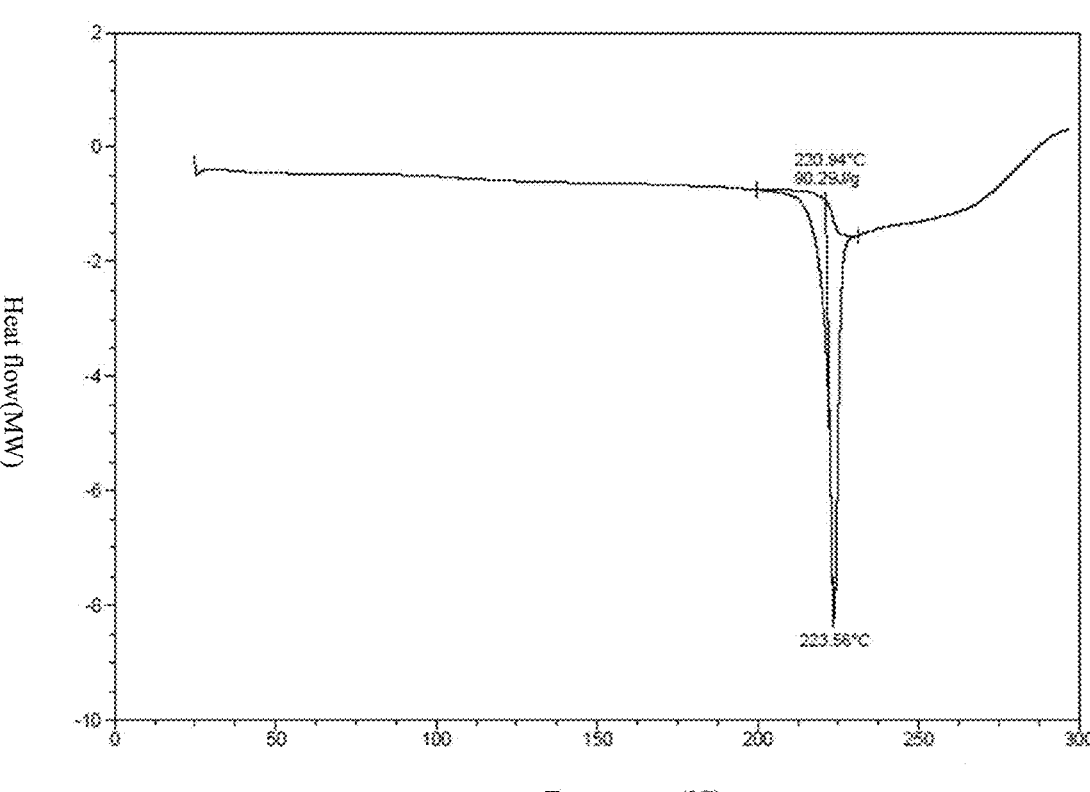
FIG. 25 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Phosphate crystal form VII.

The XPRD pattern, TGA pattern, and DSC pattern of Form VII are shown in FIGS. 23, 24 and 25, respectively.

Example 18: Preparation of Form V 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 1 mL ethanol, heated to 50° C. and stirred, 1 equivalent of hydrobromic acid was added, the solid was dissolved, and the stirring was continued to produce a solid precipitate. Slowly reduce to room temperature, continue stirring for 2 h, filter, and vacuum dry at 50° C. overnight to obtain Form V.

Figure 17:
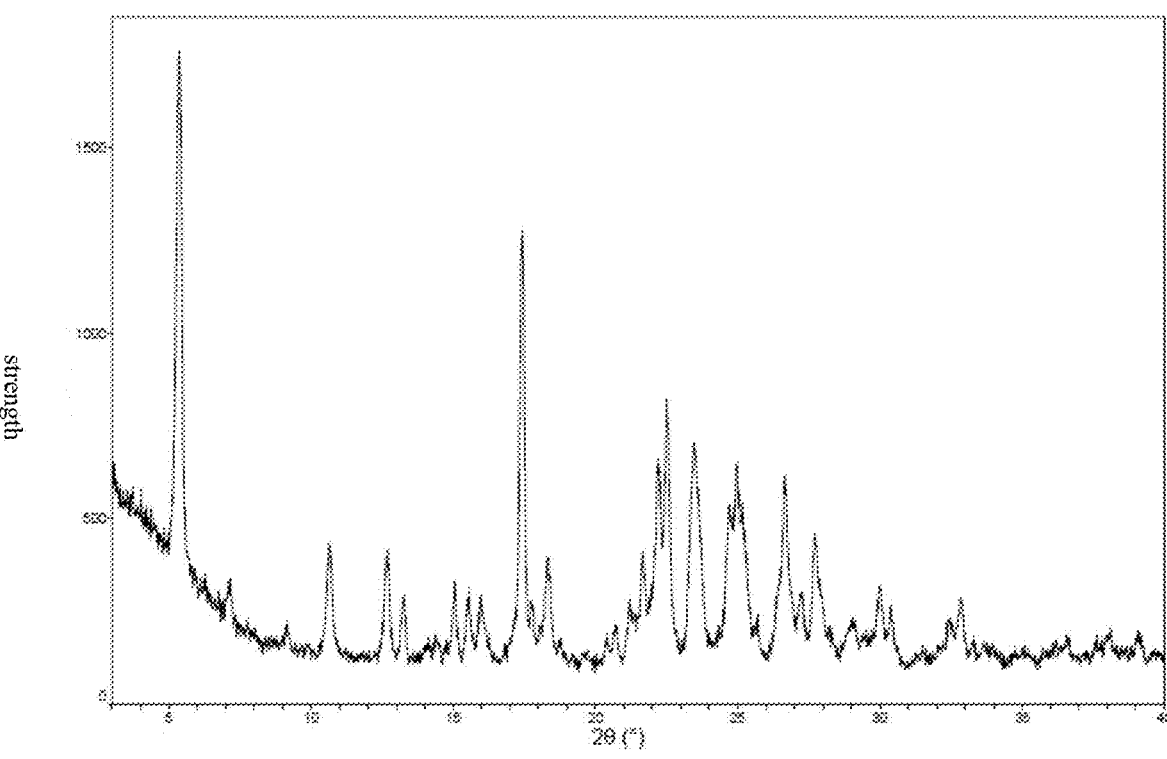
FIG. 17 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Hydrobromide crystal form V.
Figure 18:
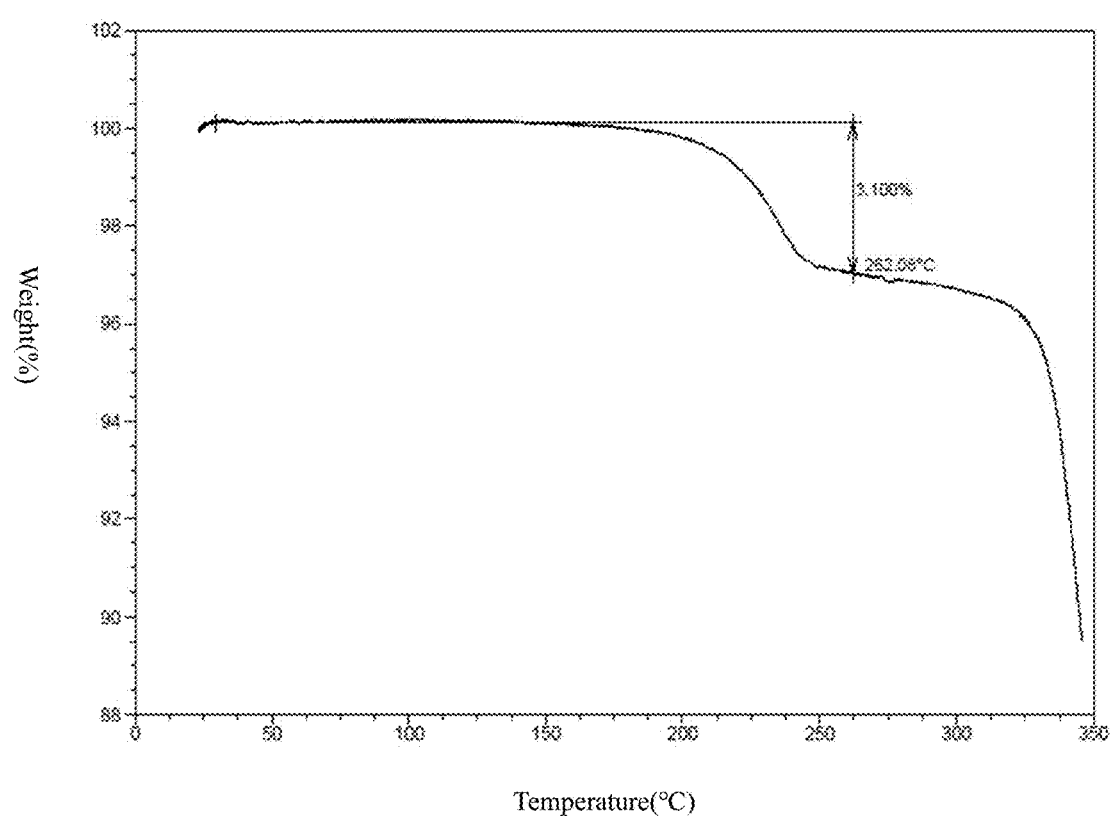
FIG. 18 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Hydrobromide crystal form V.
Figure 19:
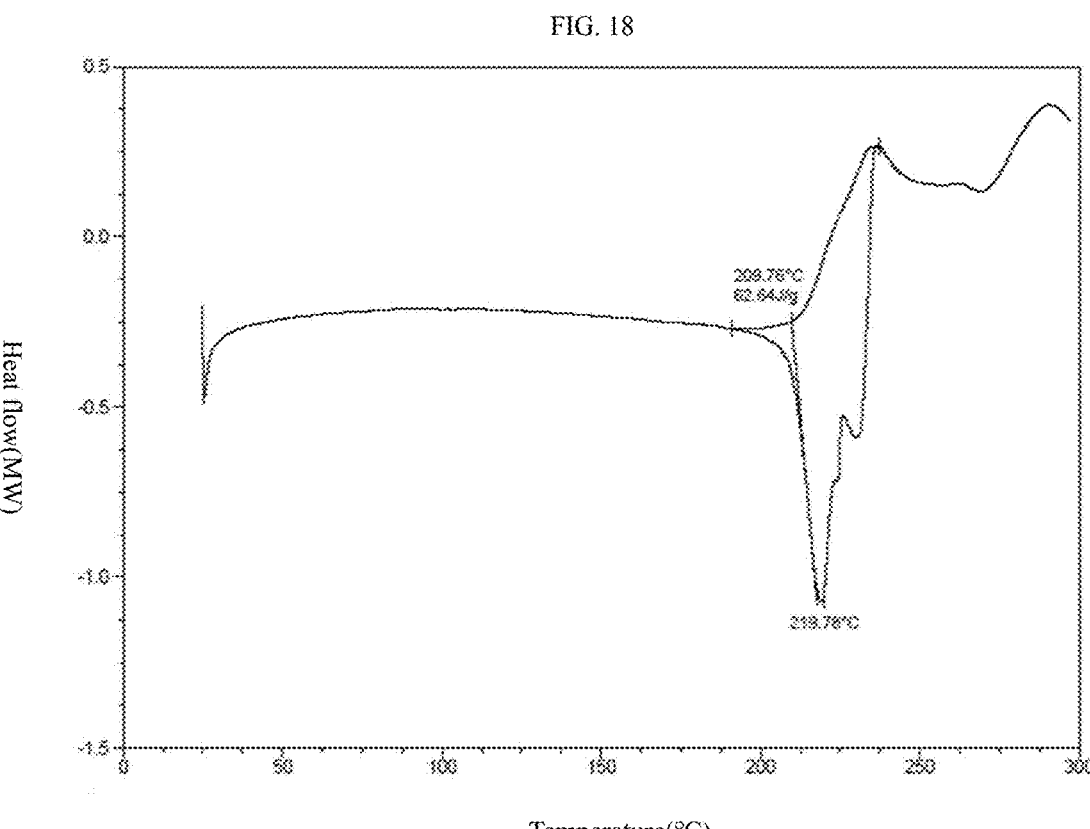
FIG. 19 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Hydrobromide crystal form V.

The XPRD pattern, TGA pattern, and DSC pattern of Form V are shown in FIGS. 17, 18 and 19, respectively.

Example 19: Preparation of Form X 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 1 mL of ethanol, stirred at 50° C., 1.05 equivalent of methanesulfonic acid was added, the solid was dissolved, slowly reduced to room temperature, stirred for 2 h, filtered, and dried under vacuum at 50° C. overnight to obtain crystal form X.

Figure 32:
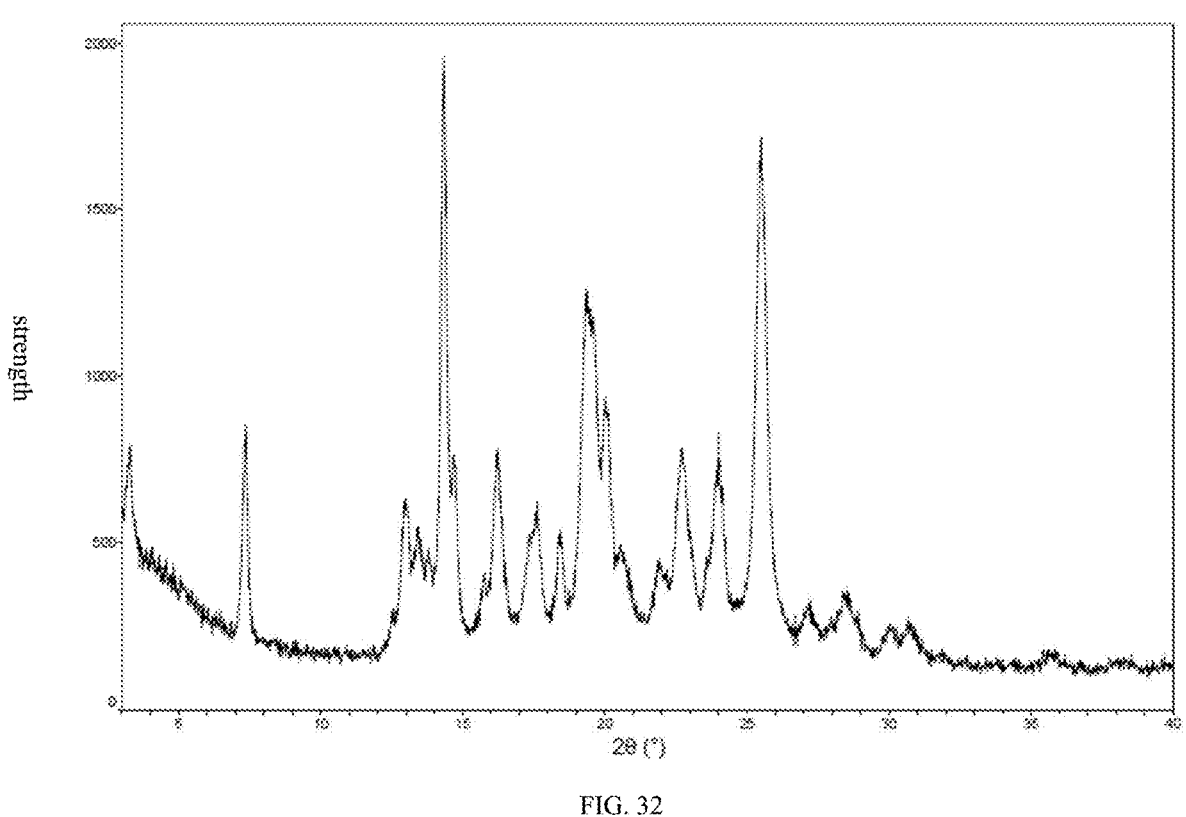
FIG. 32 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Methanesulfonate Form X.
Figure 33:
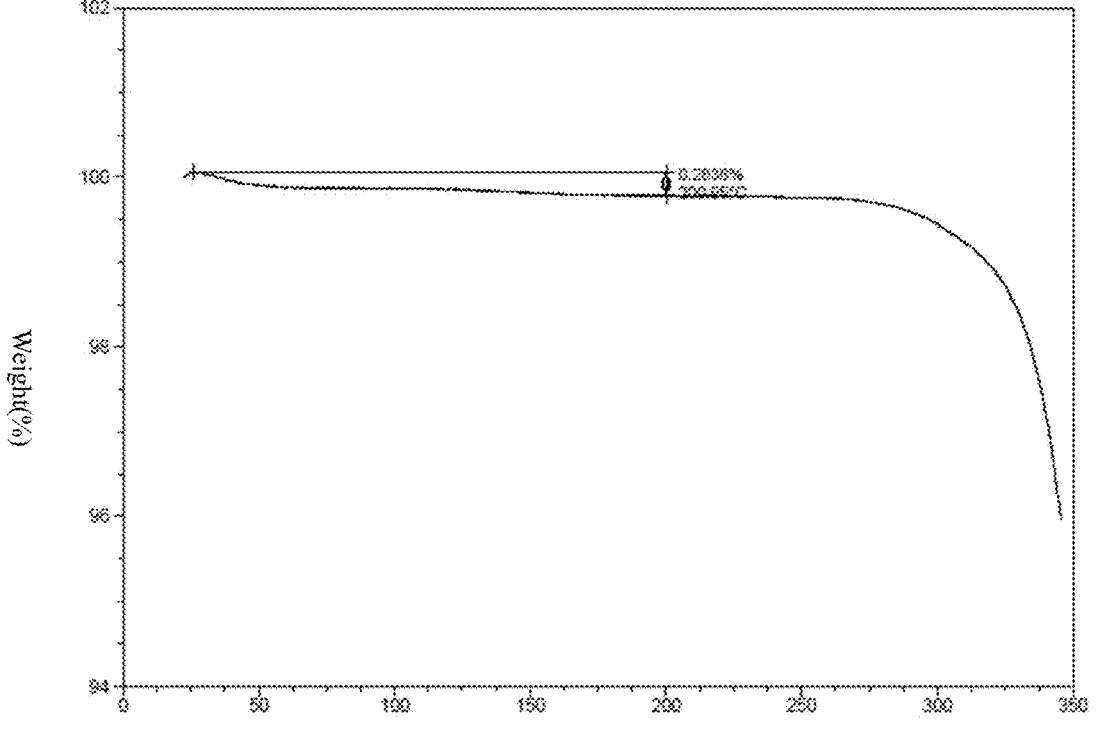
FIG. 33 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Methanesulfonate Form X.
Figure 34:
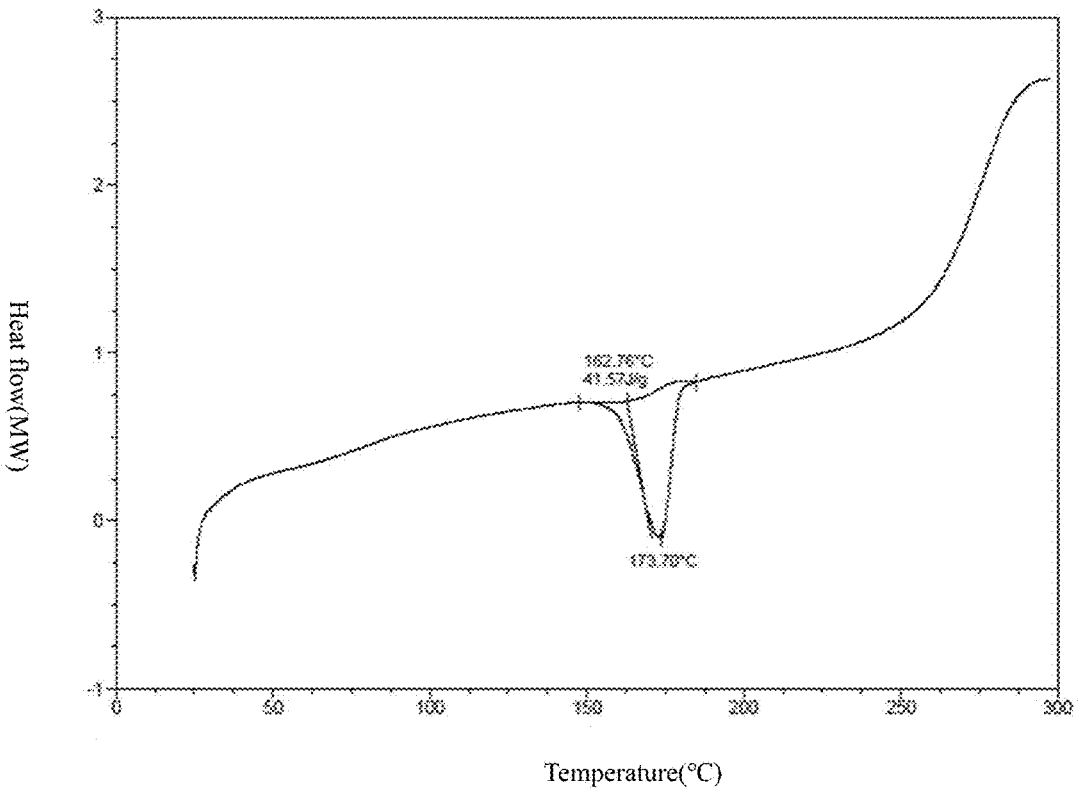
FIG. 34 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Methanesulfonate Form X.

The XPRD pattern, TGA pattern, and DSC pattern of Form X are shown in FIGS. 32, 33 and 34, respectively.

Example 20: Preparation of Form IX 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.4 mL of methanol and dichloromethane (the volume ratio of methanol to dichloromethane was 1:1), stirred at room temperature, added 1 equivalent of L-tartaric acid, sonicated, solids appeared immediately, continue to stir for 1 h, filter, vacuum drying at 50° C. overnight to obtain crystal form IX.

Figure 29:
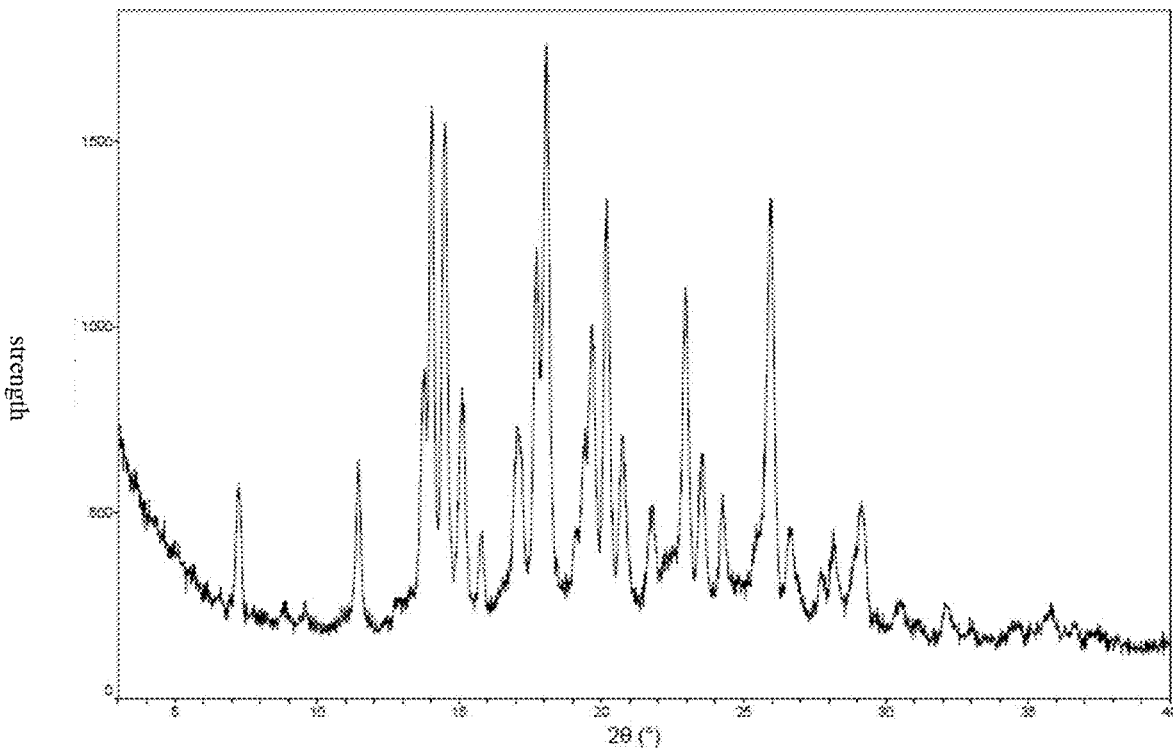
FIG. 29 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide L-tartrate crystal form IX.
Figure 30:
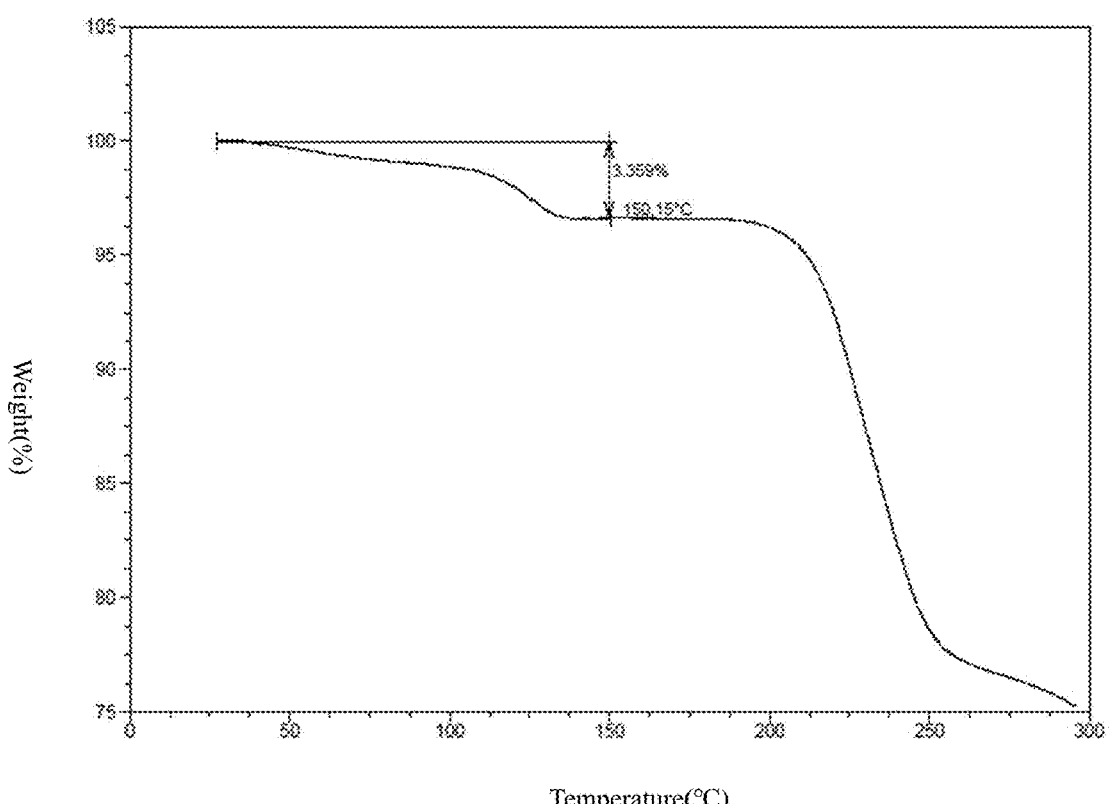
FIG. 30 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide L-tartrate crystal form IX.
Figure 31:
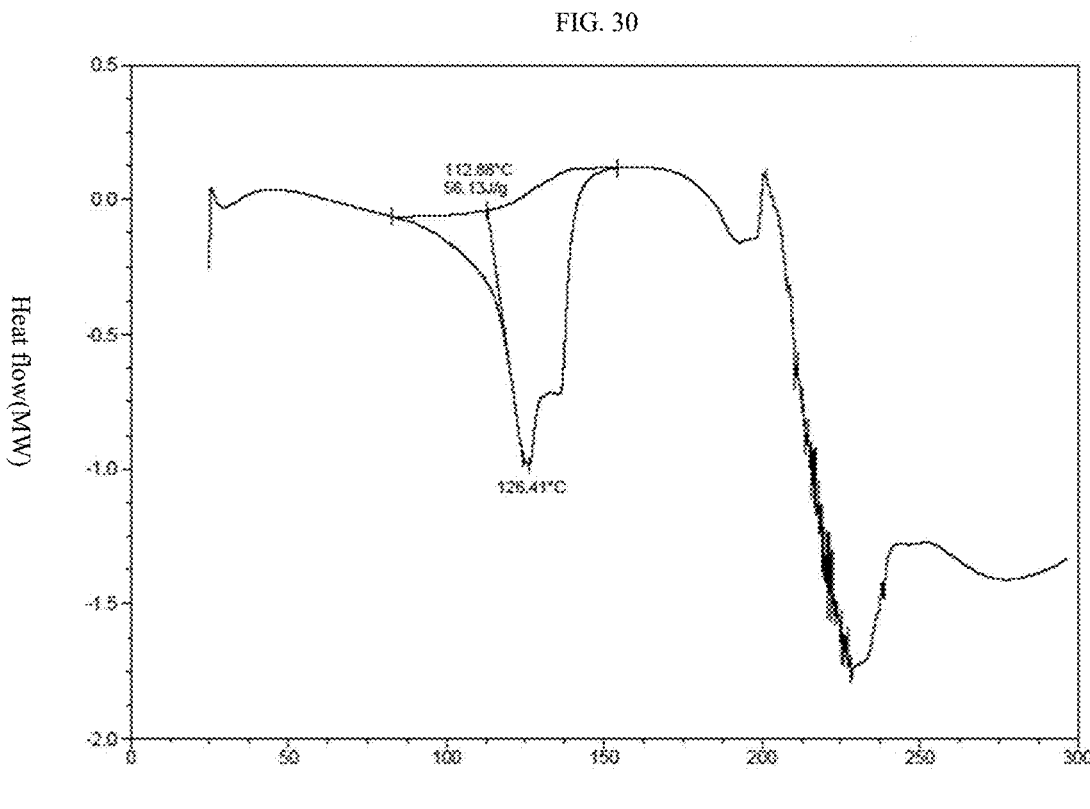
FIG. 31 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide L-tartrate crystal form IX.

The XPRD pattern, TGA pattern, and DSC pattern of Form IX are shown in FIGS. 29, 30, and 31, respectively.

Example 21: Preparation of Form II 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 0.5 mL of methanol and dichloromethane (the volume ratio of methanol to dichloromethane is 1:1), stirred at room temperature, and 1 equivalent of fumaric acid was added. A solid appeared immediately. Continue stirring overnight, filter, and vacuum at 50° C. Dry overnight to obtain crystal form II.

The XPRD pattern, TGA pattern, DSC pattern, DVS pattern and microscope picture of Form II are shown in FIGS. 6-10, respectively.

Effect Embodiment 4: Stability Test of Crystal Form II (Different Temperature and Humidity)

The stability study of the crystal form II prepared in Example 21 was carried out. Before the test, the single impurities of the crystal form II were less than 0.05%, and the total impurities were less than 0.05%.

Place the crystal form II at 60° C. and high humidity. Take samples at 0 days/5 days/10 days to investigate their content and related substances. The lighting conditions are: total illuminance ≥1.2×106 Lux·hr, near ultraviolet energy ≥200 w·hr/m2. The results are shown in Table 22.

TABLE 22

| Crystal form II | content | Single impurity | Total impurities | XPRD |
|---|---|---|---|---|
| 0 day | 98.7% | <0.05% | <0.05% | Crystal Form II |
| 5 days-high | 99.4% | <0.05% | <0.05% | Crystal Form II |
| 5 days-60° C. | 99.5% | <0.05% | <0.05% | Crystal Form II |
| 10 days-high | 99.0% | <0.05% | <0.05% | Crystal Form II |
| 10 days-60° C. | 99.2% | <0.05% | <0.05% | Crystal Form II |

The results show that the content and purity of crystal form II measured by sampling at 60° C. and high humidity in 5 and 10 days have hardly changed, and the content can reach 98.5 or even more than 90%. The content is less than 0.05 E, the total impurity content is less than 0.05, and the crystal form II shows good stability.

Effect Example 5: Study on the Stability of Crystal Form II (Different Solvents)

Weigh the sample crystal form II into a sample bottle, and then add a solvent to prepare a suspension. The resulting suspension is stirred at room temperature and 50° C. for 3-4 days, then filtered and collected the solid. After vacuum drying at room temperature, the solid was characterized. The results are shown in Table 23.

TABLE 23

| Suspension stirring experiment of crystal form II | | | |
|---|---|---|---|
| Serial number | solvent | Room temperature suspension | 50° C. suspension |
| 1 | methanol | Crystal Form II | Crystal Form II |
| 2 | ethanol | Crystal Form II | Crystal Form II |
| 3 | Isopropanol | Crystal Form II | Crystal Form II |
| 4 | Acetonitrile | Crystal Form II | Crystal Form II |
| 5 | Ethyl acetate | Crystal Form II | Crystal Form II |
| 6 | Isopropyl acetate | Crystal Form II | N/A |
| 7 | Tetrahydrofuran | Crystal Form II | Crystal Form II |
| 8 | N-heptane | Crystal Form II | N/A |
| 9 | 1,4-dioxane | Crystal Form II | N/A |
| 10 | Methanol: water 3:1 (v:v) | Crystal Form II | N/A |
| 11 | Acetone: water 1:2 (v:v) | N/A | Crystal Form XIV Fumarate acetonate |

Note:
The above N/A means not determined.

It can be seen from the above table that crystal form II has good stability at room temperature and 50° C.

Effect Example 6: Study on the Hygroscopicity of Crystal Form II

The crystalline form II prepared in Example 21 was used to conduct a moisture absorption study, and about 10 mg of crystalline form II was taken for a dynamic moisture adsorption (DVS) test. The conclusions are described in Table 24 below

TABLE 24

| Free base/salt | DVS (90% RH) | XRPD before and after DVS |
|---|---|---|
| Crystal Form II | 1.66% | Unchanged |

The above shows that the crystal form II is not easy to absorb water during storage, is easy to store, and can extend the shelf life.

Example 22: Preparation of Form VIII 40 mg of 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide was added to 0.5 mL of THF, heated to 60° C. and stirred, 1 equivalent of citric acid was added, and stirring was continued, solids appeared immediately, filtered, and dried under vacuum at 50° C. overnight to obtain crystal form VIII.

Figures 26, 27:
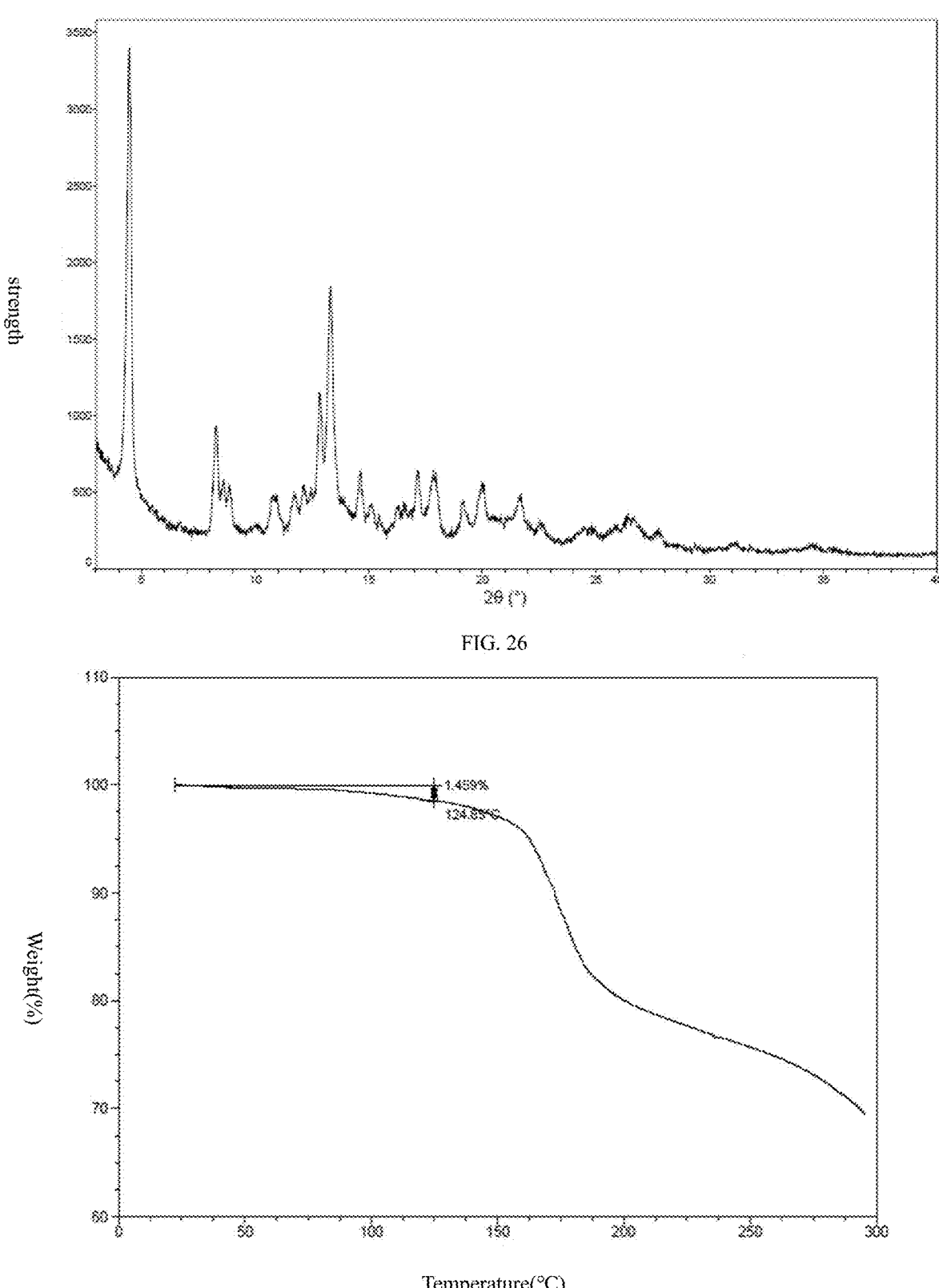
FIG. 26 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal Form VIII.
FIG. 27 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal Form VIII.
Figure 28:
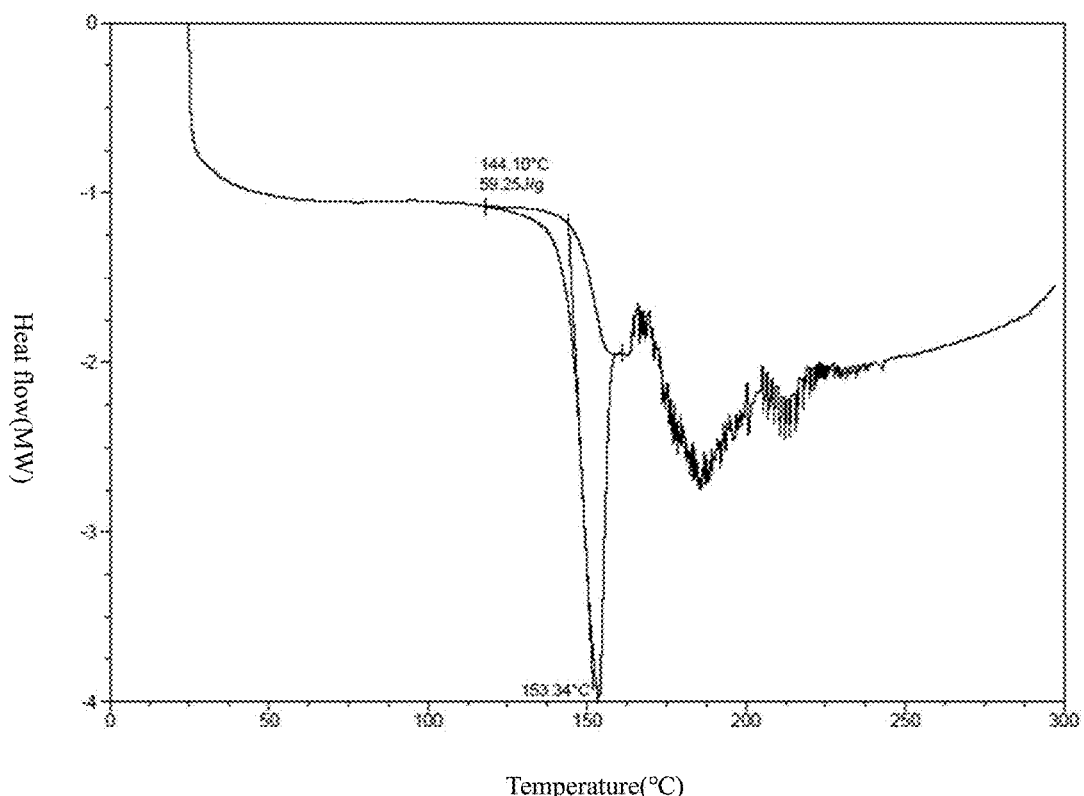
FIG. 28 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal Form VIII.

The XPRD pattern, TGA pattern, and DSC pattern of Form VIII are shown in FIGS. 26, 27 and 28, respectively.

Example 23: Preparation of Form XI 40 mg of 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide was added to 3 mL of tetrahydrofuran, and the sample was completely dissolved. After the solution was filtered, the filtrate was volatilized to dryness at room temperature to obtain crystal form XI.

Figure 35:
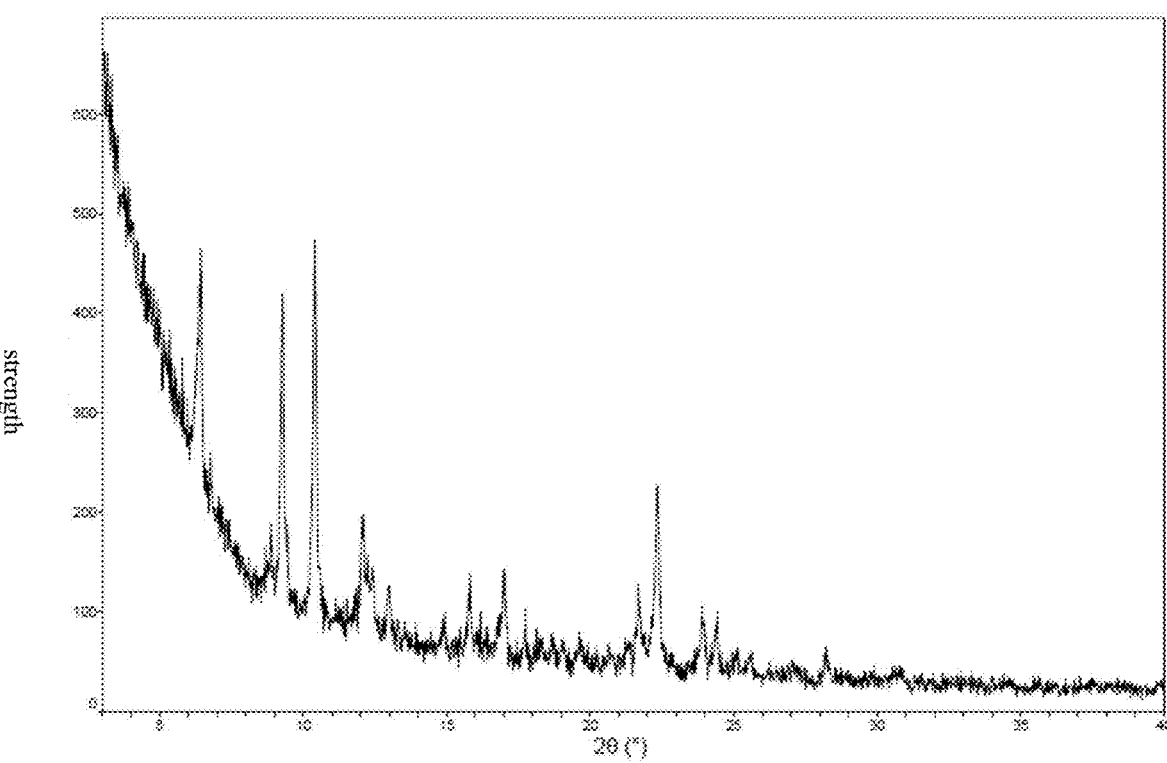
FIG. 35 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran Solvate Form XI.
Figures 36, 37:
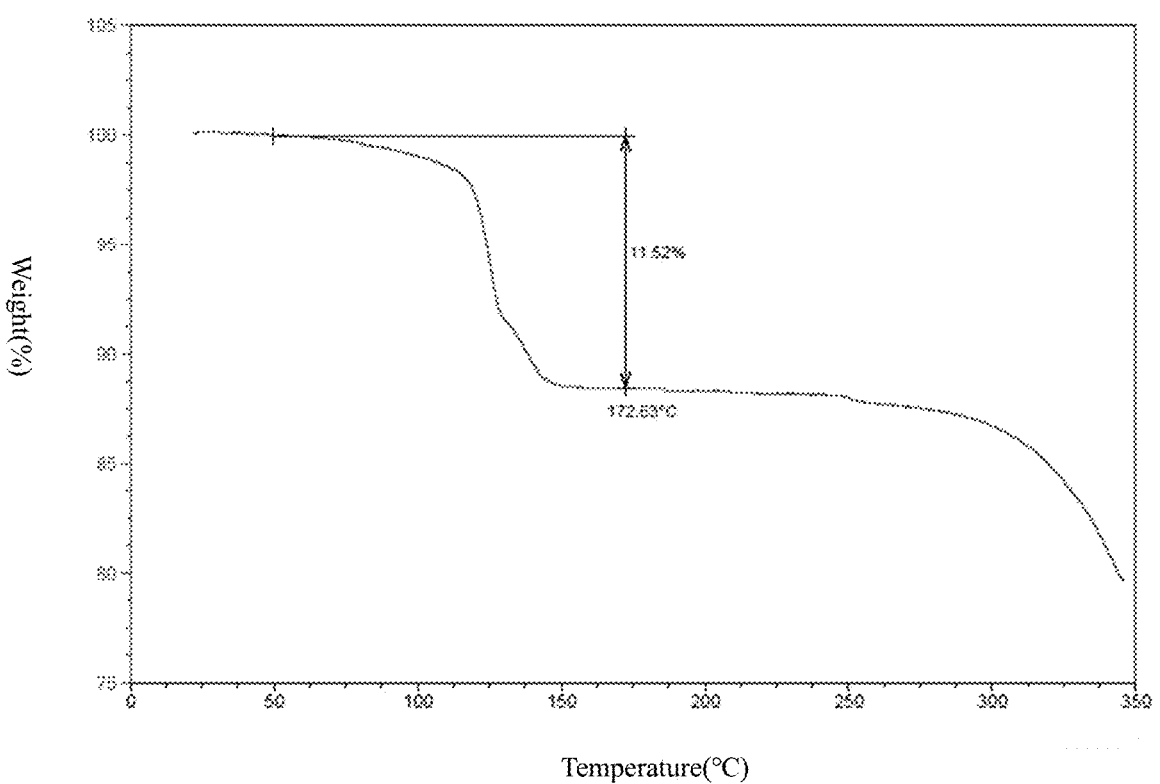
FIG. 36 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran Solvate Form XI.
FIG. 37 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran Solvate Form XI.

The XPRD pattern, TGA pattern, and DSC pattern of Form XI are shown in FIGS. 35, 36 and 37, respectively.

Example 24: Preparation of Form XII 40 mg of 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide was added to 2 mL of tetrahydrofuran, stirred at room temperature to dissolve the solid, and then 4 mL of methyl tert-butyl ether was added, stirred at room temperature, and filtered to obtain crystal form XII.

Figures 38, 39:
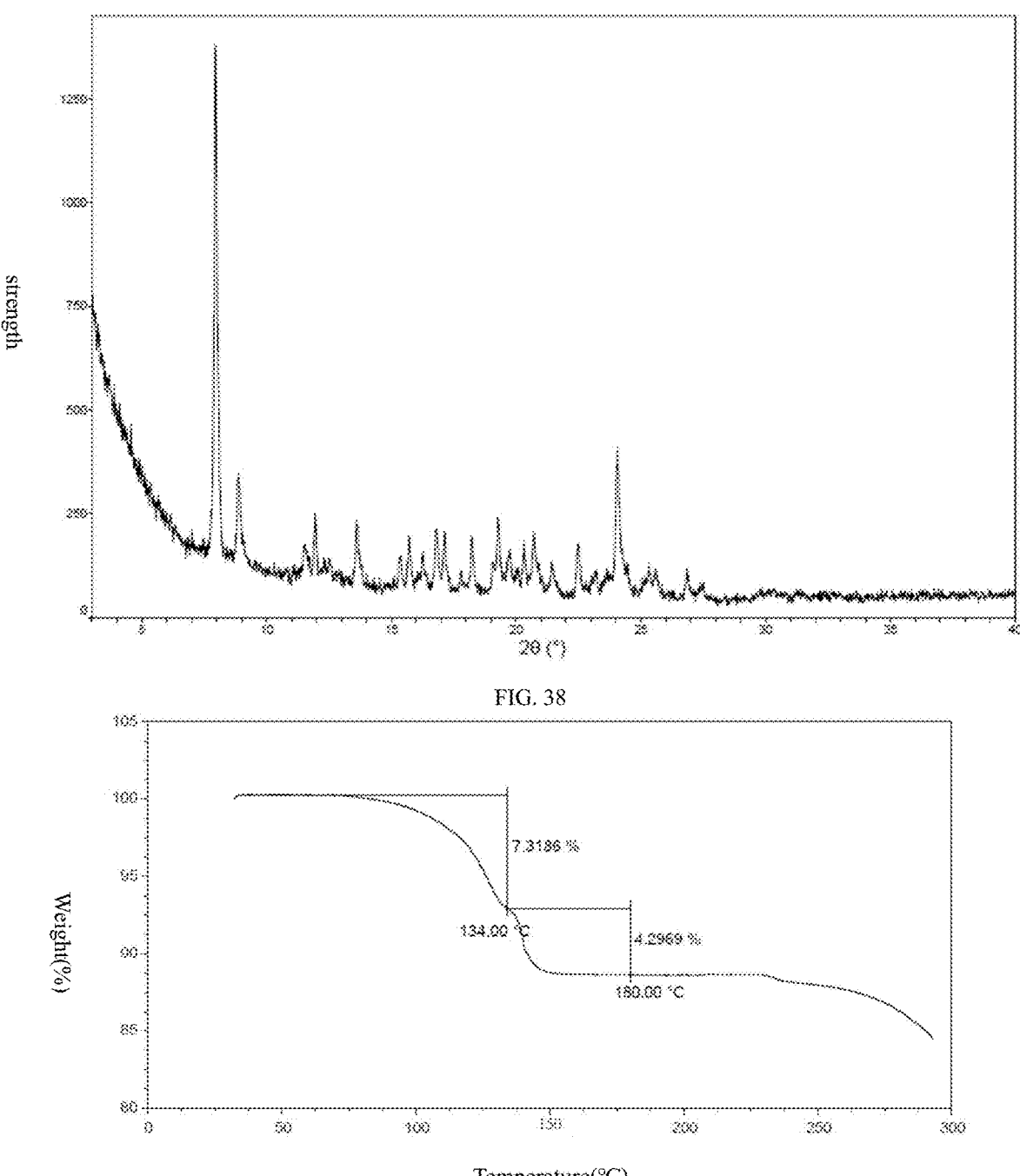
FIG. 38 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran-methyl tert-butyl ether solvate crystalline form XII.
FIG. 39 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran-methyl tert-butyl ether solvate crystalline form XII.
Figure 40:
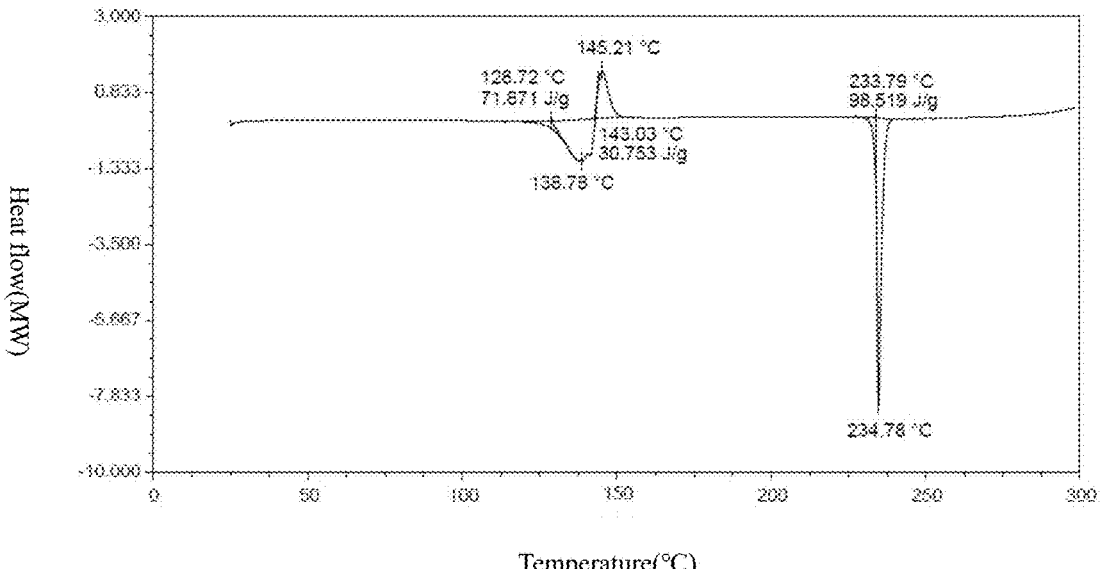
FIG. 40 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Tetrahydrofuran-methyl tert-butyl ether solvate crystalline form XII.

The XPRD pattern, TGA pattern, and DSC pattern of the crystal form XII are shown in FIGS. 38, 39 and 40, respectively.

Example 25: Preparation of Form XIII 40 mg of 3-((1H-pyrazolo[3,4-b]pyridin-5-yl)ethynyl)-4-methyl-N-(4-((4-methylpiperazine-1-yl) methyl)-3-(trifluoromethyl) phenyl) benzamide was added to 2 mL of tetrahydrofuran and stirred at room temperature to dissolve the solid. Subsequently, 2 mL of toluene was added, stirred at room temperature, and filtered to obtain crystal form XIII.

Figure 41:
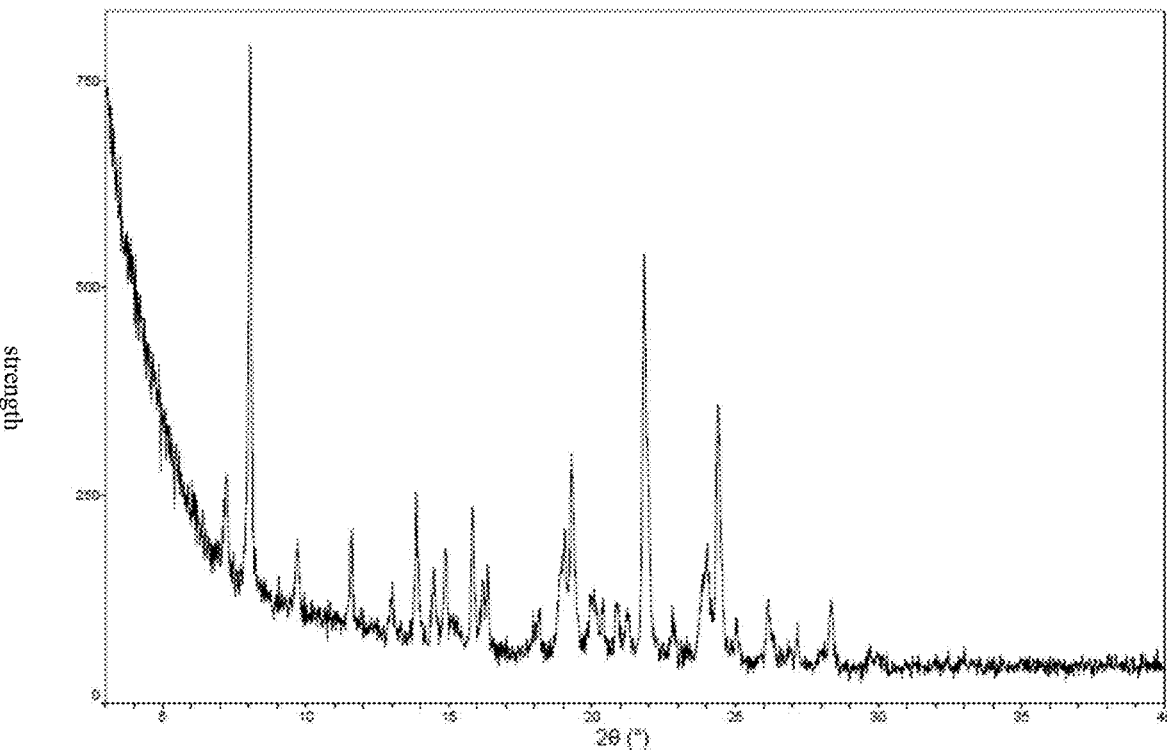
FIG. 41 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Toluene Solvate Form XIII.
Figure 42:
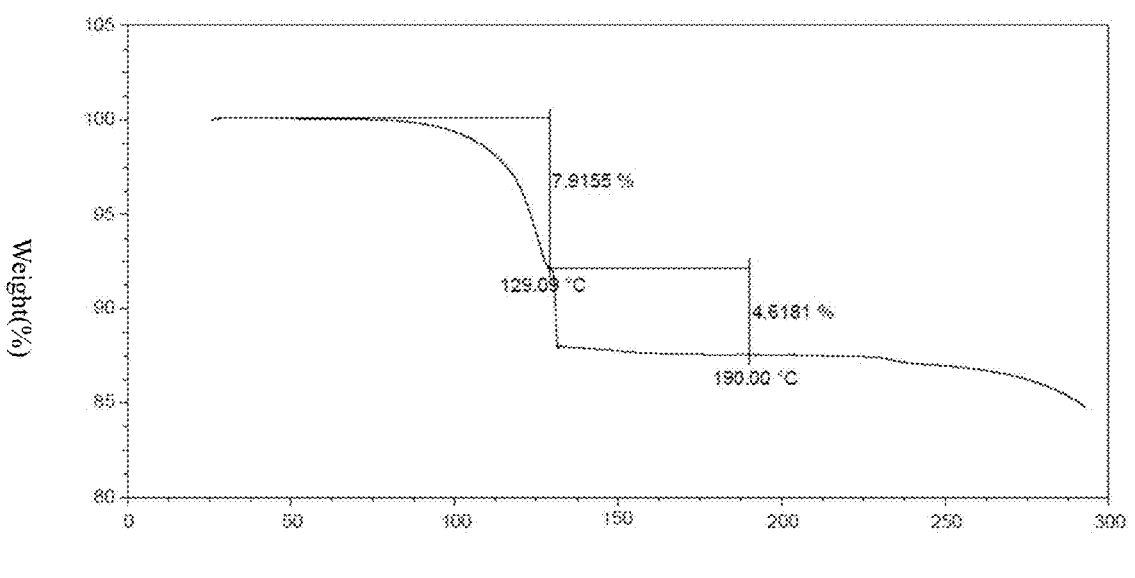
FIG. 42 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Toluene Solvate Form XIII.
Figure 43:
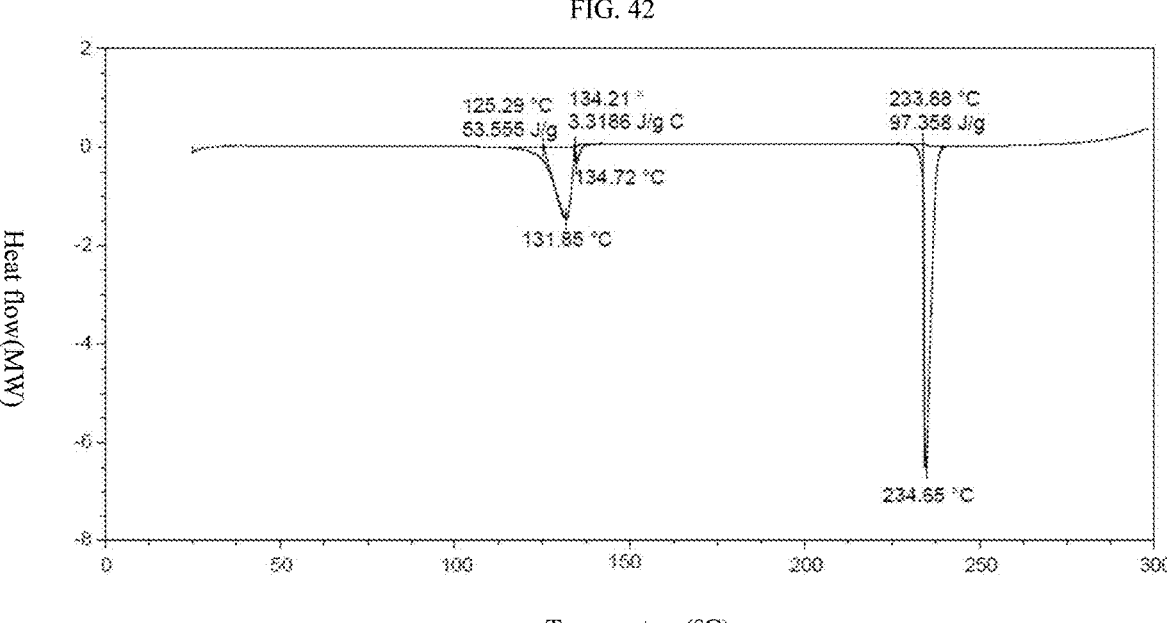
FIG. 43 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Toluene Solvate Form XIII.

The XPRD pattern, TGA pattern, and DSC pattern of the crystal form XIII are shown in FIGS. 41, 42 and 43, respectively.

Example 26: Preparation of Form XIV 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide fumarate crystal form II was gradually added with 0.4 mL of acetone to obtain a suspension sample, which was magnetically stirred (25° C., 600 rpm) and filtered to obtain crystal form XIV.

Figure 44:
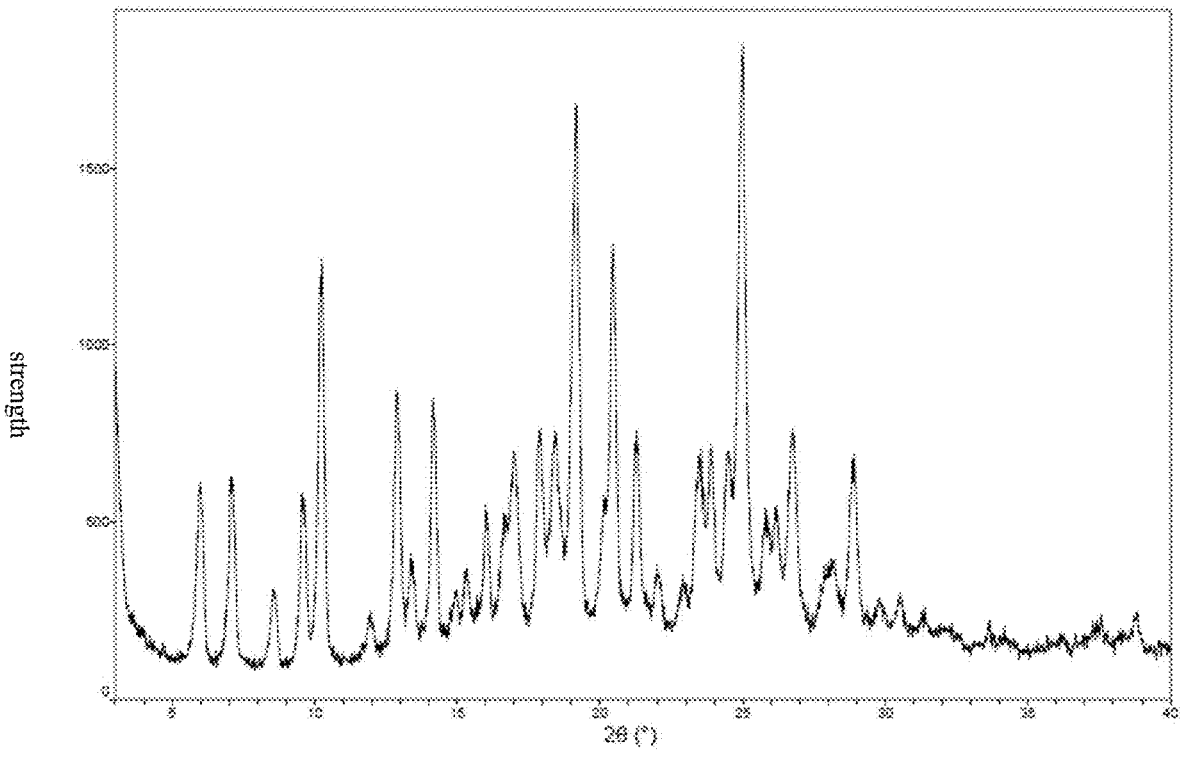
FIG. 44 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate acetonate crystal form XIV.
Figure 45:
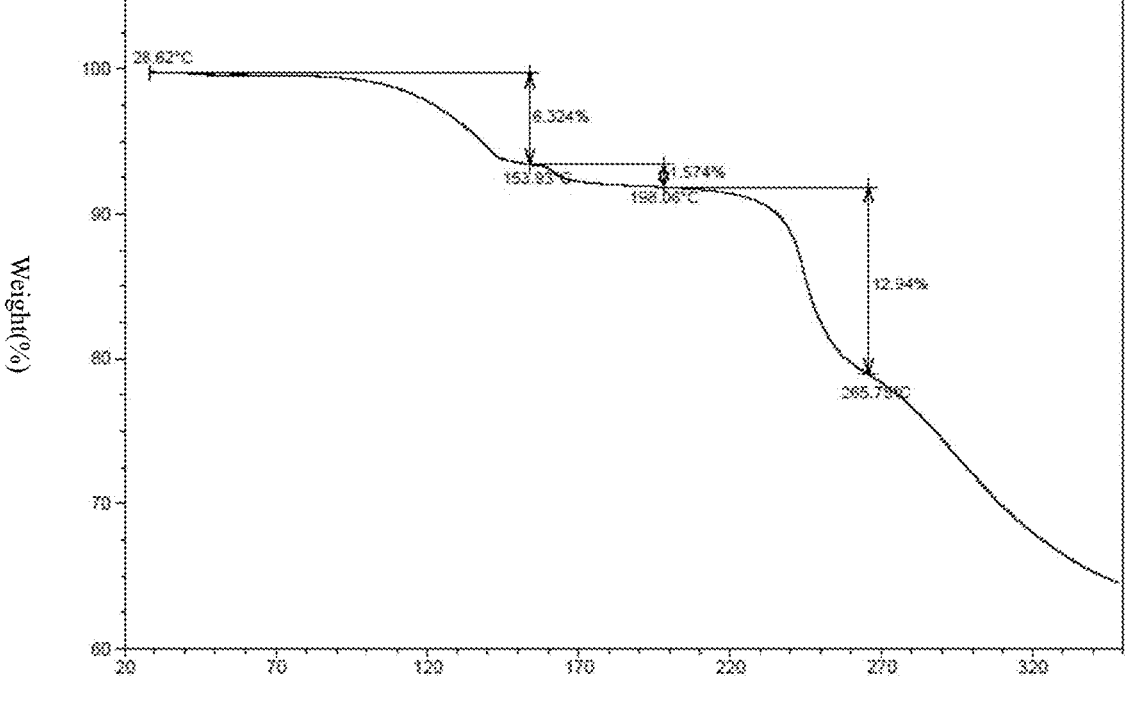
FIG. 45 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate acetonate crystal form XIV.
Figure 46:
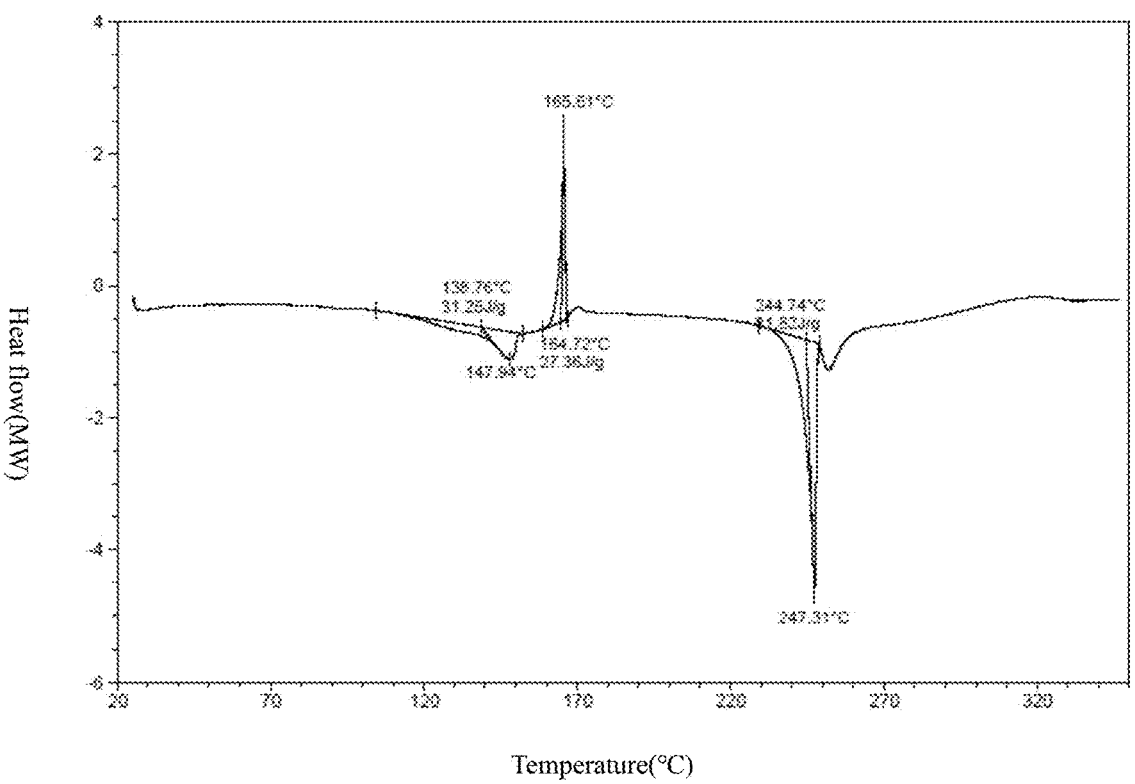
FIG. 46 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Fumarate acetonate crystal form XIV.
Figure 47:
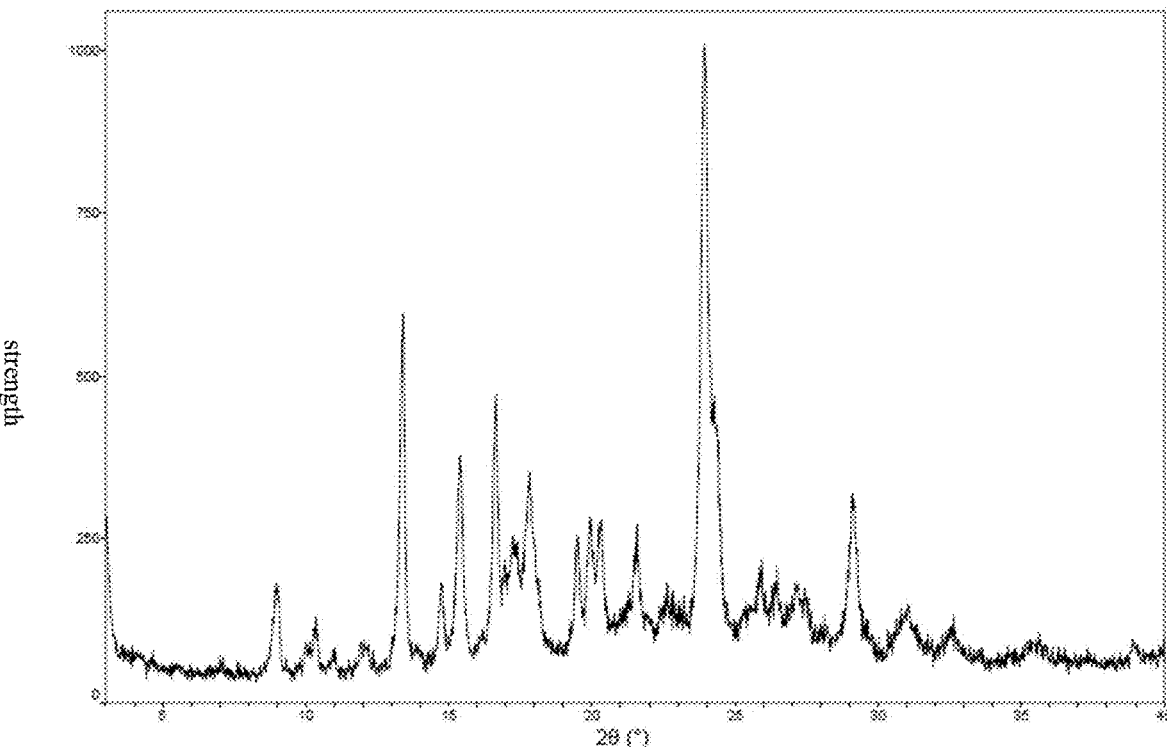
FIG. 47 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Monohydrochloride crystal form XV.
Figure 48:
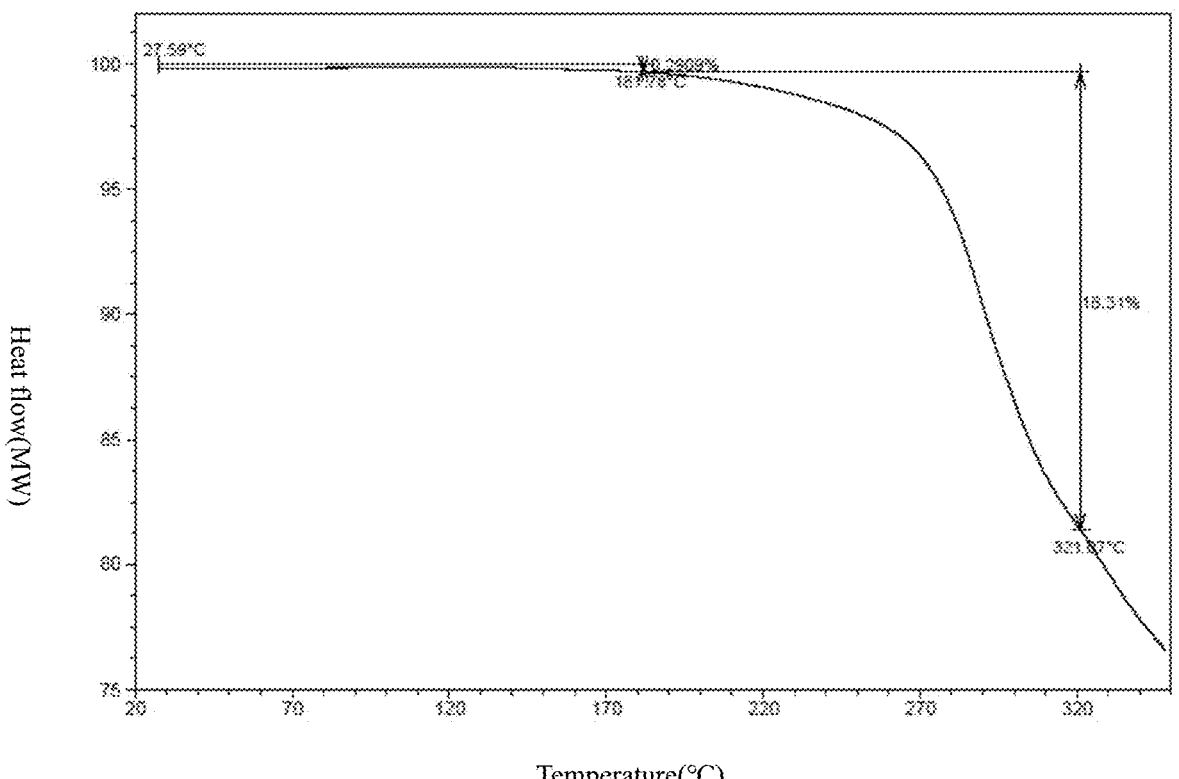
FIG. 48 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Monohydrochloride crystal form XV.
Figure 49:
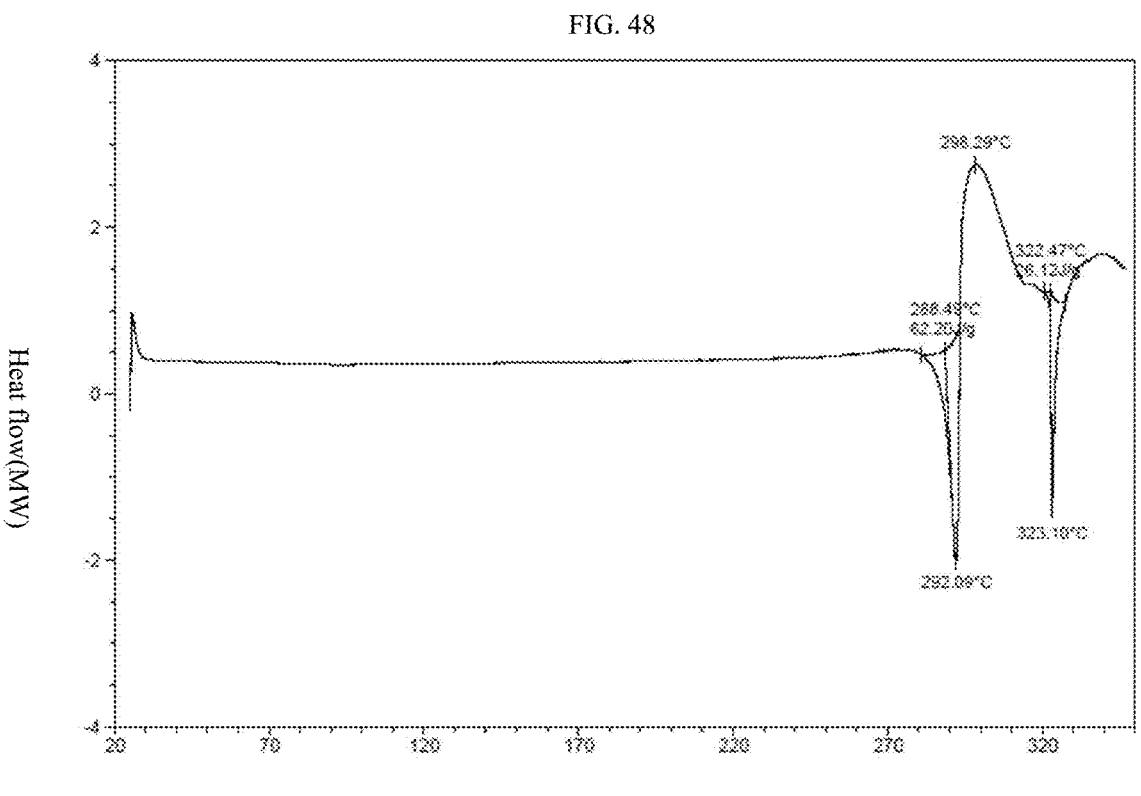
FIG. 49 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Monohydrochloride crystal form XV.
Figure 50:
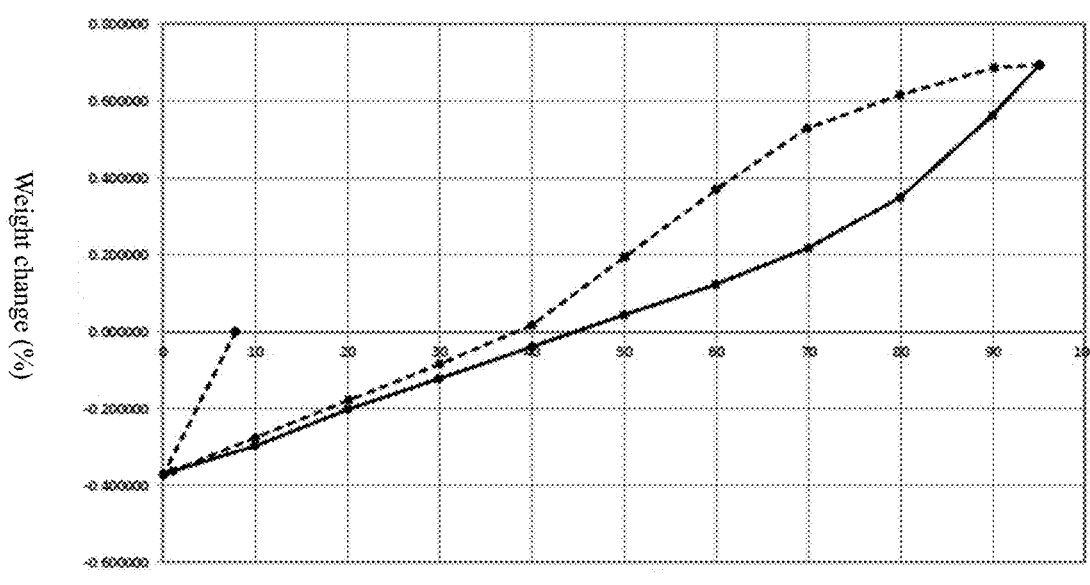
FIG. 50 is the DVS diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Monohydrochloride crystal form XV.

The XPRD pattern, TGA pattern, and DSC pattern of the crystal form XIV are shown in FIGS. 44, 45 and 46, respectively.

Example 27: Preparation of Form XV 3 g of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 60 mL THF with ultrasound to help dissolve, magnetically stir, add a hydrochloric acid solution (0.4 mL hydrochloric acid and 2 mL THF) with a molar ratio of raw material:acid of 1:0.9, stir at room temperature, avoid light, 600 rpm, stir overnight, and centrifuge. The residual solid was placed at 25° C. and dried under vacuum to obtain the crystal form XV.

The XPRD pattern, TGA pattern, DSC and DVS pattern of the crystal form XV are shown in FIGS. 47, 48, 49 and 50, respectively.

Example 28: Preparation of Form XVI 2 g of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide was added to 40 mL THF with ultrasound to aid dissolution, magnetically stir, add a hydrochloric acid solution with a molar ratio of raw material:acid of 1:2.1 (take 0.7 mL hydrochloric acid and 4 mL THF), seal the membrane and stir at room temperature and avoid light. After stirring overnight at 600 rpm, centrifuge and the remaining solid was placed at 25° C. and dried under vacuum to obtain crystal form XVI.

Figure 51:
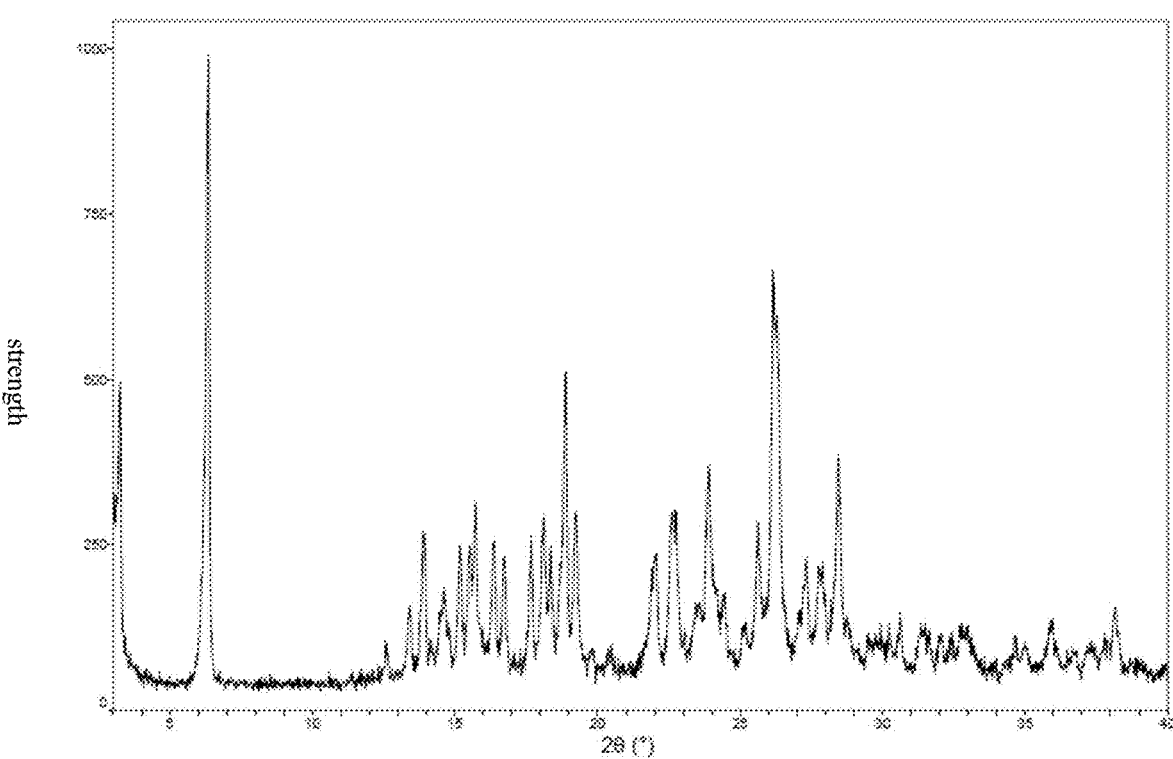
FIG. 51 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form XVI.
Figure 52:
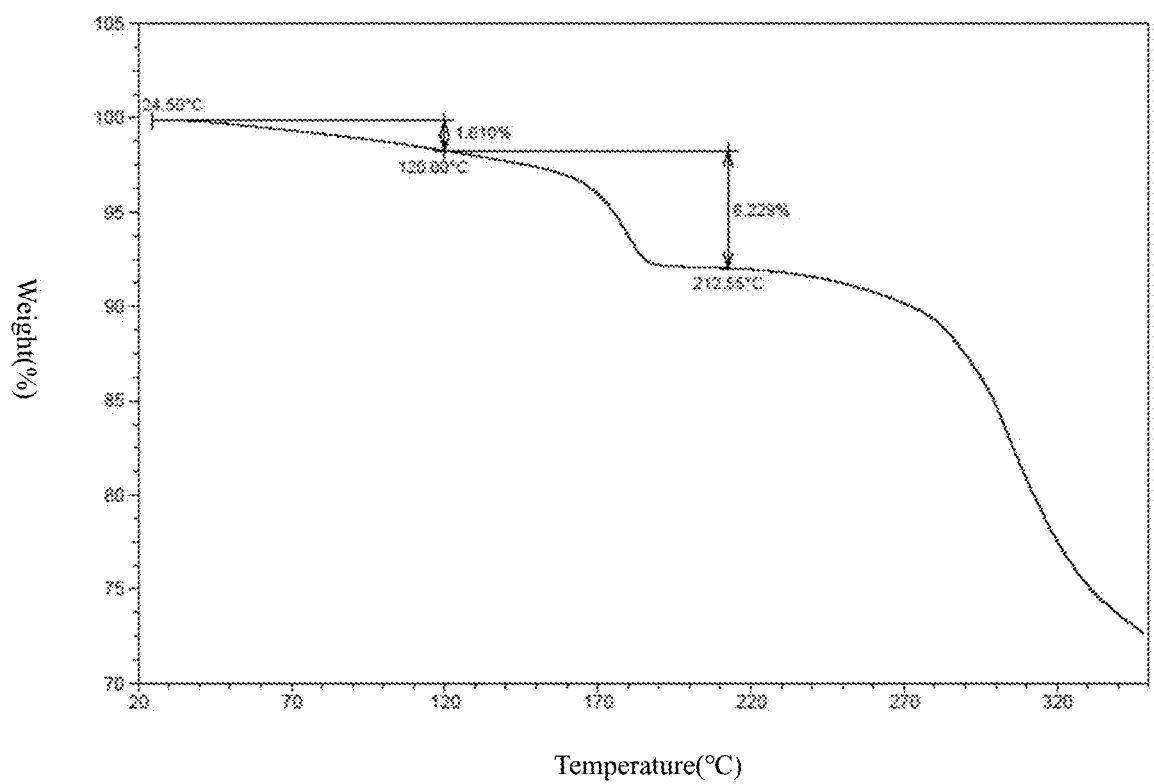
FIG. 52 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form XVI.
Figure 53:
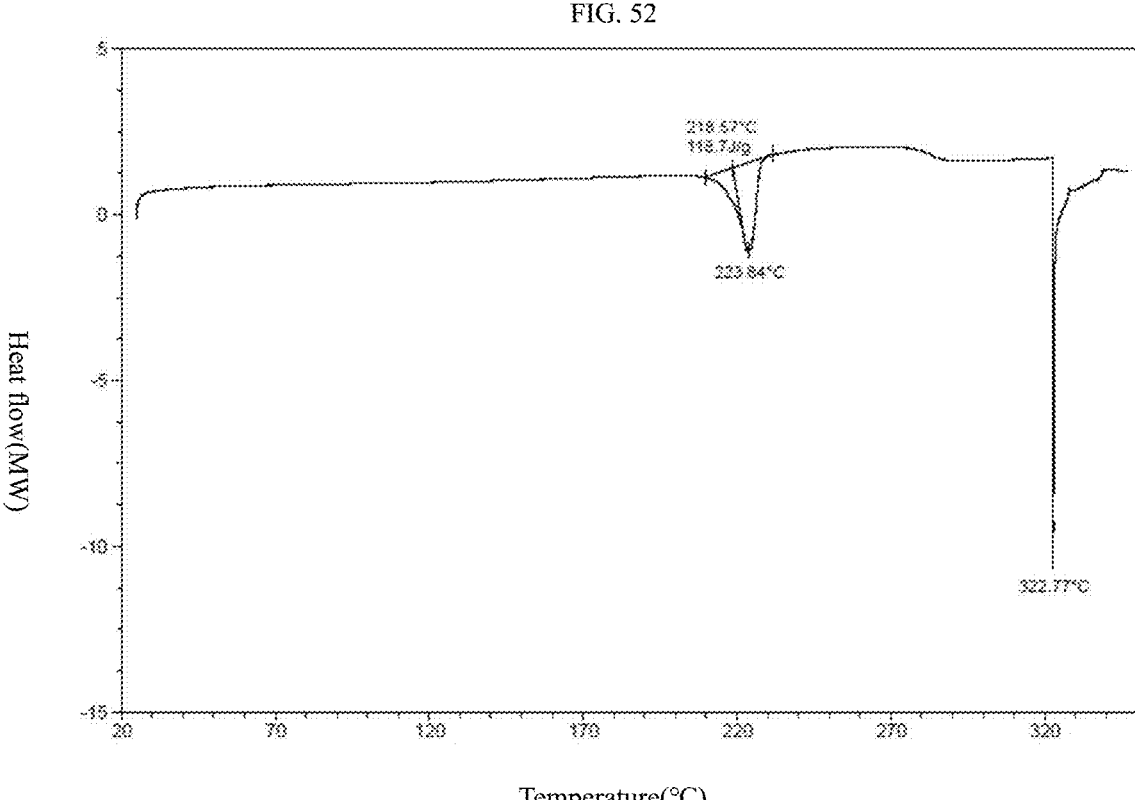
FIG. 53 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form XVI.

The XPRD pattern, TGA pattern and DSC of the crystal form XVI are shown in FIGS. 51, 52, and 53, respectively.

Example 29: Preparation of Form XVII 40 mg of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide dihydrochloride was added to 0.4 mL of ethyl acetate to obtain a suspension sample, magnetically stirred overnight, and centrifuged at 40° C. at 600 rpm, and the remaining solid was placed at 25° C. and dried under vacuum to obtain crystal form XVII.

Figures 54, 55:
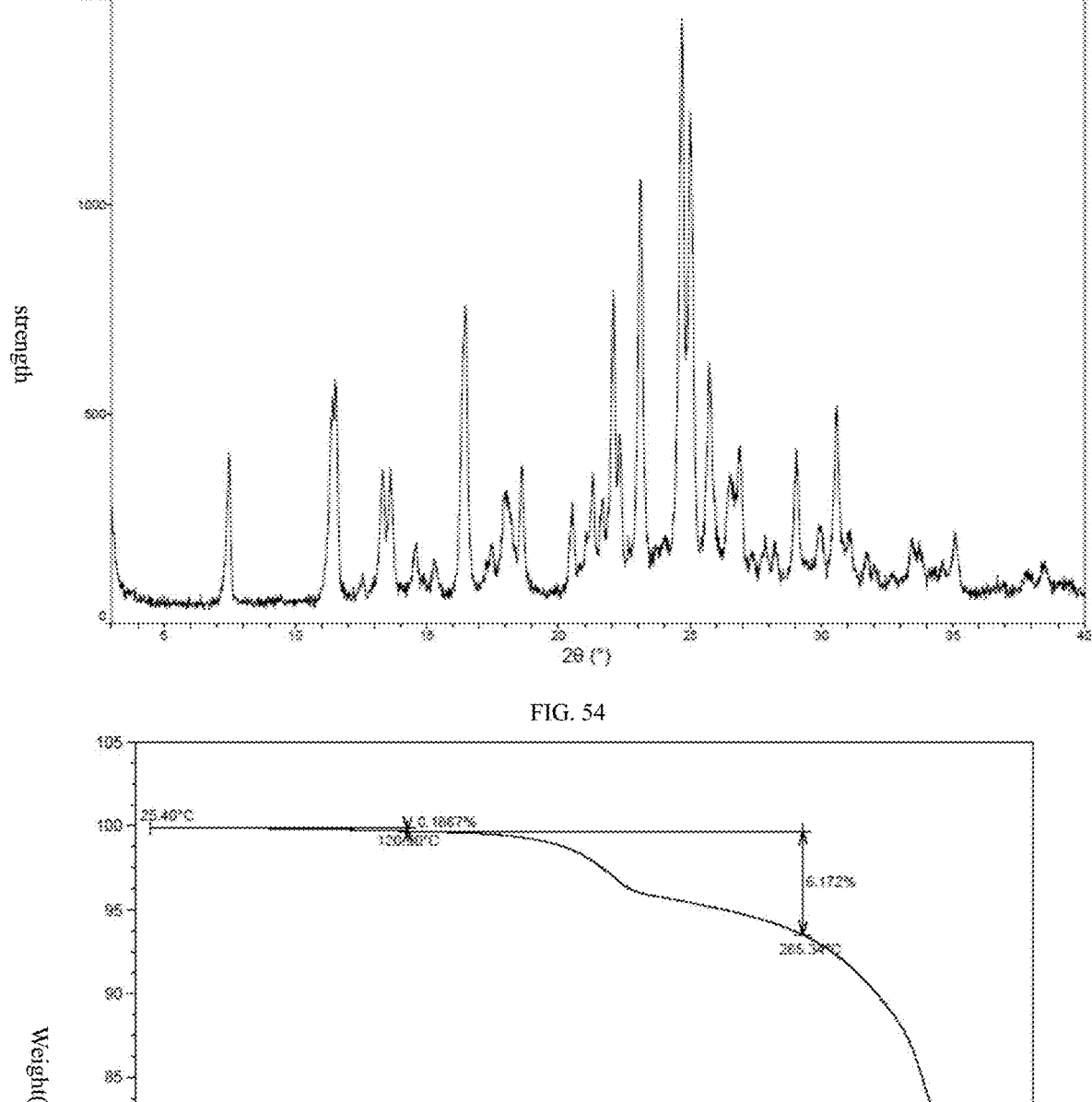
FIG. 54 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form XVII.
FIG. 55 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Dihydrochloride crystal form XVII.
Figure 56:
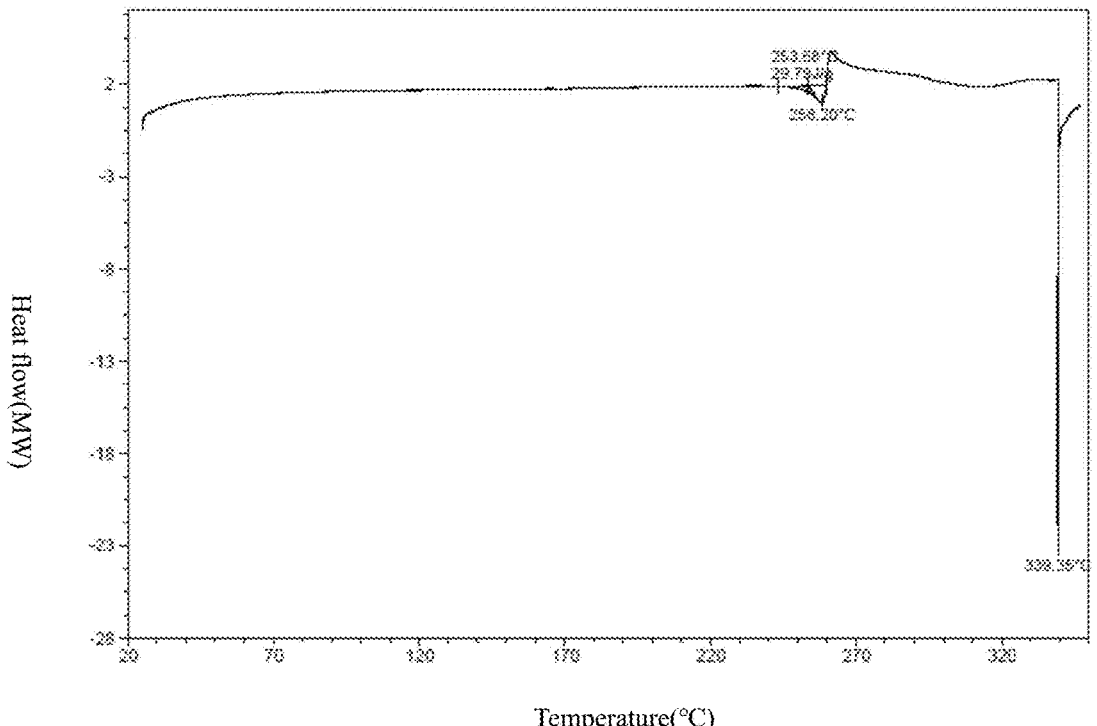
FIG. 56 is the DSC diagram of 3-((1H-pyrazolo[3,4-b]pyridin-5-yl)ethynyl)-4-methyl-N-(4-((4-methylpiperazine- 1-yl)methyl)-3-(trifluoromethyl) phenyl) benzamide Dihydrochloride crystal form XVII.

The XPRD pattern, TGA pattern and DSC of the crystal form XVII are shown in FIG. 54, FIG. 55 and FIG. 56, respectively.

Example 30: Preparation of Form XVIII 1 g of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide dihydrochloride was added to 20 mL THF with ultrasound to aid dissolution, magnetically stir, add citric acid (the molar ratio of raw material:citric acid is 1:1), seal the membrane and stir overnight (at room temperature, protected from light, 600 rpm). After stirring overnight, the sample was in a suspended state. After centrifugation, 20 mL THF was added to the residual solids and then centrifuged. After centrifugation, 20 mL water was added to find that the sample was almost dissolved. Then the solvent was removed by a rotary evaporator and dried in a vacuum drying cabinet to obtain 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide citrate.

Place 40 mg of the above citrate in a glass bottle, add 0.4 mL of mixed solvent (the volume ratio of methanol:water is 1:1) to prepare a suspension sample, magnetically stir (25° C., 600 rpm), after stirring for 3 days, The turbid liquid sample was centrifuged, and the residual solid sample was placed in a vacuum drying oven at 25° C. to dry overnight to obtain crystal form XVIII.

Figure 57:
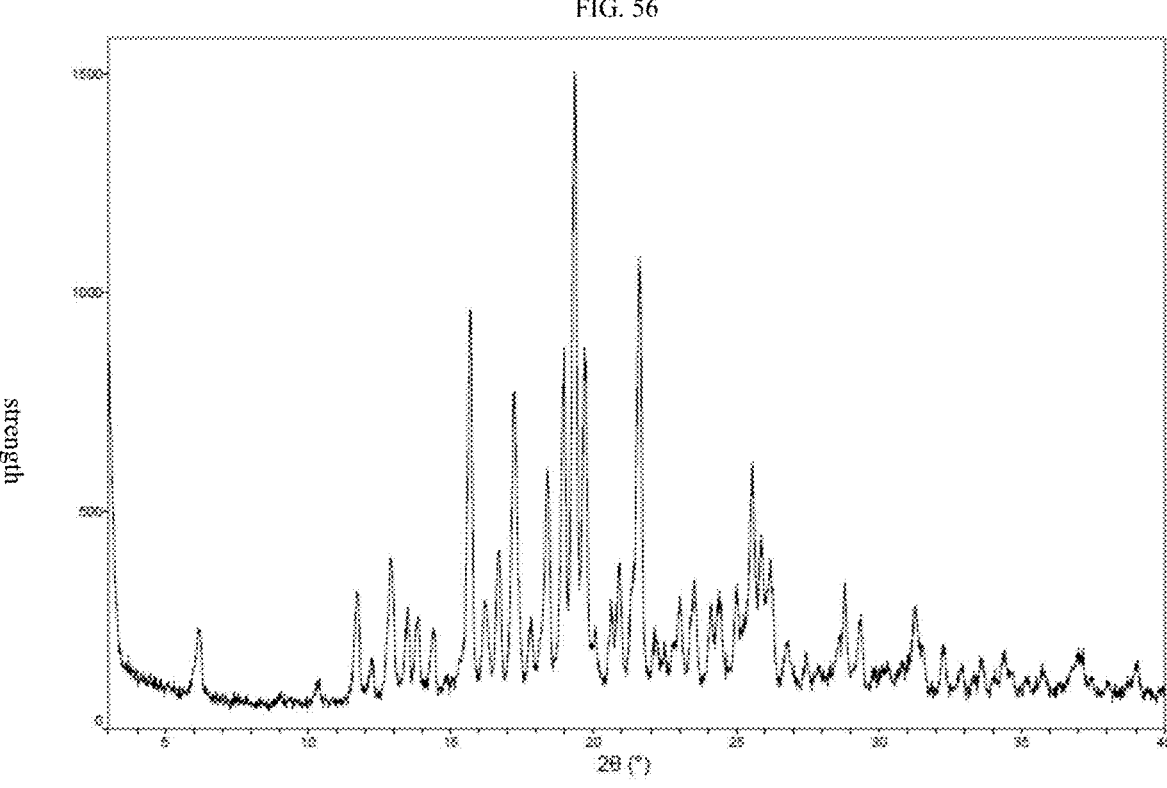
FIG. 57 is the XPRD pattern of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal form XVIII.
Figure 58:
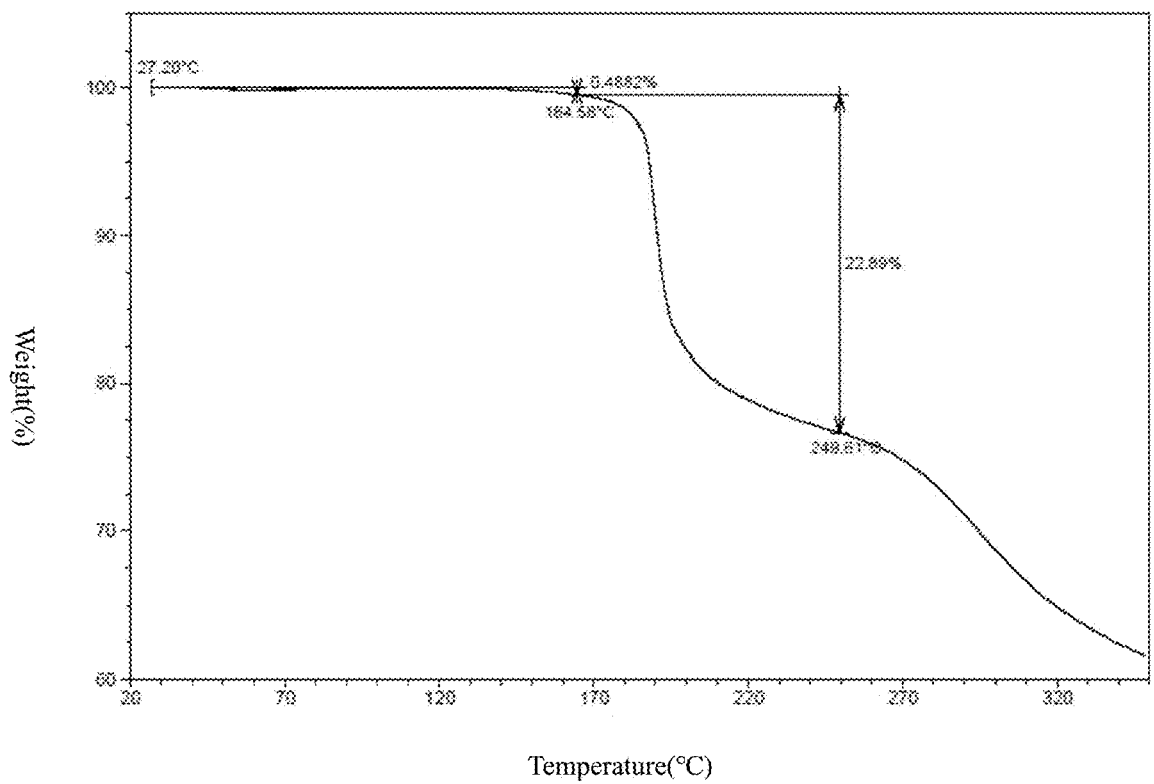
FIG. 58 is the TGA diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal form XVIII.
Figure 59:
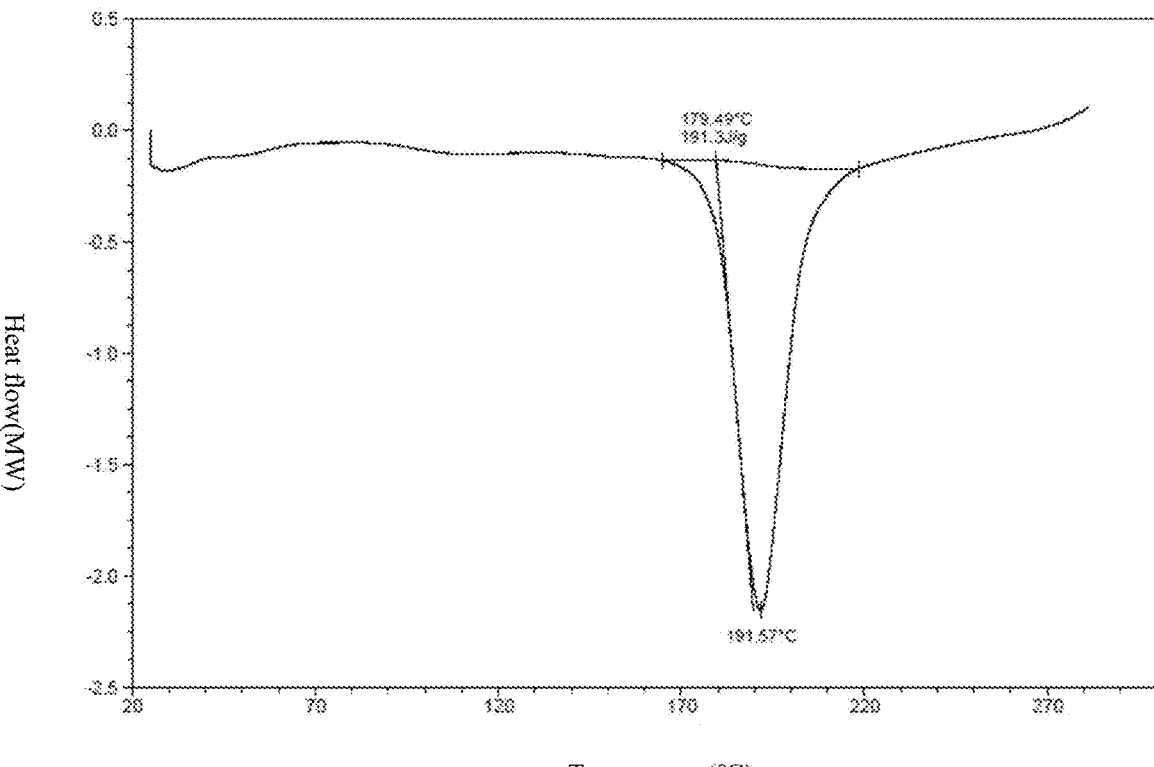
FIG. 59 is the DSC diagram of 3-((1H-pyrazolo[3,4-b]pyridin-5-yl)ethynyl)-4-methyl-N-(4-((4-methylpiperazine-1-yl)methyl)-3-(trifluoromethyl) phenyl) benzamide Citrate crystal form XVIII.

The XPRD pattern, TGA pattern and DSC of the crystal form XVIII are shown in FIG. 57, FIG. 58, and FIG. 59, respectively.

The invention claimed is:

1. A crystal form of 3-((1H-pyrazolo[3,4-b]pyridin-5-yl) ethynyl)-4-methyl-N-(4-((4-methylpiperazine-1-yl) methyl)-3-(trifluoromethyl) phenyl) benzamide, which has characteristic XRPD diagram peaks at the following positions represented by 2θ angles: 9.498±0.2°, 12.293±0.2°, 13.045±0.2°, 15.899±0.2°, 16.199±0.2°, 18.183±0.2°, 18.327±0.2°, 21.755±0.2°, 22.362=0.2°, and 25.690±0.2°.

2. The crystal form of claim 1, which has characteristic XRPD diagram peaks at the following positions represented by 2θ angles: 8.968±0.2°, 9.498±0.2°, 12.293=0.2°, 13.045±0.2°, 15.899±0.2°, 16.199=0.2°, 16.533=0.2°, 16.908±0.2°, 18.183=0.2°, 18.327±0.2°, 20.042=0.2°, 20.271=0.2°, 21.755±0.2°, 22.362=0.2°, and 25.690=0.2°.

3. The crystal form of claim 1, which exhibits a weight loss of 0.15% at 200° C., as determined by thermogravimetric analysis; or exhibits a thermal absorption peak at 235° C., as determined by differential scanning calorimetry (DSC).

4. A method for preparing the crystal form of claim 1, comprising the step of crystallizing 3-((1H-pyrazole[3,4-b] pyridine-5-substituted) ethynyl)-4-methyl-n-(4-((4-methylpiperazine-1-substituted) methyl)-3-(trifluoromethyl) phenyl) benzamide in an organic solvent, wherein the organic solvent is one or more of $C_1$-$C_{10}$ alkane, $C_1$-$C_4$ alcohol, ether, nitrile, ketone, ester or DMSO.

5. The method of claim 4, wherein
   the crystallization is performed by suspension stirring, room temperature stirring, heating and cooling crystallization, solvent volatilization or anti-solvent addition;
   the organic solvent is one or more of heptane, methanol, ethanol, isopropanol, methyl tert-butyl ether, acetonitrile, acetone, 2-butanone, ethyl acetate, isopropyl acetate or dimethyl sulfoxide;
   the mass/volume ratio of the 3-((1H-pyrazolo[3,4-b]pyridin-5-yl) ethynyl)-4-methyl-N-(4-((4-methylpiperazine-1-yl) methyl)-3-(trifluoromethyl) phenyl) benzamide to the organic solvent is from 1/1 g/mL to 1/5 g/mL;
   the crystallization temperature is from 20° C. to 50° C.; or the crystallization time is from 1 hour to 36 hours.

6. The method of claim 4, wherein the crystallization comprises the addition of an anti-solvent, wherein the anti-solvent is one or more of water, alcohol or nitrile;
   wherein the water is distilled water, deionized water, purified water, tap water or mineral water;
   wherein the alcohol is isopropanol;
   wherein the nitrile is acetonitrile; or
   wherein the mass/volume ratio of the 3-((1H-pyrazolo[3, 4-b]pyridin-5-yl) ethynyl)-4-methyl-N-(4-((4-methylpiperazine-1-yl) methyl)-3-(trifluoromethyl) phenyl) benzamide to the anti-solvent is from 1/2 g/mL to 1/25 g/mL.

7. A pharmaceutical composition comprising the crystal form of claim 1 and a pharmaceutically acceptable excipient.

8. A method of treating or preventing cancer, comprising administering the crystal form of claim 1 to a subject having the cancer.

* * * * *